(12) United States Patent
Mjalli et al.

(10) Patent No.: US 6,933,303 B2
(45) Date of Patent: Aug. 23, 2005

(54) HETEROARYL-FUSED NITROGEN HETEROCYCLES AS THERAPEUTIC AGENTS

(75) Inventors: Adnan M. M. Mjalli, Jamestown, NC (US); Robert C. Andrews, Jamestown, NC (US); Rongyuan Xie, High Point, NC (US); Ravindra R. Yarragunta, High Point, NC (US); Tan Ren, High Point, NC (US)

(73) Assignee: TransTech Pharma, Inc., High Point, NC (US)

( * ) Notice: Subject to any disclaimer, the term of this patent is extended or adjusted under 35 U.S.C. 154(b) by 63 days.

(21) Appl. No.: 10/274,546

(22) Filed: Oct. 18, 2002

(65) Prior Publication Data

US 2004/0014778 A1 Jan. 22, 2004

Related U.S. Application Data

(60) Provisional application No. 60/346,125, filed on Oct. 19, 2001, and provisional application No. 60/346,176, filed on Oct. 19, 2001.

(51) Int. Cl.[7] ..................... A61K 31/437; C07D 471/04
(52) U.S. Cl. .......................... 514/292; 546/87; 546/86; 546/85; 546/80; 514/291
(58) Field of Search .................................. 514/292, 291; 546/87, 86, 85, 80

(56) References Cited

U.S. PATENT DOCUMENTS 6,069,150 A * 5/2000 Spinelli et al. ............. 514/312

FOREIGN PATENT DOCUMENTS

| WO | WO 92/04348 | * 3/1992 | ............... 514/292 |
|---|---|---|---|
| WO | WO 98/56376 | 12/1998 | |
| WO | WO 99/46244 | 9/1999 | |

OTHER PUBLICATIONS

Ishida, J. et al.: Antitumor agents 201. Cytotoxicity of harmine and beta–carboline analogs. Bioorg. & Med. Chem. Lett. vol. 9, pp. 3319–3324, 1999.*

Brossi, A. et al.: Alkaloids in mammalian tissues. J. Med. Chem. vol. 16, pp. 418–420, 1973.*

Deveau, et al., "The Synthesis of Amino–Acid Functionalized B–Carbolines as Topoisomerase II Inhibitors" Bioorganic & Medicinal Chem. Ltrs.II, pp. 1251–1255 (2001).

Fantauzzi, et al., "Synthesis of Diverse Tetrahydro–B–Carboline3–Carboxamides and –2,3–Bis– lactams On a Versatile 4–Hydroxythiophenol–Linked Solid Support", Tetrahedron Letters, vol. 39 pp. 1291–1294 (1998).

PCT International Search Report for PCT/US02/33520.

Iversen, L.F., et al., Steric Hindrance as a Basis for Structure–Based Design of Selective Inhibitors of Protein–Tyrosine Phosphatases, Biochemistry, 2001, 40, No. 49, 14812–14820.

Bleasdale, J.E., et al., Small Molecule Peptidomimectics Containing a Novel Phosphotyrosine Bioisostere Inhibit Protein Tyrosine Phosphatase 1B and Augment Insulin Action, Biochemistry, 2001, 40, 5642–5654.

Shim, Y.S., et al., Formylchromone Derivatives as a Novel Class of Protein Tyrosine Phosphatase 1B Inhibitors, Bioorganic & Medicinal Chemistry Letters, 13, (2003) 2561–2563.

Cheon, H.G., et al., Discovery of a Novel Protein Tyrosine Phosphatase–1N Inhibitor, KR61639: Potential Development as an Antihyperglycemic Agent, European Journal of Pharmacology, 485 (2004) 333–339.

Urbanek, R.A., et al., Potent Reversible Inhibitors of Protein Tyrosine Phosphatase CD45, J. Med. Chem., 2001, 44, 1777–1793.

Umezawa, K., et al., Molecular Design and Biological Activities of Protein–Tyrosine Phosphatase Inhibitors, Pharmacology & Therapeutics, 99, (2003), 15–24.

Sarmiento, M., et al., Structure–Based Discovery of Small Molecule Inhibitors Targeted to Protein Tyrosine Phosphatase 1B, J. Med. Chem., 2000, 43, 146–155.

* cited by examiner

Primary Examiner—Charanjit S. Aulakh
(74) Attorney, Agent, or Firm—Kilpatrick Stockton

(57) ABSTRACT

This invention provides compounds which are useful as inhibitors of protein tyrosine phosphatases (PTPases). As inhibitors of PTPases, the compounds of the invention are useful for the management, treatment, control and adjunct treatment of diseases mediated by PTPase activity. Such diseases include type I diabetes, type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

13 Claims, No Drawings

HETEROARYL-FUSED NITROGEN HETEROCYCLES AS THERAPEUTIC AGENTS

STATEMENT OF RELATED APPLICATIONS

The present application claims priority under 35 USC 119 from the following U.S. Provisional Applications: Ser. No. 60/346,125, filed Oct. 19, 2001, entitled "Heteroaryl-Fused Nitrogen Heterocycles as Therapeutic Agents"; Ser. No. 60/346,176, filed Oct. 19, 2001, entitled "Heteroaryl-Fused Heterocyclic Aminoamide Derivatives as Therapeutic Agents", the entirety of which are herein incorporated by reference.

FIELD OF THE INVENTION

This invention relates to compounds which are inhibitors of protein tyrosine phosphatases (PTPases), which are useful for the management, treatment, control, or adjunct treatment of diseases caused by over-activity of PTPases.

BACKGROUND OF THE INVENTION

The process of protein phosphorylation is now recognized as central to the fundamental processes of cellular signal transduction. Alterations in protein phosphorylation, may therefore constitute either a physiological or pathological change in an in vivo system. Protein de-phosphorylation, mediated by phosphatases, is also central to certain signal transduction processes.

The two major classes of phosphatases are (a) protein serine/threonine phosphatases (PSTPases), which catalyze the dephosphorylation of serine and/or threonine residues on proteins or peptides; and (b) the protein tyrosine phosphatases (PTPases), which catalyze the dephosphorylation of tyrosine residues on proteins and/or peptides. A third class of phosphatases is the dual specificity phosphatases, or DSP's, which possess the ability to act both as PTPases and as PSTPases.

Among the PTPases there exist two important families, the intracellular PTPases, and the transmembrane PTPases. The intracellular PTPases include PTP1B, STEP, PTPD1, PTPD2, PTPMEG1, T-cell PTPase, PTPH1, FAP-1/BAS, PTP1D, and PTP1C. The transmembrane PTPases include LAR, CD45, PTPα, PTPβ, PTPδ, PTPε, PTPξ, PTPκ, PYPμ, PTPσ, HePTP, SAP-1, and PTP-U2. The dual—specificity phosphatases include KAP, cdc25, MAPK phosphatase, PAC-1, and rVH6.

The PTPases, especially PTP1B, are implicated in insulin insensitivity characteristic of Type II diabetes (Kennedy, B. P.; Ramachandran, *C. Biochem. Pharm.* 2000, 60, 877–883). The PTPases, notably CD45 and HePTP, are also implicated in immune system function, and in particular T-cell function. Certain PTPases, notably TC-PTP, DEP-1, SAP-1, and CDC25, are also implicated in certain cancers. Certain PTPases, notably the bone PTPase OST-PTP, are implicated in osteoporosis. PTPases are implicated in mediating the actions of somatostatin on target cells, in particular the secretion of hormone and/or growth factor secretion.

Thus, there is a need for agents which inhibit the action of protein tyrosine phosphatases. Such agents would be useful for the treatment of Type I diabetes, Type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

SUMMARY OF THE INVENTION

This invention provides heteroaryl-fused nitrogen heterocycles which are useful as inhibitors of PTPases. The present invention provides compounds of Formula (I) as depicted below, methods of their preparation, pharmaceutical compositions comprising the compounds and to their use in treating human or animal disorders. The compounds of Formula (I) are useful as inhibitors of protein tyrosine phosphatases and thus are useful for the management, treatment, control and adjunct treatment of diseases mediated by PTPase activity. Such diseases include Type I diabetes, Type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

DETAILED DESCRIPTION OF THE INVENTION

In a first aspect, the present invention provides heteroaryl-fused nitrogen heterocycle inhibitors of protein tyrosine phosphatases (PTPases) which are potentially useful for the management and treatment of disease caused by PTPases.

In a second aspect, the present invention provides compounds of Formula (I):

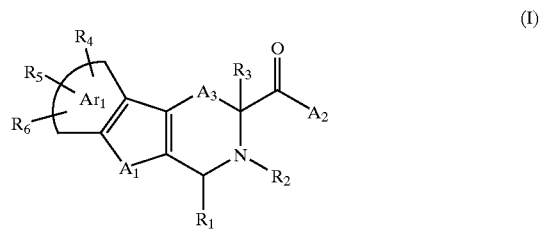

(I)

wherein
$R_1$ comprises
  (a) alkyl; alkenyl; alkynyl; aryl;
  (b) heterocyclyl; cycloalkyl;
  (c) heteroaryl;
  (d) -arylene-aryl; -arylene-heteroaryl; -heteroarylene-aryl; -heteroarylene-heteroaryl; -alkylene-aryl; -alkenylene-aryl;
  (e) -alkynylene-aryl; -alkyloxy-aryl; -alkylene-heteroaryl; -alkenylene-heteroaryl; -alkynylene-heteroaryl; -alkoxy-heteroaryl; -alkylene-heterocyclyl;
  (f) -alkylene-heterocyclyl; -alkenylene-heterocyclyl; -alkynylene-heterocyclyl; -alkylene-cycloalkyl, -alkenylene-cycloalkyl; -alkynylene-cycloalkyl; or
  (g) -arylene-$L_1$-alkylene-aryl; -arylene-$L_1$-alkylene-heteroaryl; -arylene-alkylene-$L_1$-heteroaryl; -arylene-alkylene-$L_1$-aryl; -alkylene-arylene-$L_1$-alkylene-aryl; -alkylene-arylene-$L_1$-alkylene-heteroaryl; -alkylene-arylene-alkylene-$L_1$-aryl; -alkylene-arylene-alkylene-$L_1$-heteroaryl;
wherein $L_1$ comprises O, —C(O)—, S, —S(O)—, —S(O$_2$)—, or a direct bond.
$R_2$ comprises
  (a) hydrogen;
  (b) alkyl; alkenyl; alkynyl;
  (c) heterocyclyl; cycloalkyl;

3

(d) -alkylene-aryl; -alkenylene-aryl; -alkynylene-aryl; -alkyloxy-aryl,
(e) -alkylene-heteroaryl; -alkenylene-heteroaryl; -alkynylene-heteroaryl; -alkoxy-heteroaryl;
(f) -alkylene-heterocyclyl; -alkenylene-heterocyclyl; -alkynylene-heterocyclyl; or
(g) —C(O)—OR$_7$; -alkylene-C(O)—OR$_7$; -alkenylene-C(O)—OR$_7$; -alkynylene-C(O)—OR$_7$, —C(O)—NR$_7$R$_8$; -alkylene-C(O)—NR$_7$R$_8$; -alkenylene-C(O)—NR$_7$R$_8$; -alkynylene-C(O)—NR$_7$R$_8$, -alkylene-O-aryl; -alkylene-O-alkylene-aryl; -alkylene-O-cycloalkyl; —(SO$_2$)—R$_7$; -alkylene-S(O$_2$)—R$_7$; -alkenylene-S(O$_2$)—R$_7$; -alkynylene-S(O$_2$)—R$_7$; -alkylene-S(O)—R$_7$; -alkenylene-S(O)—R$_7$; -alkynylene-S(O)—R$_7$; -alkylene-S(O$_2$)—R$_7$; -alkenylene-S(O$_2$)—R$_7$; -alkynylene-S(O$_2$)—R$_7$; —S(O$_2$)NR$_7$R$_8$; -alkylene-S(O$_2$)—NR$_7$R$_8$; -alkenylene-S(O$_2$)—NR$_7$R$_8$; or -alkynylene-S(O$_2$)—NR$_7$R$_8$; and wherein R$_7$ and R$_8$ independently comprise hydrogen, aryl, alkyl, or -alkylene-aryl; and wherein R$_7$ and R$_8$ may be taken together to form a ring having the formula —(CH$_2$)$_m$—T—(CH$_2$)$_n$— bonded to the nitrogen atom to which R$_7$ and R$_8$ are attached, wherein m and n are, independently, 1, 2, 3, or 4; T independently comprises —CH$_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N(R$_9$)—, —N(C(O)R$_9$)—, —N(C(O)NHR$_9$)—, —N(S(O$_2$)NHR$_9$)—, —N(SO$_2$R$_9$)—, or —N(C(O)OR$_9$)—; or R$_7$ and R$_8$ may be taken together, with the nitrogen atom to which they are attached, to form a heterocyclyl or heteroaryl ring.

R$_3$ comprises
(a) hydrogen;
(b) alkyl; alkenyl; alkynyl;
(c) -alkylene-aryl; -alkenylene-aryl; -alkynylene-aryl; or
(d) -alkylene-heteroaryl; -alkenylene-heteroaryl; -alkynylene-heteroaryl.

A$_2$ comprises —O—R$_{10}$, —NR$_{10}$R$_{11}$, or —NR$_{10}$A$_4$:
where
R$_{10}$ and R$_{11}$ independently comprise:
(a) hydrogen;
(b) alkyl; alkenyl; alkynyl;
(c) heterocyclyl; cycloalkyl;
(d) aryl; heteroaryl; -arylene-aryl; -arylene-heteroaryl; -heteroarylene-aryl; -heteroarylene-heteroaryl; -alkylene-aryl; -alkenylene-aryl; -alkynylene-aryl; -alkyloxy-aryl; -alkylene-heteroaryl, -alkenylene-heteroaryl, -alkynylene-heteroaryl, -alkoxy-heteroaryl,
(e) -alkylene-heterocyclyl; -alkenylene-heterocyclyl; -alkynylene-heterocyclyl;
(f) -arylene-L$_2$-alkylene-aryl, -arylene-L$_2$-alkylene-heteroaryl, -arylene-alkylene-L$_2$-heteroaryl, -arylene-alkylene-L$_2$-aryl, -arylene-arylene-L$_2$-alkylene-aryl, -alkylene-L$_2$-aryl, -alkylene-L$_2$-arylene-aryl, -alkylene-arylene-L$_2$-alkylene-C(O)O-alkyl, -alkylene-arylene-L$_2$-alkylene-C(O)OH, -alkylene-arylene-L$_2$-alkylene-C(O)NH-alkyl, -alkylene-arylene-L$_2$-alkylene-heteroaryl, -alkylene-arylene-alkylene-L$_2$-aryl, -alkylene-arylene-alkylene-L$_2$-heteroaryl;
wherein L$_2$ is O, —C(O)—, S, —S(O)—, —S(O$_2$)—, or a direct bond; or

4

(g) —C(O)—OR$_{12}$, -alkylene-C(O)—OR$_{12}$, -alkenylene-C(O)—OR$_{12}$, -alkynylene-C(O)—OR$_{12}$, —C(O)—NR$_{12}$R$_{13}$, -alkylene-C(O)—NR$_{12}$R$_{13}$, -alkenylene-C(O)—NR$_{12}$R$_{13}$, alkynylene-C(O)—NR$_{12}$R$_{13}$, -alkylene-O-aryl, -alkylene-O-alkylene-aryl, -alkylene-O-cycloalkyl, —S(O$_2$)—R$_{12}$, -alkylene-S(O$_2$)—R$_{12}$, -alkenylene-S(O$_2$)—R$_{12}$, -alkynylene-S(O$_2$)—R$_{12}$, -alkylene-S(O)—R$_{12}$, -alkenylene-S(O)—R$_{12}$, -alkynylene-S(O)—R$_{12}$, -alkylene-S(O)—R$_{12}$, -alkenylene-S(O)—R$_{12}$, -alkynylene-S(O)—R$_{12}$, —S(O$_2$)—NR$_{12}$R$_{13}$, -alkylene-S(O$_2$)—NR$_{12}$R$_{13}$, -alkenylene-S(O$_2$)—NR$_{12}$R$_{13}$, and -alkynylene-S(O$_2$)—NR$_{12}$R$_{13}$;

where R$_{10}$ and R$_{11}$ may be taken together with the nitrogen atom to which they are attached, to form a heterocycyl or heteroaryl ring;

and wherein R$_{12}$ and R$_{13}$ independently comprise hydrogen, aryl, alkyl, or alkylene-aryl; and wherein R$_{12}$ and R$_{13}$ may be taken together to form a ring having the formula —(CH$_2$)$_s$—V—(CH$_2$)$_t$— bonded to the nitrogen atom to which R$_{12}$ and R$_{13}$ are attached, and wherein s and t are, independently, selected from the group consisting of 1, 2, 3, or 4; V comprises —CH$_2$—, —C(O)—, —O—, —N(H)—, —S—, —S(O)—, —S(O$_2$)—, —CON(H)—, —NHC(O)—, —NHC(O)N(H)—, —NHS(O$_2$), —S(O$_2$)N(H)—, —(O)CO—, —NHS(O$_2$)NH—, —OC(O)—, —N(R$_{14}$)—, —N(C(O)R$_{14}$)—, —N(C(O)NHR$_{14}$)—, —N(SO$_2$NHR$_{14}$)—, —N(S(O$_2$)R$_{14}$)—, or —N(C(O)OR$_{14}$)—.

R$_{12}$ and R$_{13}$ with the nitrogen atom to which they are attached, form a heterocyclyl or heteroaryl ring.

A$_4$ comprises

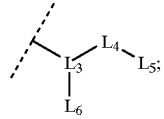

wherein
L$_3$ comprises a alkyline, alkenyline, heteroaryline, aryline, cycloalkyline, or heterocyclyline group;
L$_4$ comprises a direct bond, —C(O)—N(R$_{15}$)—, —C(O)—O—, —C(O)—, or —N(R$_{15}$)—CO—N(R$_{16}$)—, -alkylene-C(O)—N(R$_{15}$)—, -alkylene-C(O)—O—, -alkylene-C(O)—, or —alkylene-N(R$_{15}$)—CO—N(R$_{16}$)—;
L$_5$ comprises H, alkyl, alkenyl, alkynyl, heterocyclyl, heteroaryl, alkylene-aryl;
L$_6$ comprises hydrogen, alkyl, alkenyl, alkynyl, -alkylene-aryl, -alkylene-heteroaryl, -alkylene-O-alkylene-aryl, -alkylene-arylene-O-alkylene-aryl, -alkylene-S-alkylene-aryl, -alkylene-O-alkyl, -alkylene-S-alkyl, -alkylene-NH$_2$, -alkylene-OH, -alkylene-SH, alkylene-cycloalkyl, alkylene-heterocyclyl, cycloalkyl, heterocyclyl, alkylene-arylene-aryl, arylene-aryl, -alkylene-C(O)—OR$_{17}$, -alkylene-C(O)—NR$_{17}$R$_{18}$, -alkylene-NR$_{17}$R$_{18}$, -alkylene-N(R$_{17}$)—C(O)—R$_{18}$, or -alkylene-N(R$_{17}$)—S(O$_2$)—R$_{18}$;
R$_{17}$ and R$_{18}$ independently comprise hydrogen, aryl, alkyl, or alkylene-aryl; and wherein
R$_{17}$ and R$_{18}$ may be taken together to form a ring having the formula —(CH$_2$)$_o$—P—(CH$_2$)$_w$— bonded to the nitrogen atom to which $R_{17}$ and $R_{18}$ are attached, and wherein o and w are, independently, selected from the group consisting of 1, 2, 3, or 4; P comprises —$CH_2$—, —C(O)—, —O—, —N(H)—, —S—, —S(O)—, —S($O_2$)—, —CON(H)—, —NHC(O)—, —NHC(O)N(H)—, —NHS($O_2$), —S($O_2$)N(H)—, —(O)CO—, —NHS($O_2$)NH—, —OC(O)—, —N($R_{19}$)—, —N(C(O)$R_{19}$)—, —N(C(O)NH$R_{19}$)—, —N($SO_2$NH$R_{19}$)—, —N(S($O_2$)$R_{19}$)—, or —N(C(O)O$R_{19}$)—; or $R_{17}$ and $R_{18}$ may be taken together with the nitrogen atom to which they are attached to form a heterocyclyl or heteroaryl ring.

$R_9$, $R_{14}$, $R_{15}$, $R_{18}$, and $R_{19}$ independently comprise hydrogen, aryl, alkyl, or alkylene-aryl;

$A_1$ comprises O; S; or $NR_{20}$, where $R_{20}$ comprises:

(a) hydrogen;

(b) alkyl;

(c) alkenyl; alkynyl; heterocyclyl; cycloalkyl; -alkylene-aryl; -alkenylene-aryl; -alkynylene-aryl; -alkyloxy-aryl; -alkylene-heteroaryl; -alkenylene-heteroaryl; -alkynylene-heteroaryl; -alkoxy-heteroaryl; -alkylene-heterocyclyl; -alkenylene-heterocyclyl; -alkynylene-heterocyclyl; or (d) -alkylene-C(O)—$OR_{21}$; -alkenylene-C(O)—$OR_{21}$; -alkynylene-C(O)—$OR_{21}$; —C(O)—$NR_{21}R_{22}$; -alkylene-C(O)—$NR_{21}R_{22}$; -alkenylene-C(O)—$NR_{21}R_{22}$; -alkynylene-C(O)—$NR_{21}R_{22}$; -alkylene-O-aryl; -alkylene-O-alkylene-aryl; -alkylene-O-cycloalkyl; —S($O_2$)—$R_{21}$; -alkylene-S($O_2$)—$R_{21}$; -alkenylene-S($O_2$)—$R_{21}$; -alkynylene-S($O_2$)—$R_{21}$; -alkylene-S(O)—$R_{21}$; -alkenylene-S(O)—$R_{21}$; -alkynylene-S(O)—$R_{21}$; alkylene-S(O)—$R_{21}$; -alkenylene-S(O)—$R_{21}$; -alkynylene-S(O)—$R_{21}$; —S($O_2$)—$NR_{21}R_{22}$; -alkylene-S($O_2$)—$NR_{21}R_{22}$; -alkenylene-S($O_2$)—$NR_{21}R_{22}$; -alkynylene-S($O_2$)—$NR_{21}R_{22}$; and wherein $R_{21}$ and $R_{22}$ independently comprise hydrogen, aryl, alkyl, or alkylene-aryl; and wherein $R_{21}$ and $R_{22}$ may be taken together to form a ring having the formula —$(CH_2)_x$—Z—$(CH_2)_y$— bonded to the nitrogen atom to which $R_{14}$ and $R_{15}$ are attached;

x and y are, independently, 1, 2, 3, or 4; Z comprises —$CH_2$—, —C(O)—, —O—, —N(H)—, —S—, —S(O)—, —S($O_2$)—, —C(O)N(H)—, —NHC(O)—, —NHC(O)N(H)—, —NHS($O_2$)—, —S($O_2$)N(H)—, —(O)CO—, —NHS($O_2$)H—, —OC(O)—, —N($R_{23}$)—, —N(C(O)$R_{23}$)—, —N(C(O)NH$R_{23}$)—, —N(S($O_2$)NH$R_{23}$)—, —N(S($O_2$)$R_{23}$)—, or —N(C(O)O$R_{23}$)—; or $R_{21}$ and $R_{22}$ may be taken together, with the nitrogen atom to which they are attached, to form a heterocyclyl or heteroaryl ring.

$A_3$ comprises a direct bond; —$CH_2$— or $CH_2$—$CH_2$—.

$Ar_1$ is, taken together with the double bond in Formula (I), aryl or heteroaryl.

$R_4$, $R_5$, and $R_6$ independently comprise (a) hydrogen;

(b) aryl, heteroaryl;

(c) heterocyclyl; cycloalkyl; or (d) -alkylene-Y-aryl; -alkenylene-Y-aryl; -alkynylene-Y-aryl; -alkylene-Y-heterocyclyl; -alkenylene-Y-heterocyclyl; -alkynlene-Y-heterocyclyl; -alkylene-Y-cycloalkyl; -alkenylene-Y-cycloalkyl; -alkynlene-Y-cycloalkyl; -alkylene-Y-heterocyclyl; -alkenylene-Y-heterocyclyl; -alkynlene-Y-heterocyclyl; —Y—H; —Y-alkyl; —Y-aryl; —Y-alkylene-aryl; —Y-alkylene-$NR_{24}R_{25}$; —Y—O—Si-(alkyl)$_3$; and —Y—O—Si-(alkylene-aryl)$_3$;

wherein

Y comprises —$CH_2$—, —O—, —N(H)—, —S—, —S(O)—, —S($O_2$)—, —C(O)N(H)—, —NHC(O)—, —NHC(O)N(H)—, —NHS($O_2$), —S($O_2$)N(H)—, —C(O)—O—, —C(NH)—O—, —NHS($O_2$)H—, or —O—C(O)—;

$R_{24}$ and $R_{25}$ independently comprise hydrogen, aryl, alkyl, or alkylene-aryl; and wherein $R_{24}$ and $R_{25}$ may be taken together to form a ring having the formula —$(CH_2)_q$—Q—$(CH_2)_r$— bonded to the nitrogen atom to which $R_{24}$ and $R_{25}$ are attached, wherein q and r are, independently, 1, 2, 3, or 4; Q is —$CH_2$—, —O—, —N(H)—, —S—, —S(O)—, —S($O_2$), —CON(H)—, —NHC(O)—, —NHC(O)N(H)—, —NHS-($O_2$)—, —S($O_2$)N(H)—, —(O)CO—, —NHS($O_2$)H—, —OC(O)—, —N($R_{26}$)—, —N(C(O)$R_{26}$)—, —N(C(O)NH$R_{26}$)—, —N(S($O_2$)NH$R_{26}$)—, —N(S($O_2$)$R_{26}$)—, or —N(C(O)O$R_{26}$)—; or $R_{24}$ and $R_{25}$ may be taken together, with the nitrogen atom to which they are attached, to form a heterocyclyl or heteroaryl ring.

$R_{23}$ and $R_{26}$ independently comprise hydrogen, aryl, alkyl, or alkylene-aryl.

The compound of Formula (I) may comprise a pharmaceutically acceptable salt, solvate or prodrug thereof.

In a preferred embodiment of the compound of Formula (I), $R_1$ comprises: 1,1'-biphenyl-4-yl; cyclohexyl; 4-bromo, chloro, or fluorophenyl; 2,4-dichlorophenyl; 4-benzyloxyphenyl; 4-(4-carboxy)benzyloxyphenyl, cyclopentyl; (E)-2-phenylvinylphenyl; indol-3-yl; 4-hydroxyphenyl; 4-hydroxybenzyl)methyl; 1-benzylindol-3-yl; or 1-butylindol-3-yl.

In another preferred embodiment of the compound of Formula (I), $A_3$ comprises a methylene group.

In another preferred embodiment of the compound of Formula (I), $R_4$, $R_5$, and $R_6$ comprise hydrogen, alkyl, carboxy, and alkylcarbamoyl.

In another preferred embodiment of the compound of Formula (I), $A_1$ comprises a $NR_{20}$, wherein $R_{20}$ comprise hydrogen, or alkyl.

In another preferred embodiment of the compound of Formula (I), $Ar_1$ comprises an aryl group.

In another preferred embodiment of the compound of Formula (I), $R_2$ comprises a hydrogen or an alkyloxycarbonyl group.

In another preferred embodiment of the compound of Formula (I), $A_2$ comprises —O—$R_{10}$, —$NR_{10}R_{11}$, or —$NR_{10}A_4$, wherein $R_{10}$ and $R_{11}$ independently comprise hydrogen; alkyl; heterocyclyl, or cycloalkyl; and $A_4$ comprises benzyl; 3-Fluorophenyl; 2-(3-Fluorophenyl)-1-ethyl; 1,1'-Biphenyl-4-yl; 1-Benzylcarbamoyl-1-(1,1'-Biphenyl-4-yl)methyl; 2,4,6-Trimethoxybenzyl; 4-tert-Butylbenzyl; (5-methyl-2-furan)methyl; 4-Chlorobenzyl; 4-Carboxybenzyl; 2,4,6-Trimethoxybenzyl; 4-(methoxycarbonylmethoxy)-1-phenyl; 4-(Carboxymethyl)-1-phenyl; 4-Methoxycarbonyl-1-cyclohexyl; 2(4-(methoxycarbonylmethoxy)-phenyl-1-ethyl; (5-Methyl-2-furan)methyl; 2,4,6-Trimethoxybenzyl; 1-Methoxycarbonyl-1-(1,1'-Biphenyl-4-yl)methyl; (R)-1-Methoxycarbonyl-1-(4-hydroxyphenyl)methyl; 1-(1,1'-

Biphenyl-4-yl)1-carboxymethyl; 1-(1,1'-Biphenyl-4-yl)1-carboxymethyl; (R)-1-Methoxycarbonyl-1-(4-hydroxybenzyl)methyl; 1-Methoxycarbonyl-1-(1,1'-Biphenyl-4-yl)methyl; 1-Methoxycarbonyl-1-(1,1'-Biphenyl-4-yl)methyl; 1-Methylcarbamoyl-1-(1,1'-Biphenyl-4-yl)methyl; 2-[4-(benzyloxy)phenyl]-1-carboxy-1-ethyl; 1-Dimethylaminocarbamoyl-1-(1,1'-Biphenyl-4-yl)methyl; 1-Hydroxymethyl-1-(1,1'-Biphenyl-4-yl)methyl; 2-(1,1'-Biphenyl-4-yl)1-methoxycarbonyl-1-ethyl; 2-(1,1'-Biphenyl-4-yl)1-methoxycarbonyl-1-ethyl; 1-Benzyloxycarbonyl-1-1,1'-Biphenyl-4-yl)methyl; 1-Methoxycarbonyl-1-(1,1'-Biphenyl-4-yl)methyl; 1-Benzyloxycarbonyl-1-(1,1'-Biphenyl-4-yl)methyl; 1-Propoxycarbonyl-1-(1,1'-Biphenyl-4-yl)methyl; 1-Butoxycarbonyl-1-(1,1'-Biphenyl-4-yl)methyl; 1-(2-Methoxy-1-ethoxycarbonyl)-1-(1,1'-Biphenyl-4-yl)methyl; 1-Methoxymethyl-1-(1,1'-Biphenyl-4-yl)methyl; 1-Methoxymethyl-1-(1,1'-Biphenyl-4-yl)methyl; Benzothiazol-2-yl; 1-(2-Hydroxy-1-propylcarbamoyl-1-(1,1'-Biphenyl-4-yl)methyl; or 1-(2-Oxo-1-propylcarbamoyl-1-(1,1'-Biphenyl-4-yl)methyl.

In a more preferred embodiment of the compound of Formula (I), $R_1$ comprises: 1,1'-biphenyl-4-yl; cyclohexyl; 4-bromo, chloro, or fluorophenyl; 2,4-dichlorophenyl; 4-benzyloxyphenyl; 4-(carboxy)benzyloxyphenyl, cyclopentyl; (E)-2-phenylvinylphenyl; indol-3-yl; 4-hydroxyphenyl; 4-hydroxybenzyl)methyl; 1-benzylindol-3-yl; or 1-butylindol-3-yl; $A_3$ comprises a methylene group; $R_4$, $R_5$, and $R_6$ comprise hydrogen, alkyl, carboxy, and alkylcarbamoyl; $A_1$ comprises a $NR_{20}$, wherein $R_{20}$ comprise hydrogen, or alkyl; $Ar_1$ comprises an aryl group; $R_2$ comprises a hydrogen or an alkyloxycarbonyl group; and $A_2$ comprises —O—$R_{10}$, —$NR_{10}R_{11}$, or —$NR_{10}A_4$, wherein $R_{10}$ and $R_{11}$ independently comprise hydrogen; alkyl; heterocyclyl; or cycloalkyl; and $A_4$ comprises benzyl; 3-Fluorophenyl; 2-(3-Fluorophenyl)-1-ethyl; 1,1'-Biphenyl-4-yl; 1-Benzylcarbamoyl-1-(1,1'-Biphenyl-4-yl)methyl; 2,4,6-Trimethoxybenzyl; 4-tert-Butylbenzyl; (5-methyl-2-furan)methyl; 4-Chlorobenzyl; 4-Carboxybenzyl; 2,4,6-Trimethoxybenzyl; 4-(methoxycarbonylmethyl)-1-phenyl; 4-(Carboxymethyl)-1-phenyl; 4-Methoxycarbonyl-1-cyclohexyl; 2(4-(methoxycarbonylmethoxy)-phenyl-1-ethyl; (5-Methyl-2-furan)methyl; 2,4,6-Trimethoxybenzyl; 1-Methoxycarbonyl-1-(1,1'-Biphenyl-4-yl)methyl; (R)-1-Methoxycarbonyl-1-(4-hydroxyphenyl)methyl; 1-(1,1'-Biphenyl-4-yl)1-carboxymethyl; 1-(1,1'-Biphenyl-4-yl)1-carboxymethyl; (R)-1-Methoxycarbonyl-1-(4-hydroxybenzyl)methyl; 1-Methoxycarbonyl-1-(1,1'-Biphenyl-4-yl)methyl; 1-Methoxycarbonyl-1-(1,1'-Biphenyl-4-yl)methyl; 1-Methylcarbamoyl-1-(1,1'-Biphenyl-4-yl)methyl; 2-[4-(benzyloxy)phenyl]-1-carboxy-1-ethyl; 1-Dimethylaminocarbamoyl-1-(1,1'-Biphenyl-4-yl)methyl; 1-Hydroxymethyl-1-(1,1'-Biphenyl-4-yl)methyl; 2-(1,1'-Biphenyl-4-yl)1-methoxycarbonyl-1-ethyl; 2-(1,1'-Biphenyl-4-yl)1-methoxycarbonyl-1-ethyl; 1-Benzyloxycarbonyl-1-(1,1'-Biphenyl-4-yl)methyl; 1-Methoxycarbonyl-1-(1,1'-Biphenyl-4-yl)methyl; 1-Benzyloxycarbonyl-1-(1,1'-Biphenyl-4-yl)methyl; 1-Propoxycarbonyl-1-(1,1'-Biphenyl-4-yl)methyl; 1-Butoxycarbonyl-1-(1,1'-Biphenyl-4-yl)methyl; 1-(2-Methoxy-1-ethoxycarbonyl)-1-(1,1'-Biphenyl-4-yl)methyl; 1-Methoxymethyl-1-(1,1'-Biphenyl-4-yl)methyl; 1-Methoxymethyl-1-(1,1'-Biphenyl-4-yl)methyl; Benzothiazol-2-yl; 1-(2-Hydroxy-1-propylcarbamoyl-1-(1,1'-Biphenyl-4-yl)methyl; or 1-(2-Oxo-1-propylcarbamoyl-1-(1,1'-Biphenyl-4-yl)methyl.

Compounds of Formula (I) that are currently preferred for their biological activity are listed by name below in Table 1.

The compounds of Formula (I) are potentially useful in treating metabolic disorders related to insulin resistance or hyperglycemia, typically associated with obesity or glucose intolerance. The compounds of Formula (I), therefore, should prove particularly useful in the treatment or inhibition of type II diabetes. The compounds of Formula (I) are also potentially useful in modulating glucose levels in disorders such as type I diabetes.

The potential ability of compounds of Formula (I) to treat or inhibit disorders related to insulin resistance or hyperglycemia was established with representative compounds of this invention in the following standard primary/secondary assay test procedure which measures the inhibition of PTP-1B activity.

TABLE 1

| Example | Structure | Name |
| --- | --- | --- |
| 1 | 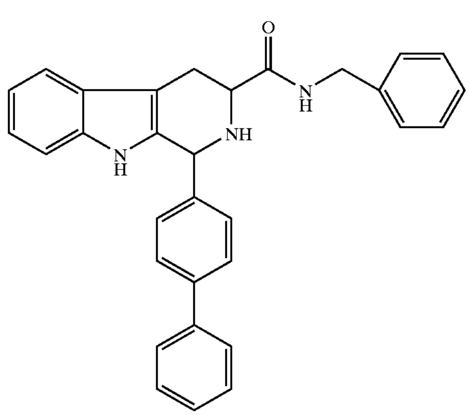 | Benzyl 1-(1,1'-biphenyl-4-yl)-1,2,3,4-tetrahydro-beta-carboline-3-carboxamide |

TABLE 1-continued

| Example | Structure | Name |
|---|---|---|
| 2 | 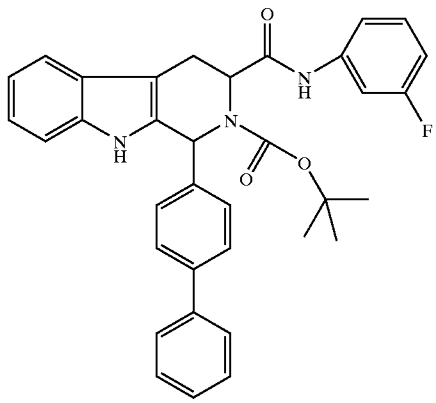 | 3-Fluorophenyl 1-(1,1'-biphenyl-4-yl)-2-tert-butoxycarbonyl-1,2,3,4-tetrahydro-beta-carboline-3-carboxamide |
| 3 | 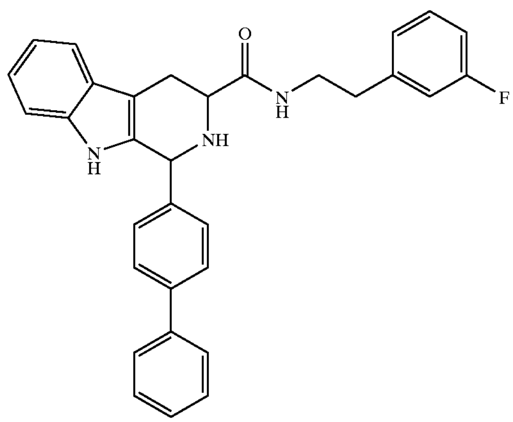 | 2-(3-Fluorophenyl)-1-ethyl 1-(1,1'-Biphenyl-4-yl)-1,2,3,4-tetrahydro-beta-carboline-3-carboxamide |
| 4 | 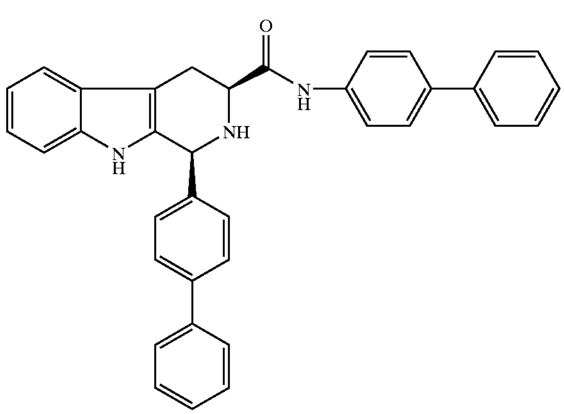 | 1,1'-Biphenyl-4-yl(1S, 3S)-1-(1,1'-Biphenyl-4-yl)-1,2,3,4-tetrahydro-beta-carboline-3-carboxamide |

TABLE 1-continued

| Example | Structure | Name |
|---|---|---|
| 5 | 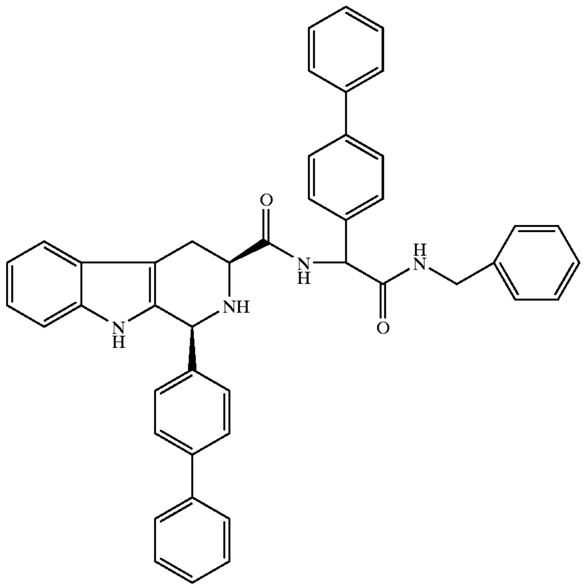 | 1-Benzylcarbamoyl-1-(1,1'-Biphenyl-4-yl)methyl(1S, 3S)-1-(1,1'-Biphenyl-4-yl)-1,2,3,4-tetrahydro-beta-carboline-3-carboxamide |
| 6 | 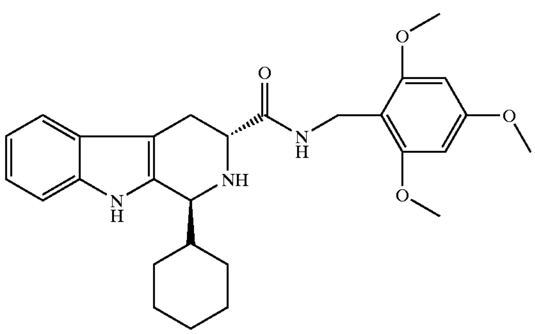 | 2,4,6-Trimethoxybenzyl(1S, 3R)-1-Cyclohexyl-1,2,3,4-tetrahydro-beta-carboline-3-carboxamide |
| 7 | 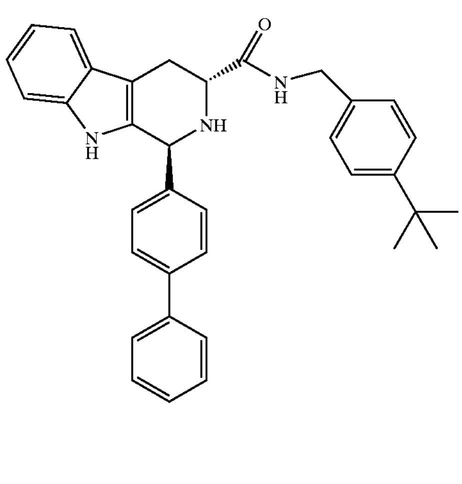 | 4-tert-Butylbenzyl(1S, 3R)-1-(1,1'-Biphenyl-4-yl)-1,2,3,4-tetrahydro-beta-carbolifle-3-Carboxamide |

TABLE 1-continued

| Example | Structure | Name |
| --- | --- | --- |
| 8 | 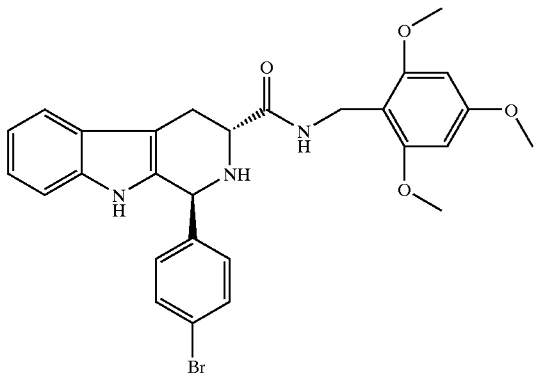 | 2,4,6-Trimethoxybenzyl(1S, 3R)-1-(4-bromophenyl)-1,2,3,4-tetrahydro-beta-carboline-3-carboxamide |
| 9 | 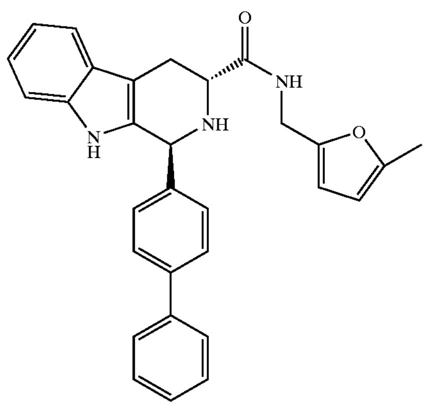 | (5-methyl-2-furan)methyl (1S, 3R)-1-(1,1'-Biphenyl-4-yl)-1,2,3,4-tetrahydro-beta-carboline-3-carboxamide |
| 10 | 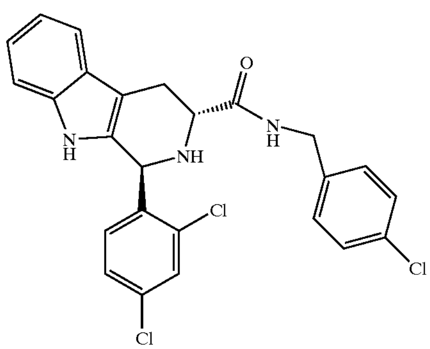 | 4-Chlorobenzyl(1S, 3R)-1-(2,4-dichlorophenyl)-1,2,3,4-tetrahydro-beta-carboline-3-carboxamide |
| 11 | 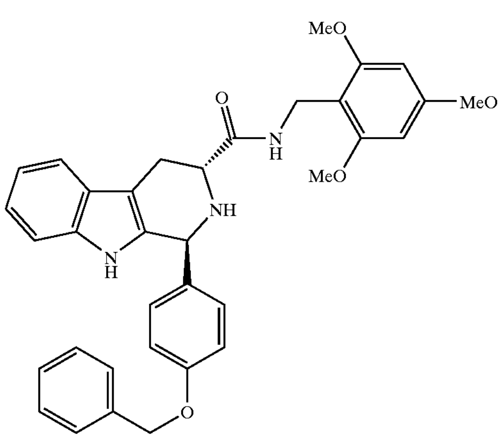 | 2,4,6-Trimethoxybenzyl(1S, 3R)-1-(4-benzyloxyphenyl)-1,2,3,4-tetrahydro-beta-carboline-3-carboxamide |

TABLE 1-continued

| Example | Structure | Name |
|---|---|---|
| 12 | 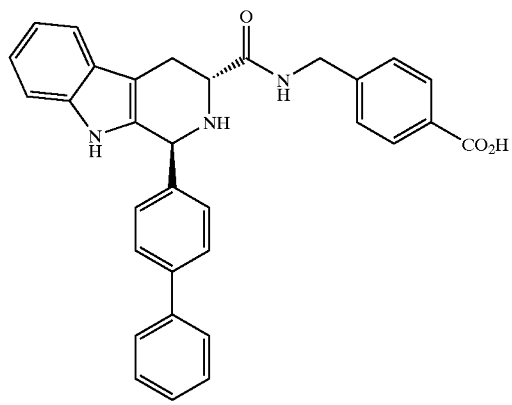 | 4-Carboxybenzyl(1S, 3R)-1-(1,1'-Biphenyl-4-yl)-1,2,3,4-tetrahydro-beta-carboline-3-carboxamide |
| 13 | 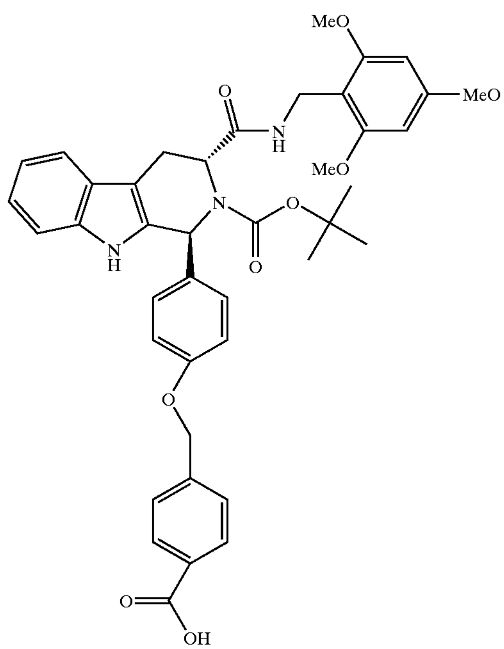 | 2,4,6-Trimethoxybenzyl(1S, 3R)-1-(4-(4-carboxy)benzyloxyphenyl)-2-tert-butoxycarbonyl-1,2,3,4-tetrahydro-beta-carboline-3-carboxamide |
| 14 | 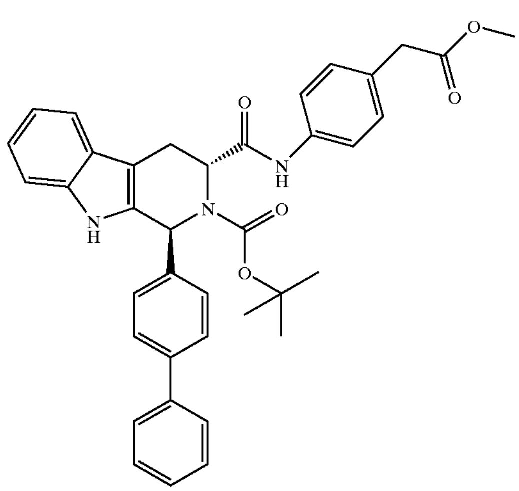 | 4-(methoxycarbonylmethyl)-1-phenyl(1S, 3R)-1-(1,1'-Biphenyl-4-yl)-2-tert-butoxycarbonyl-1,2,3,4-tetrahydro-beta-carboline-3-carboxamide |

TABLE 1-continued

| Example | Structure | Name |
|---|---|---|
| 15 | 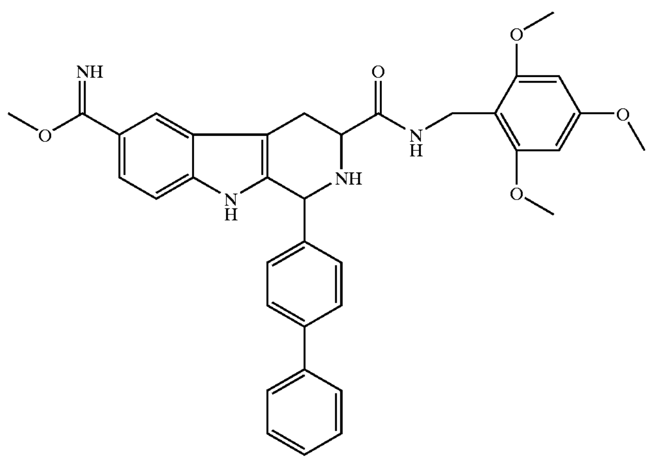 | 2,4,6-Trimethoxybenzyl 1-(1,1'-Biphenyl-4-yl)-6-methylcarboximidatoyl-1,2,3,4-tetrahydro-beta-carboline-3-carboxamide |
| 16 | 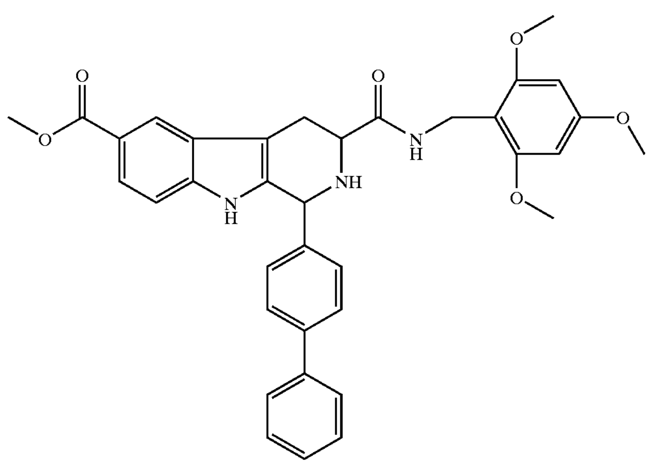 | 2,4,6-Trimethoxybenzyl 1-(1,1'-Biphenyl-4-yl)-6-methoxycarbonyl-1,2,3,4-tetrahydro-beta-carboline-3-carboxamide |
| 17 | 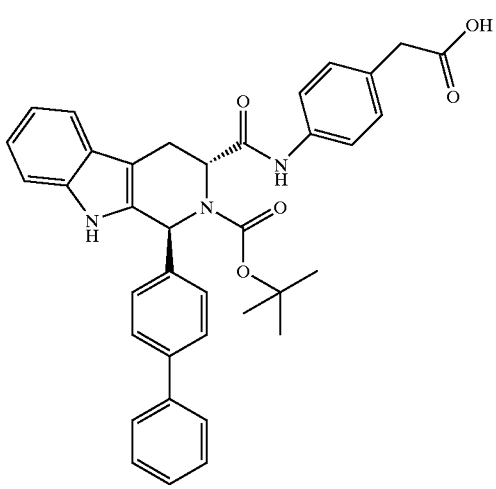 | 4-(Carboxymethyl)-1-phenyl (1S, 3R)-1-(1,1'-Biphenyl-4-yl)-2-tert-butoxycarbonyl-1,2,3,4-tetrahydro-beta-carboline-3-carboxamide |

TABLE 1-continued

| Example | Structure | Name |
|---|---|---|
| 18 | 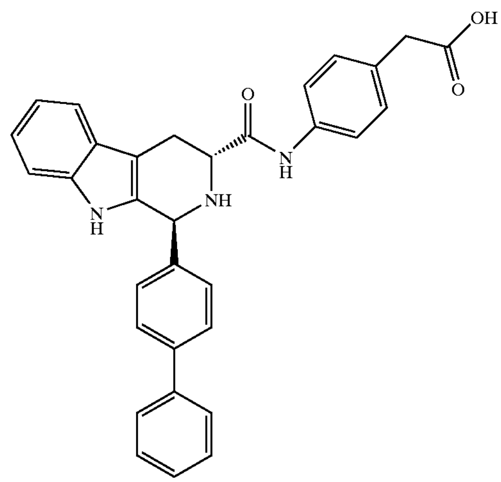 | 4-(Carboxymethyl)-1-phenyl (1S, 3R)-1-(1,1'-Biphenyl-4-yl)-1,2,3,4-tetrahydro-beta-carboline-3-carboxamide |
| 19 | 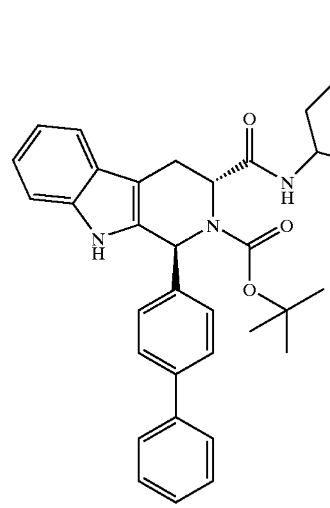 | 4-Methoxycarbonyl-1-cyclohexyl (1S, 3R)-1-(1,1'-Biphenyl-4-yl)-2-tert-butoxycarbonyl-1,2,3,4-tetrahydro-beta-carboline-3-carboxamide |
| 20 | 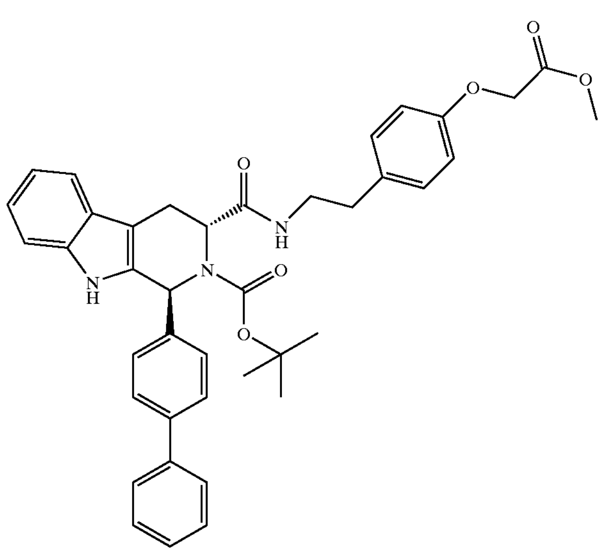 | 2(4-(methoxycarbonylmethoxy)-phenyl-1-ethyl(1S, 3R)-1-(1,1'-Biphenyl-4-yl)-2-tert-butoxycarbonyl-1,2,3,4-tetrahydro-beta-carboline-3-carboxamide |

TABLE 1-continued
| Example | Structure | Name |
|---|---|---|
| 21 | 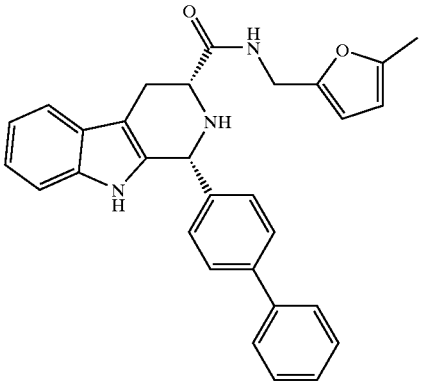 | (5-Methyl-2-furan)methyl(1R, 3S)-1-(1,1'-Biphenyl-4-yl)-1,2,3,4-tetrahydro-beta-carboline-3-carboxamide |
| 22 | 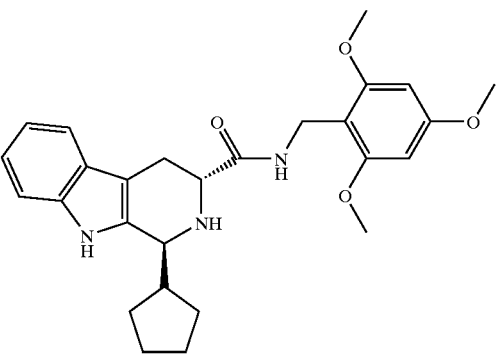 | 2,4,6-Trimethoxybenzyl 1-Cyclopentyl-1,2,3,4-tetrahydro-beta-carboline-3-carboxamide |
| 23 | 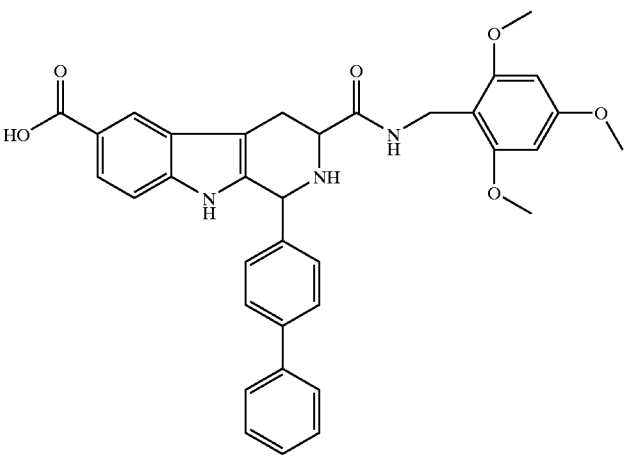 | 2,4,6-Trimethoxybenzyl 1-(1,1'-Biphenyl-4-yl)-6-carboxy-1,2,3,4-tetrahydro-beta-carboline-3-carboxamide |

TABLE 1-continued

| Example | Structure | Name |
| --- | --- | --- |
| 24 | 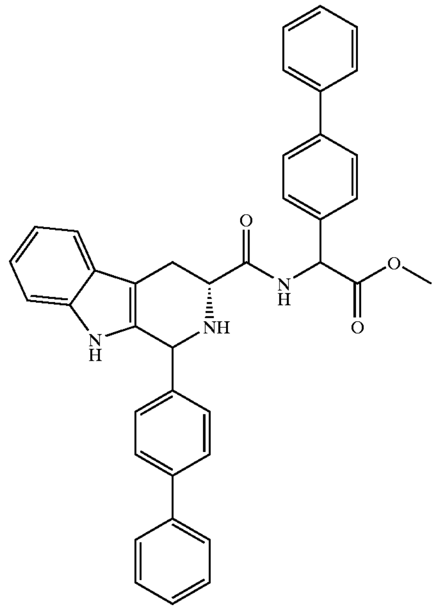 | 1-Methoxycarbonyl-1-(1,1'-Biphenyl-4-yl)methyl(3R)-1-(1,1'-Biphenyl-4-yl)-1,2,3,4-tetrahydro-beta-carboline-3-carboxamide |
| 25 | 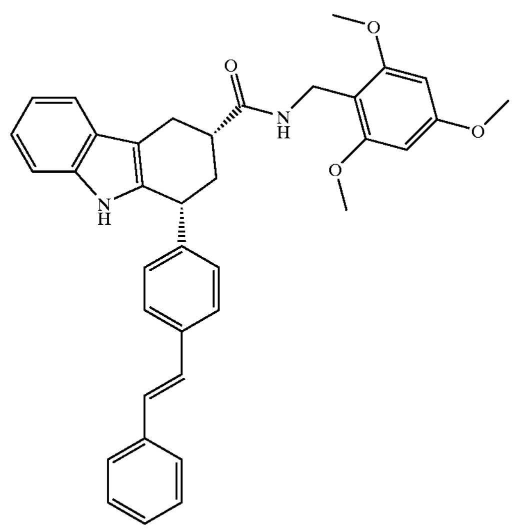 | 2,4,6-Trimethoxybenzyl(1R, 3R)-1-{4-[(E)-2-phenylvinyl]phenyl}-1,2,3,4-tetrahydro-beta-carboline-3-carboxamide |

TABLE 1-continued

| Example | Structure | Name |
|---|---|---|
| 26 | 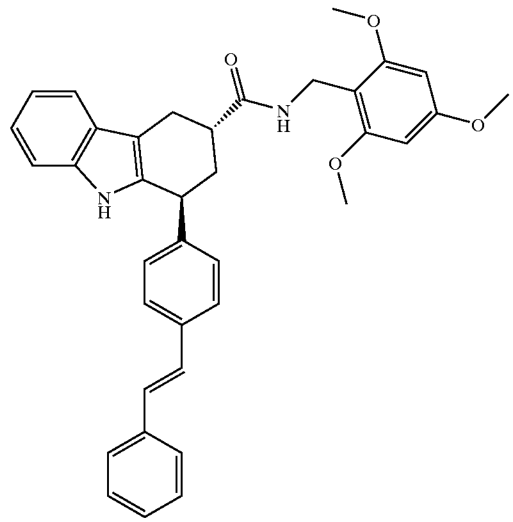 | 2,4,6-Trimethoxybenzyl(1S, 3R)-1-{4-[(E)-2-phenylvinyl]phenyl}-1,2,3,4-tetrahydro-beta-carboline-3-carboxamide |
| 27 | 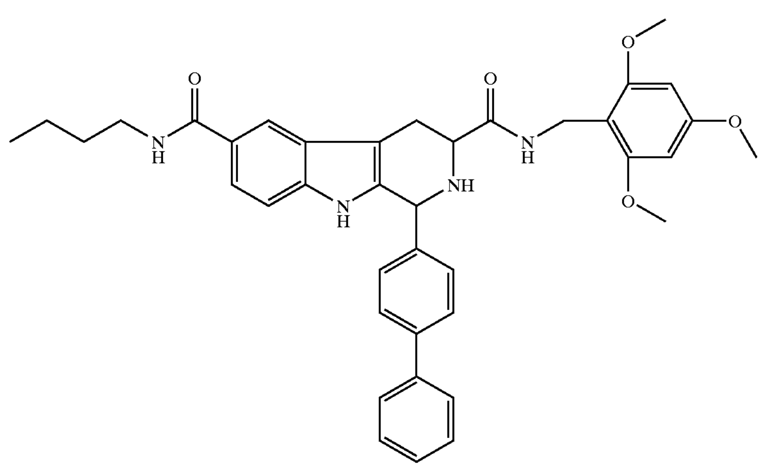 | 2,4,6-Trimethoxybenzyl 1-(1,1'-Biphenyl-4-yl)-6-butylcarbamoyl-1,2,3,4-tetrahydro-beta-carboline-3-carboxamide |
| 28 | 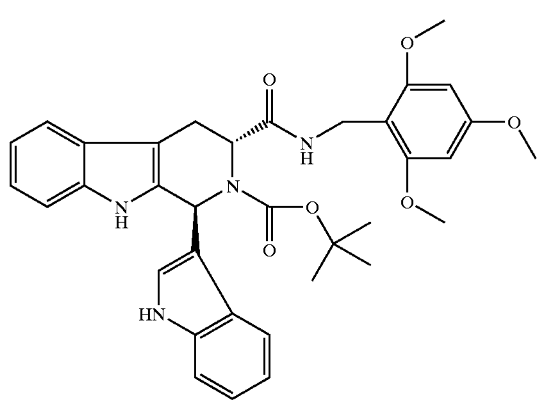 | 2,4,6-Trimethoxybenzyl(1S, 3R)-1-(Indol-3-yl)-2-tert-butoxycarbonyl-1,2,3,4-tetrahydro-beta-carboline-3-carboxamide |

TABLE 1-continued

| Example | Structure | Name |
|---|---|---|
| 29 | 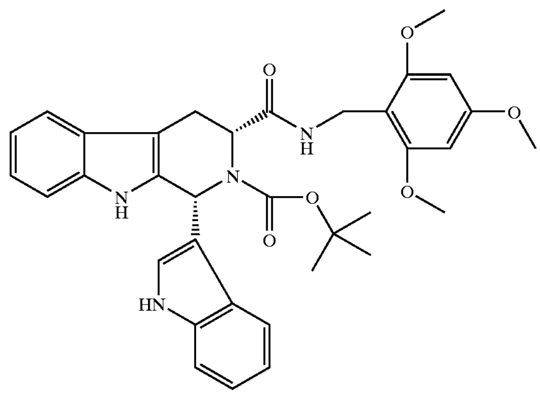 | 2,4,6-Trimethoxybenzyl(1R, 3R)-1-(Indol-3-yl)-2-tert-butoxycarbonyl-1,2,3,4-tetrahydro-beta-carboline-3-carboxamide |
| 30 | 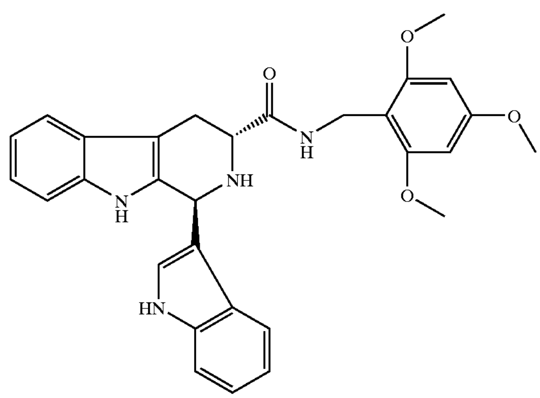 | 2,4,6-Trimethoxybenzyl(1S, 3R)-1-(Indol-3-yl)-1,2,3,4-tetrahydro-beta-carboline-3-carboxamide |
| 31 | 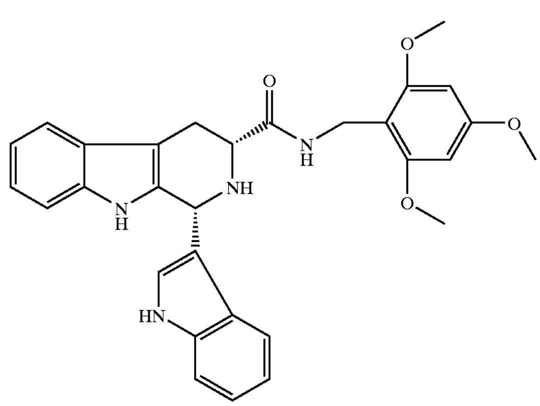 | 2,4,6-Trimethoxybenzyl(1R, 3R)-1-(Indol-3-yl)-1,2,3,4-tetrahydro-beta-carboline-3-carboxamide |

TABLE 1-continued

| Example | Structure | Name |
|---|---|---|
| 32 | 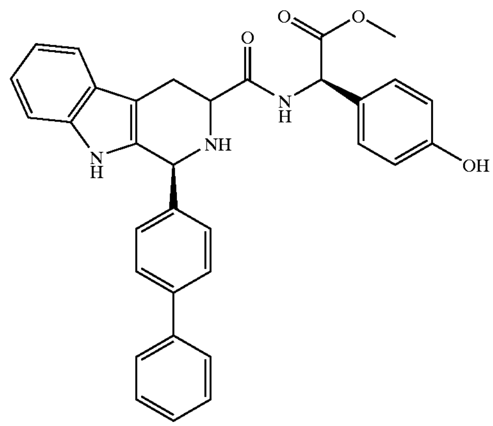 | (R)-1-Methoxycarbonyl-1-(4-hydroxyphenyl)methyl(1S)-1-(1,1'-Biphenyl-4-yl)-1,2,3,4-tetrahydro-beta-carboline-3-carboxamide |
| 33 | 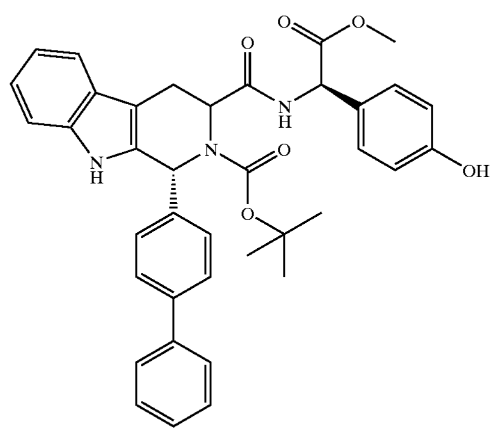 | (R)-1-Methoxycarbonyl-1-(4-hydroxyphenyl)methyl(1R)-1-(1,1'-Biphenyl-4-yl)-2-tert-butoxycarbonyl-1,2,3,4-tetrahydro-beta-carboline-3-carboxamide |
| 34 | 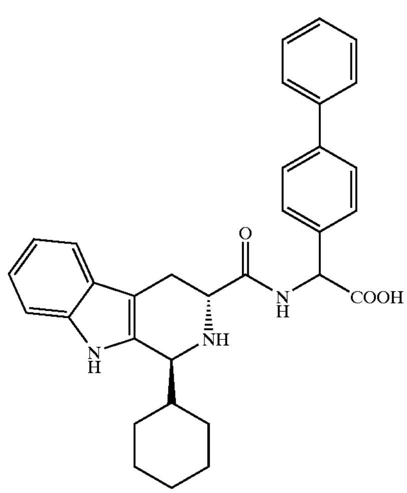 | 1-(1,1'-Biphenyl-4-yl)1-carboxymethyl(1S, 3R)-1 Cyclohexyl-1,2,3,4-tetrahydro-beta-carboline-3-carboxamide |

TABLE 1-continued

| Example | Structure | Name |
|---|---|---|
| 35 | 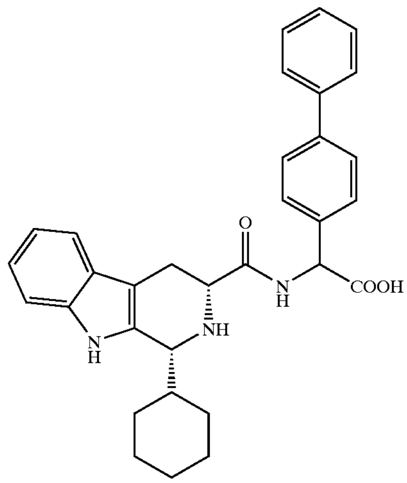 | 1-(1,1'-Biphenyl-4-yl)1-carboxymethyl(1R, 3R)-1 Cyclohexyl-1,2,3,4-tetrahydro-beta-carboline-3-carboxamide |
| 36 | 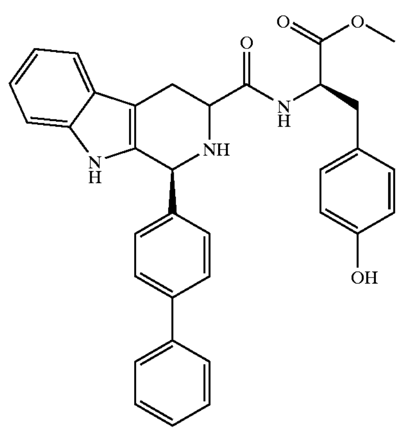 | (R)-1-Methoxycarbonyl-1-(4-hydroxybenzyl)methyl(1S)-1-(1,1'-Biphenyl-4-yl)-1,2,3,4-tetrahydro-beta-carboline-3-carboxamide |
| 37 | 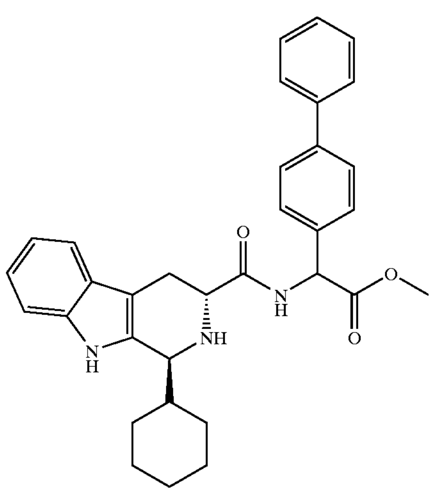 | 1-Methoxycarbonyl-1-(1,1'-Biphenyl-4-yl)methyl(1S, 3R)-1-Cyclohexyl-1,2,3,4-tetrahydro-beta-carboline-3-carboxamide |

TABLE 1-continued

| Example | Structure | Name |
|---|---|---|
| 38 | 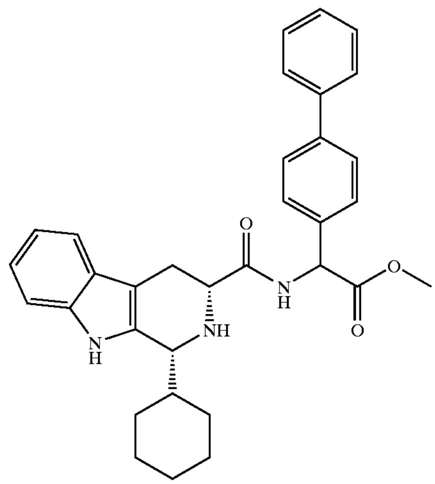 | 1-Methoxycarbonyl-1-(1,1'-Biphenyl-4-yl)methyl (1R, 3R)-1-Cyclohexyl-1,2,3,4-tetrahydro-beta-carboline-3-carboxamide |
| 39 | 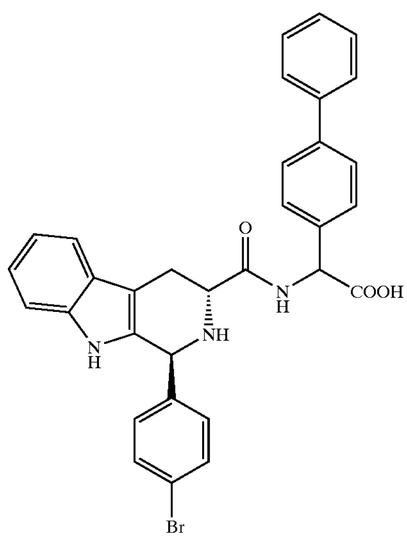 | 1-Carboxy-1-(1,1-Biphenyl-4-yl)methyl(1S, 3R)-1-(4-Bromophenyl)-1,2,3,4-tetrahydro-beta-carboline-3-carboxamide |
| 40 | 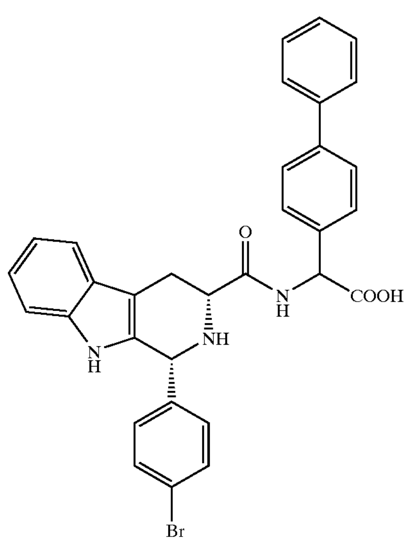 | 1-Carboxy-1-(1,1'-Biphenyl-4-yl)methyl(1R, 3R)-1-(4-Bromophenyl)-1,2,3,4-tetrahydro-beta-carboline-3-carboxamide |

TABLE 1-continued

| Example | Structure | Name |
|---|---|---|
| 41 | 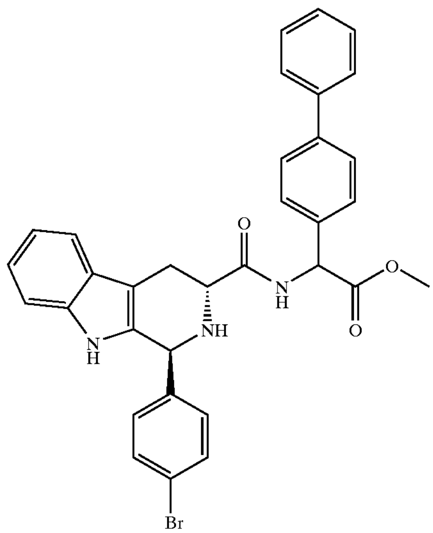 | 1-Methoxycarbonyl-1-(1,1'-Biphenyl-4-yl)methyl(1S, 3R)-1-(4-Bromophenyl)-1,2,3,4-tetrahydro-beta-carboline-3-carboxamide |
| 42 | 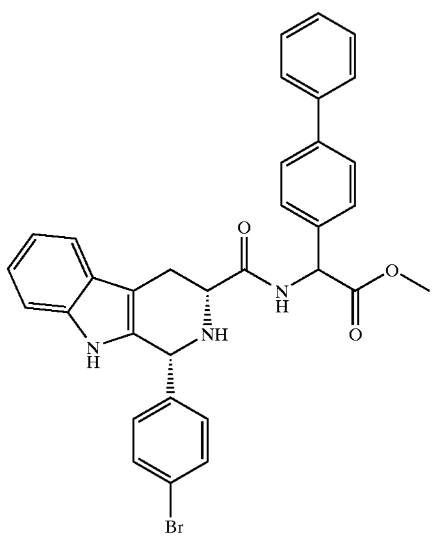 | 1-Methoxycarbonyl-1-(1,1'-Biphenyl-4-yl)methyl(1R, 3R)-1-(4-Bromophenyl)-1,2,3,4-tetrahydro-beta-carboline-3-carboxamide |
| 43 | 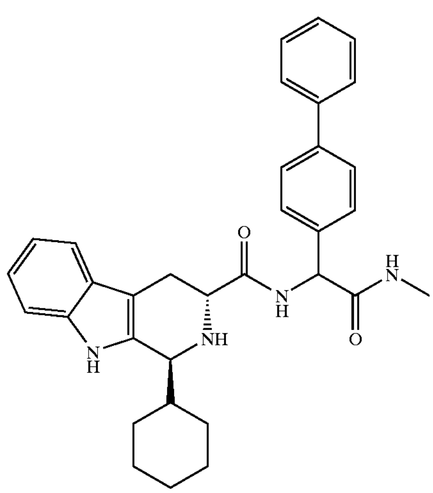 | 1-Methoxycarbamoyl-1-(1,1'-Biphenyl-4-yl)methyl(1S, 3R)-1-Cyclohexyl-1,2,3,4-tetrahydro-beta-carboline-3-carboxamide |

TABLE 1-continued

| Example | Structure | Name |
|---|---|---|
| 44 | 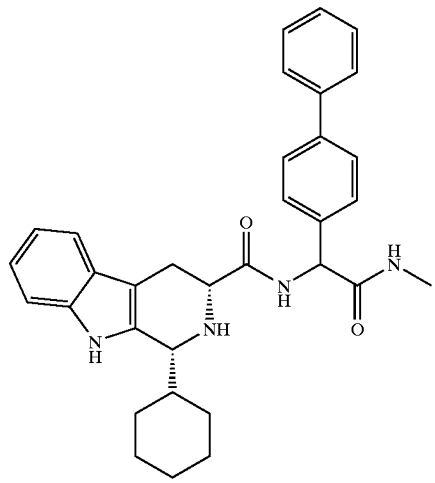 | 1-Methylcarbamoyl-1-(1,1'-Biphenyl-4-yl)methyl(1R, 3R)-1-Cyclohexyl-1,2,3,4-tetrahydro-beta-carboline-3-carboxamide |
| 45 | 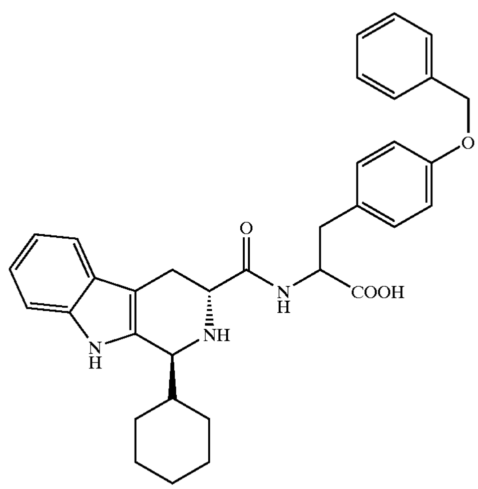 | 2-[4-(benzyloxy)phenyl]-1-carboxy 1-ethyl(1S, 3R)-1-Cyclohexyl-1,2,3,4-tetrahydro-beta-carboline-3-carboxamide |
| 46 | 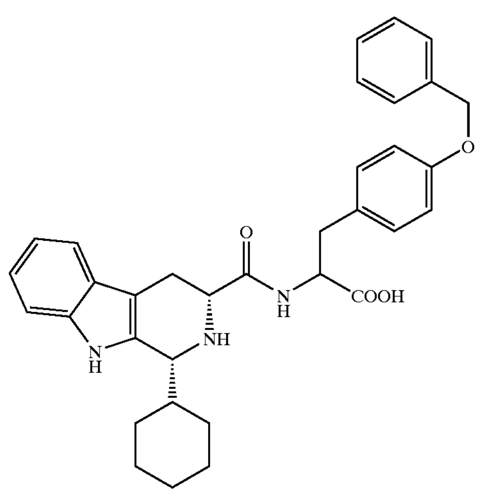 | 2-[4-(benzyloxy)phenyl]-1-carboxy-1-ethyl(1R, 3R)-1-Cyclohexyl-1,2,3,4-tetrahydro-beta-carboline-3-carboxamide |

TABLE 1-continued

| Example | Structure | Name |
|---|---|---|
| 47 | 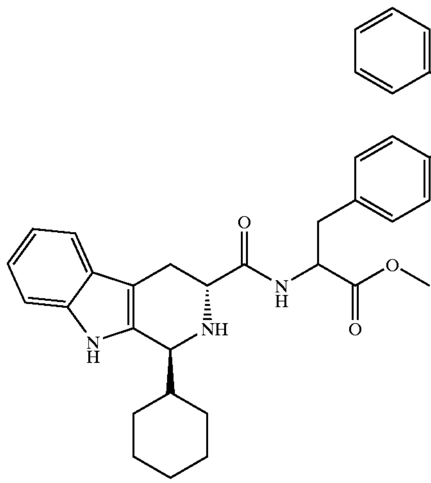 | 2-[4-(benzyloxy)phenyl]-1-methoxycarbonyl-1-ethyl(1S, 3R)-1-Cyclohexyl-1,2,3,4-tetrahydro-beta-carboline-3-carboxamide |
| 48 | 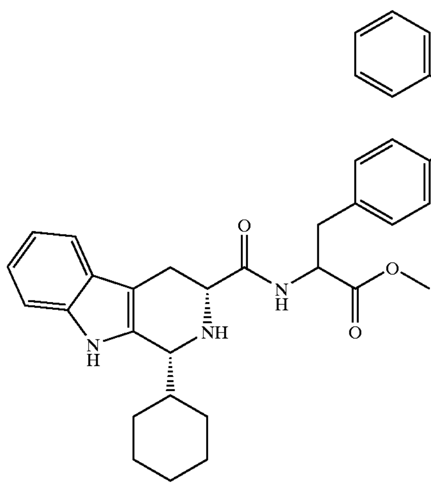 | 2-[4-(benzyloxy)phenyl]-1-methoxycarbonyi-1-ethyl (1R, 3R)-1-Cyclohexyl-1,2,3,4-tetrahydro-beta-carboline-3-carboxamide |
| 49 | 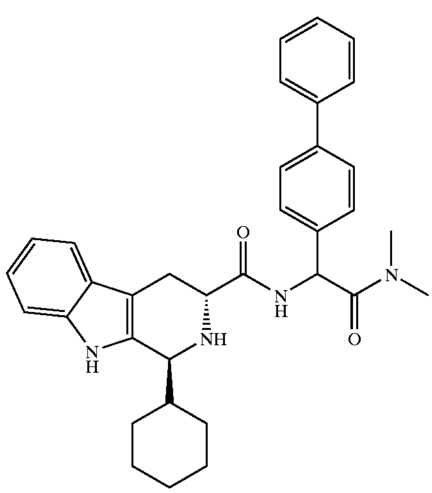 | 1-Dimethylaminocarbamoyl-1-(1,1'-Biphenyl-4-yl)methyl(1S, 3R)-1-Cyclohexyl-1,2,3,4-tetrahydro-beta-carboline-3-carboxamide |

TABLE 1-continued
| Example | Structure | Name |
|---|---|---|
| 50 | 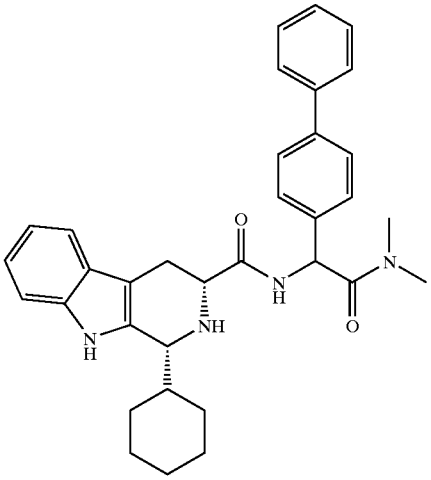 | 1-Dimethylaminocarbamoyl-1-(1,1'-Biphenyl-4-yl)methyl(1R, 3R)-1-Cyclohexyl-1,2,3,4-tetrahydro-beta-carboline-3-carboxamide |
| 51 | 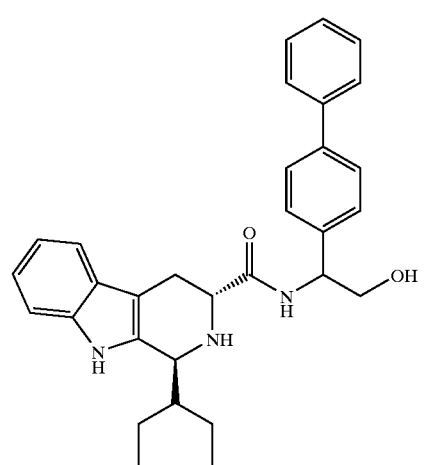 | 1-Hydroxymethyl-1-(1,1'-Biphenyl-4-yl)methyl(1S, 3R)-1-Cyclohexyl-1,2,3,4-tetrahydro-beta-carboline-3-carboxamide |
| 52 | 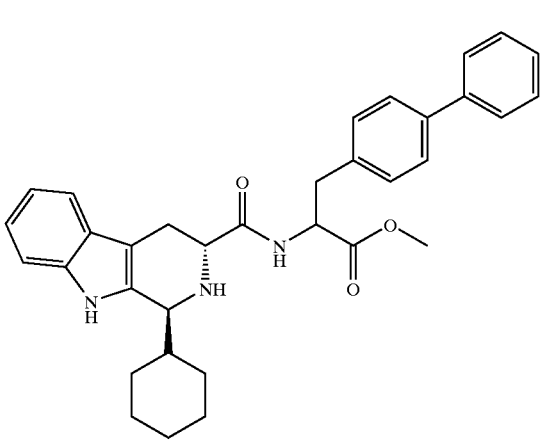 | 2-(1,1'-Biphenyl-4-yl)1-methoxycarbonyl-1-ethyl(1S, 3R)-1-Cyclohexyl-1,2,3,4-tetrahydro-beta-carboline-3-carboxamide |

TABLE 1-continued

| Example | Structure | Name |
|---|---|---|
| 53 | 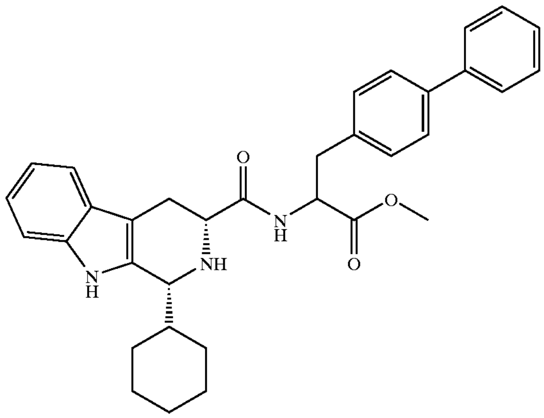 | 2-(1,1'-Biphenyl-4-yl)1-methoxycarbonyl-1-ethyl(1R, 3R)-1-Cyclohexyl-1,2,3,4-tetrahydro-beta-carboline-3-carboxamide |
| 54 | 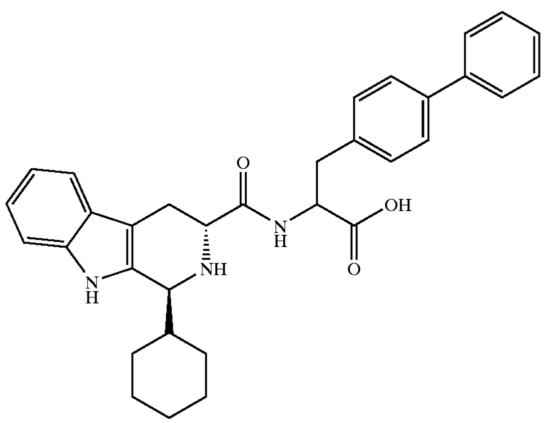 | 2-(1,1'-Biphenyl-4-yl)1-carboxy-1-ethyl(1S, 3R)-1 Cyclohexyl-1,2,3,4-tetrahydro-beta-carboline-3-carboxamide |
| 55 | 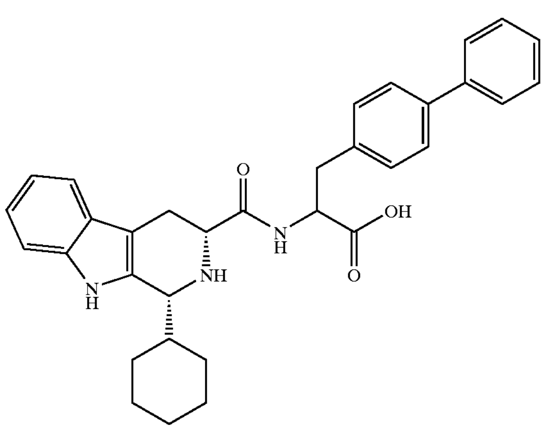 | 2-(1,1'-Biphenyl-4-yl)1-carboxy-1-ethyl(1R, 3R)-1-Cyclohexyl-1,2,3,4-tetrahydro-beta-carboline-3-carboxamide |

TABLE 1-continued

| Example | Structure | Name |
|---|---|---|
| 56 | 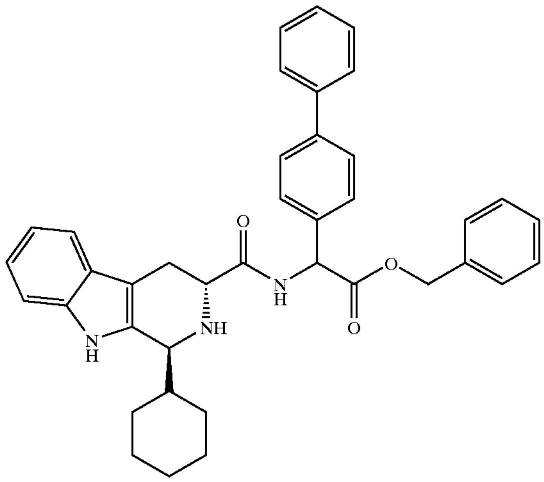 | 1-Benzyloxycarbonyl-1-(1,1'-Biphenyl-4-yl)methyl(1R, 3R)-1-Cyclohexyl-1,2,3,4-tetrahydro-beta-carboline-3-carboxamide |
| 57 | 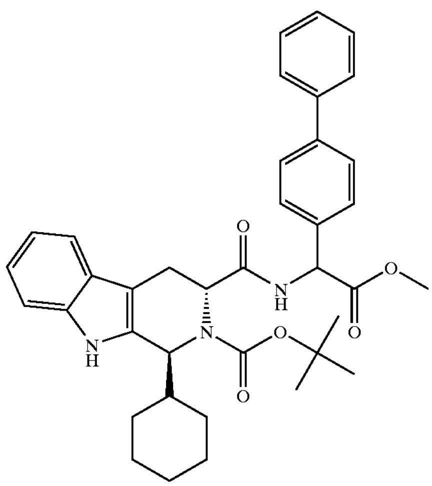 | 1-Methoxycarbonyl-1-(1,1'-Biphenyl-4-yl)methyl(1R, 3R)-1-Cyclohexyl-2-tert-butoxycarbonyl-1,2,3,4-tetrahydro-beta-carboline-3-carboxamide |
| 58 | 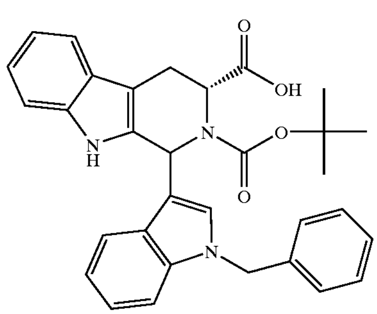 | (3R)-1-(1-benzylindol-3-yl)-2-tert-butoxycarbonyl-1,2,3,4-tetrahydro-beta-carboline-3-carboxylic Acid |

TABLE 1-continued

| Example | Structure | Name |
|---|---|---|
| 59 | 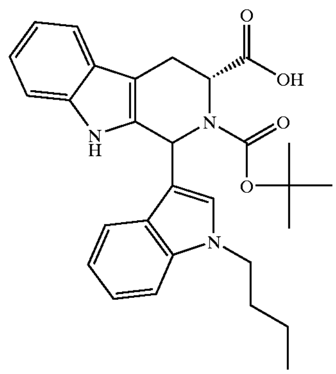 | (3R)-1-(1-butylindol-3-yl)-2-tert-butoxycarbonyl-1,2,3,4-tetrahydro-beta-carboline-3-carboxylic Acid |
| 60 | 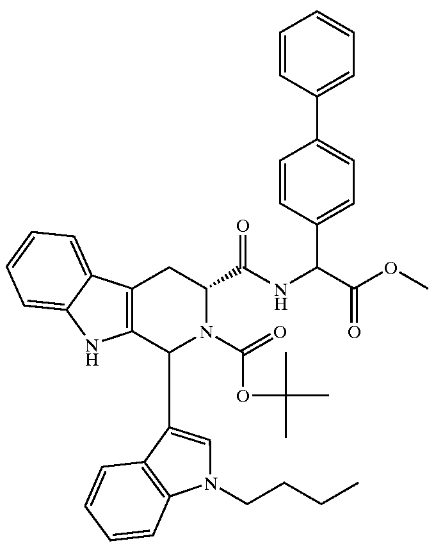 | 1-Methoxycarbonyl-1-(1,1'-Biphenyl-4-yl)methyl(3R)-1-(1-butylindol-3-yl)-1,2,3,4-tetrahydro-beta-carboline-3-carboxamide |
| 61 | 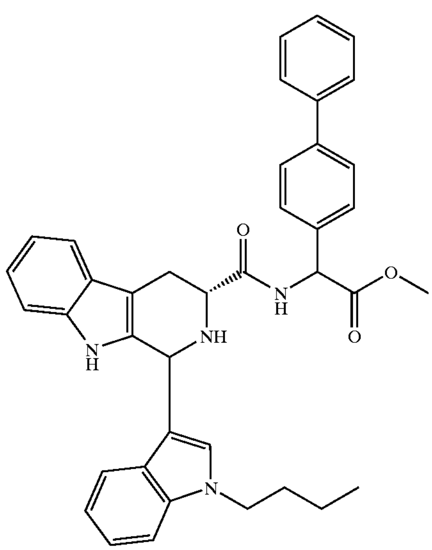 | 1-Methoxycarbonyl-1-(1,1'-Biphenyl-4-yl)methyl(3R)-1-(1-butylindol-3-yl)-1,2,3,4-tetrahydro-beta-carboline-3-carboxamide |

TABLE 1-continued

| Example | Structure | Name |
|---|---|---|
| 62 | 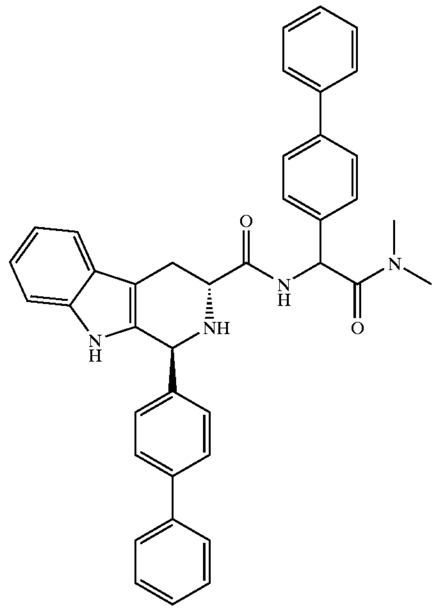 | 1-Dimethylcarbamoyl-1-(1,1'-biphenyl-4-yl)methyl(1S, 3R)-1-(1,1'-Biphenyl-4-yl)-1,2,3,4-tetrahydro-beta-carboline-3-carboxamide |
| 63 | 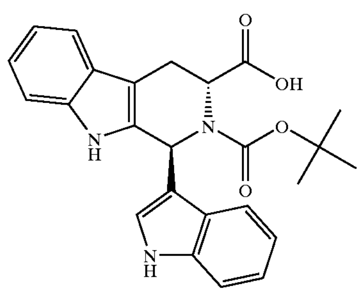 | (1S, 3R)-1-(Indol-3-yl)-2-tert-butoxycarbonyl-1,2,3,4-tetrahydro-beta-carboline-3-carboxyiic Acid |
| 64 | 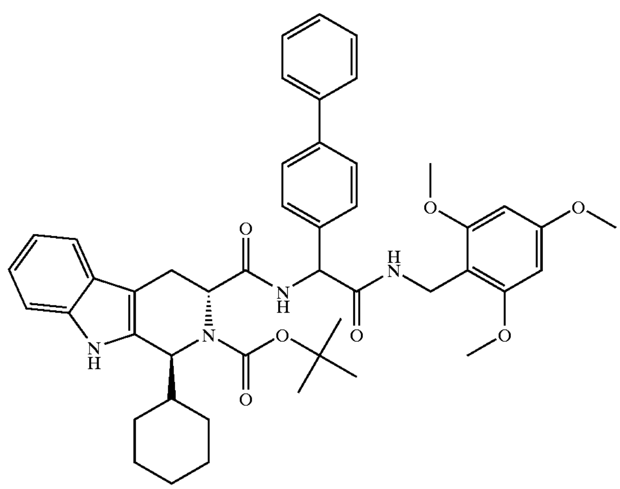 | 1-(2,4,6-trimethoxybenzylcarbamoyl)-1-(1,1'-Biphenyl-4-yl)methyl(1S, 3R)-1-Cyclohexyl-2-tert-butoxycarbonyl-1,2,3,4-tetrahydro-beta-carboline-3-carboxamide |

TABLE 1-continued

| Example | Structure | Name |
|---|---|---|
| 65 | 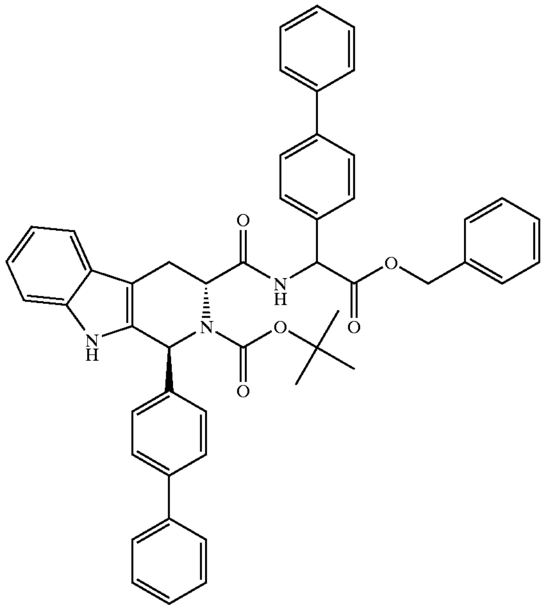 | 1-Benzyloxycarbonyl-1-(1,1'-Biphenyl-4-yl)methyl(1S, 3R)-1-(1,1'-Biphenyl-4-yl)-2-tert-butoxycarbonyl-1,2,3,4-tetrahydro-beta-carboline-3-carboxamide |
| 66 | 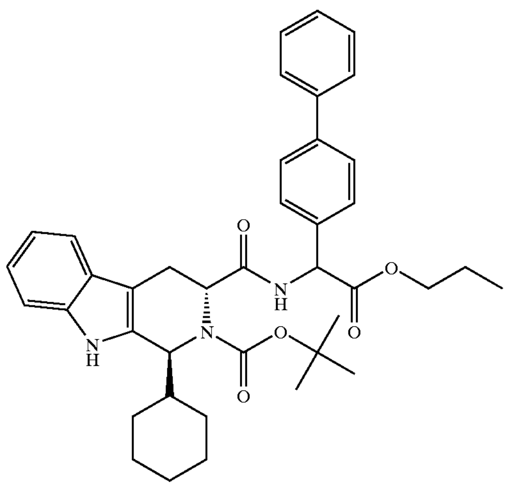 | 1-Propoxycarbonyl-1-(1,1'-Biphenyl-4-yl)methyl(1S, 3R)-1-Cyclohexyl-2-tert-butoxycarbonyl-1,2,3,4-tetrahydro-beta-carboline-3-carboxamide |
| 67 | 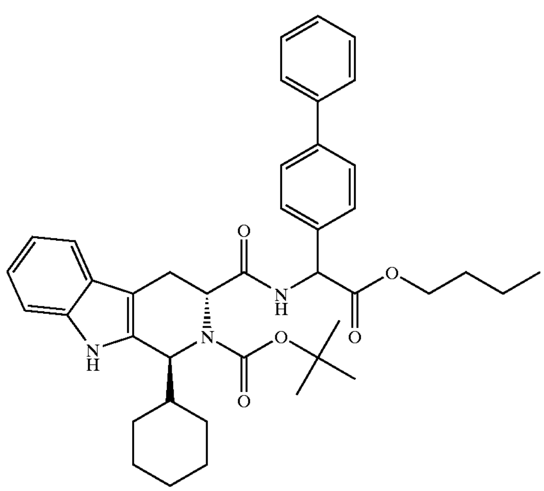 | 1-Butoxycarbonyl-1-(1,1'-Biphenyl-4-yl)methyl(1S, 3R)-1-Cyclohexyl-2-tert-butoxycarbonyl-1,2,3,4-tetrahydro-beta-carboline-3-carboxamide |

TABLE 1-continued

| Example | Structure | Name |
|---|---|---|
| 68 | 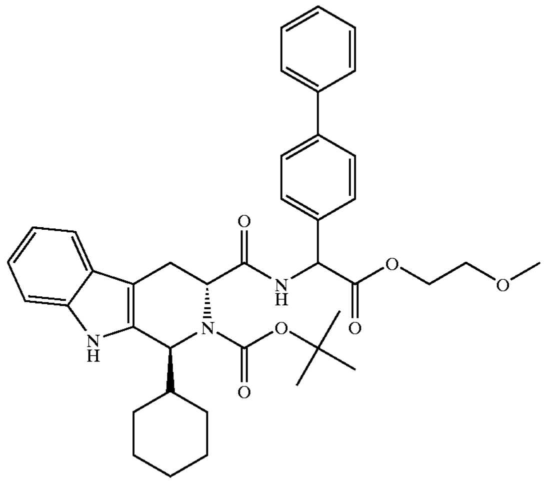 | 1-(2-Methoxy-1-ethoxycarbonyl)-1-(1,1'-Biphenyl-4-yl)methyl(1S, 3R)-1-Cyclohexyl-2-tert-butoxycarbonyl-1,2,3,4-tetrahydro-beta-carboline-3-carboxamide |
| 69 | 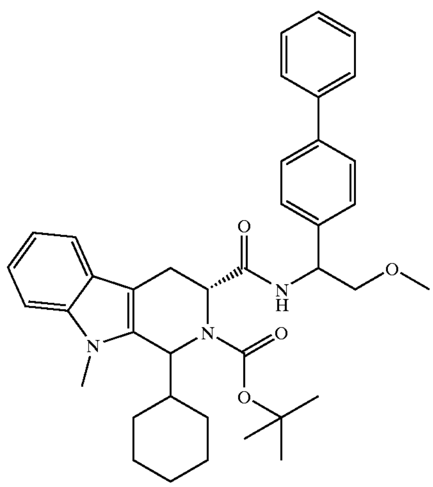 | 1-Methoxymethyl-1-(1,1'-Biphenyl-4-yl)methyl(3R)-1-Cyclohexyl-2-tert-butoxycarbonyl-9-methyl-1,2,3,4-tetrahydro-beta-carboline-3-carboxamide |
| 70 | 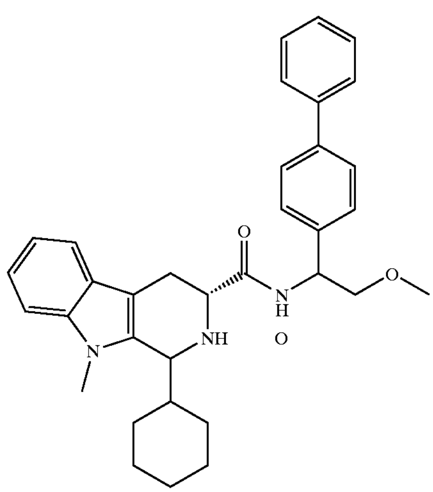 | 1-Methoxymethyl-1-(1,1'-Biphenyl-4-yl)methyl(3R)-1-Cyclohexyl-9-methyl-1,2,3,4-tetrahydro-beta-carboline-3-carboxamide |

TABLE 1-continued

| Example | Structure | Name |
|---|---|---|
| 71 | 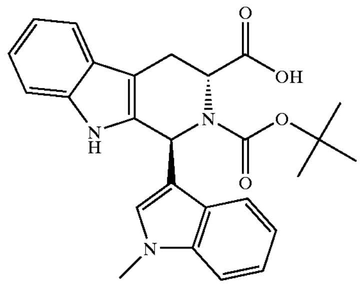 | (1S, 3R)-1-(1-methylindol-3-yl)-2-tert-butoxycarbonyl-1,2,3,4-tetrahydro-beta-carboline-3-carboxylic acid |
| 72 | 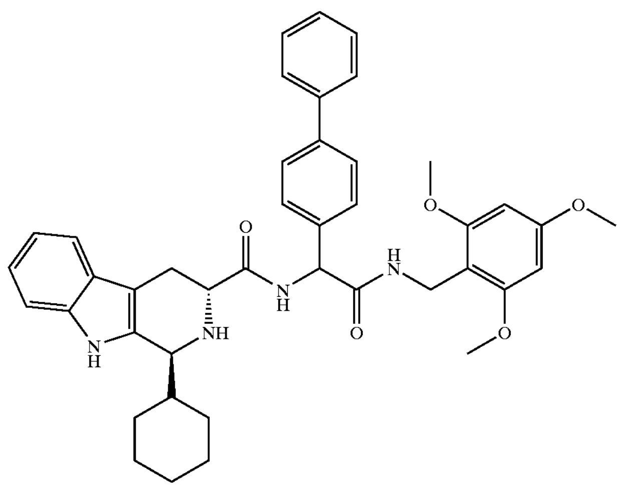 | 1-(2,4,6-trimethoxybenzylcarbamoyl)-1-(1,1'-Biphenyl-4-yl)methyl(1S, 3R)-1-Cyclohexyl-1,2,3,4-tetrahydro-beta-carboline-3-carbaxamide |
| 73 | 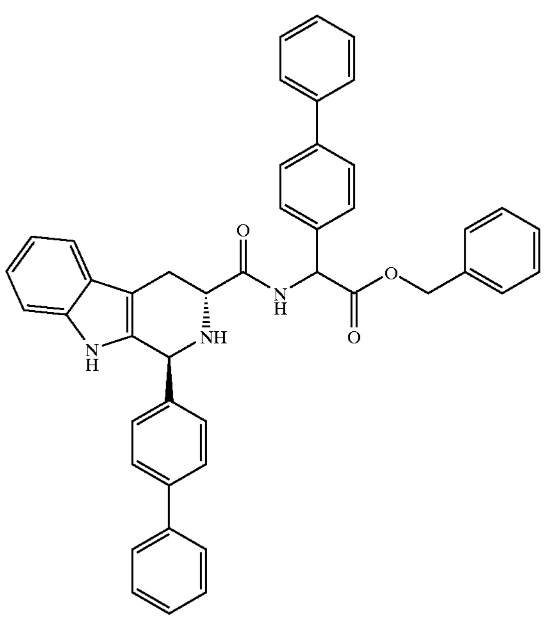 | 1-(Benzyloxycarbonyl)-1-(1,1'-Biphenyl-4-yl)methyl(1S, 3R)-1-(1,1'-Biphenyl-4-yl)-1,2,3,4-tetrahydro-beta-carboline-3-carbaxamide |

TABLE 1-continued

| Example | Structure | Name |
|---|---|---|
| 74 | 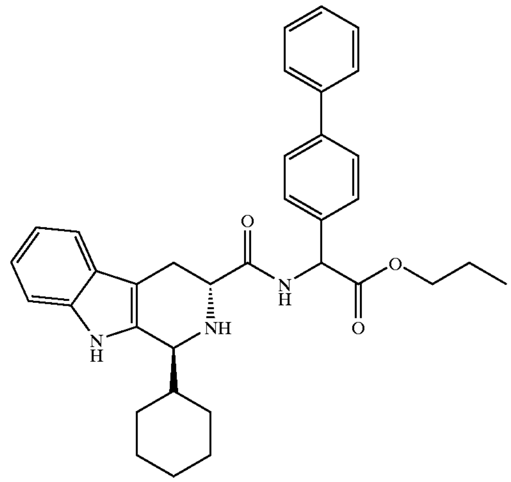 | 1-Propoxycarbonyl-1-(1,1'-Biphenyl-4-yl)methyl(1S, 3R)-1-Cyclohexyl-1,2,3,4-tetrahydro-beta-carboline-3-carboxamide |
| 75 | 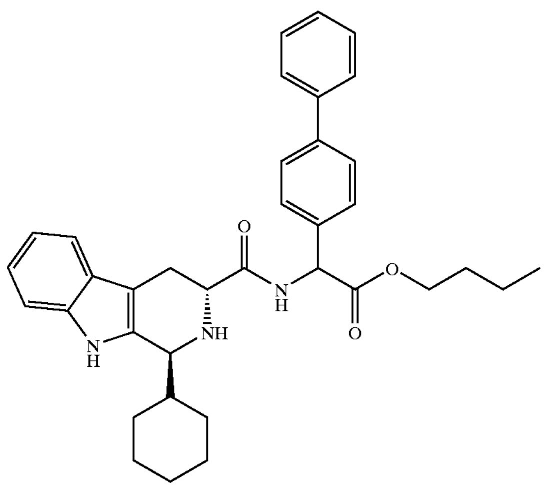 | 1-Butoxycarbonyl-1-(1,1'-Biphenyl-4-yl)methyl(1S, 3R)-1-Cyclohexyl-1,2,3,4-tetrahydro-beta-carboline-3-carboxamide |
| 76 | 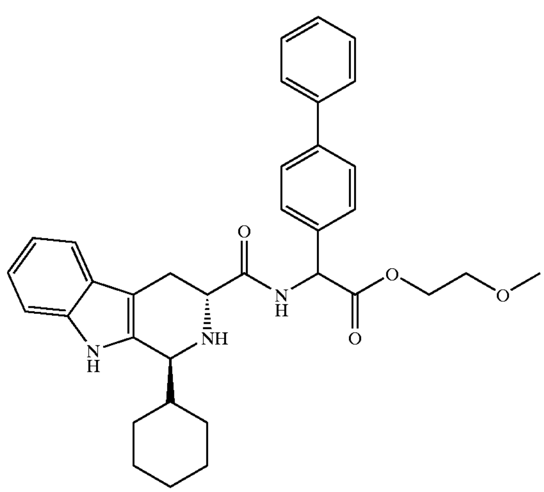 | 1-(2-Methoxy-1-ethoxycarbonyl)-1-(1,1'-Biphenyl-4-yl)methyl(1S, 3R)-1-Cyclohexyl-1,2,3,4-tetrahydro-beta-carboline-3-carboxamide |

TABLE 1-continued

| Example | Structure | Name |
|---|---|---|
| 77 | 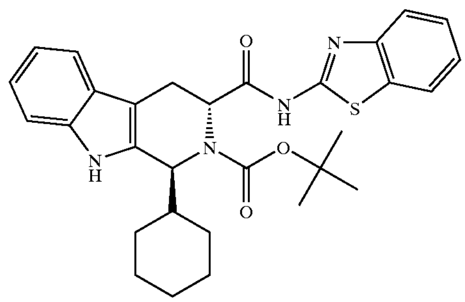 | Benzothiazol-2-yl(1S, 3R)-1-Cyclohexyl-2-tert-butoxycarbonyl-1,2,3,4-tetrahydro-beta-carboline-3-carboxamide |
| 78 | 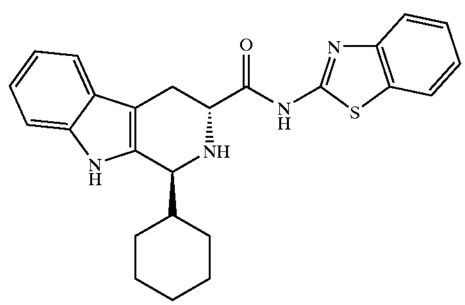 | Benzothiazol-2-yl(1S, 3R)-1-Cyclohexyl-1,2,3,4-tetrahydro-beta-carboline-3-carboxamide |
| 79 | 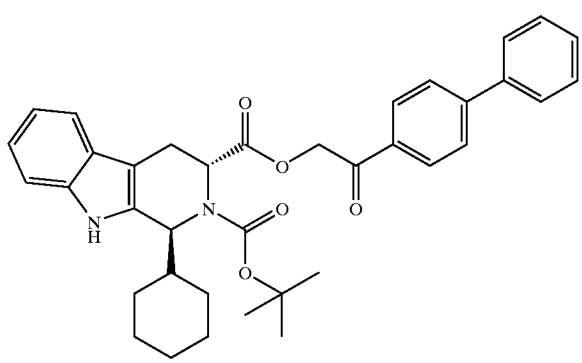 | 1,1'-Biphenyl-4-oylmethyl(1S, 3R)-1-Cyclohexyl-2-tert-butoxycarbonyl-1,2,3,4-tetrahydro-beta-carboline-3-carboxylate |
| 80 | 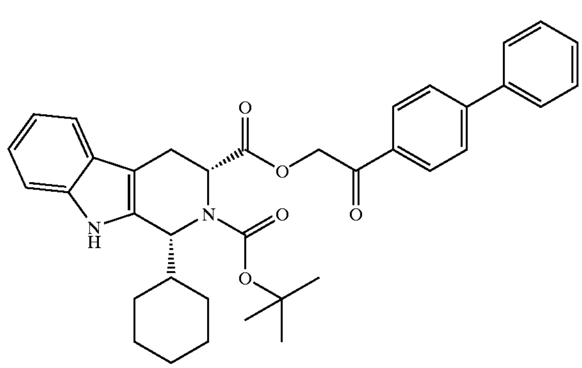 | 1,1'-Biphenyl-4-oylmethyl(1R, 3R)-1-Cyclohexyl-2-tert-butoxycarbonyl-1,2,3,4-tetrahydro-beta-carboline-3-carboxylate |

TABLE 1-continued

| Example | Structure | Name |
| --- | --- | --- |
| 81 | 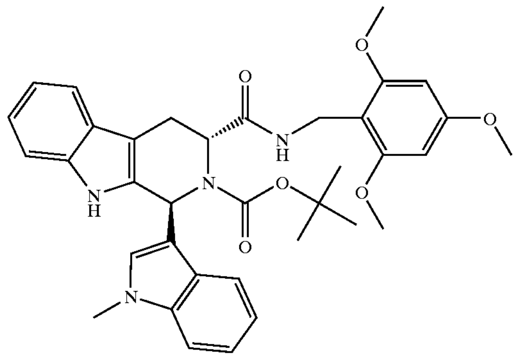 | 2,4,6-Trimethoxybenzyl(1S, 3R)-1-(1-methylindol-3-yl)-1,2,3,4-tetrahydro-beta-carboline-3-carboxamide |
| 82 | 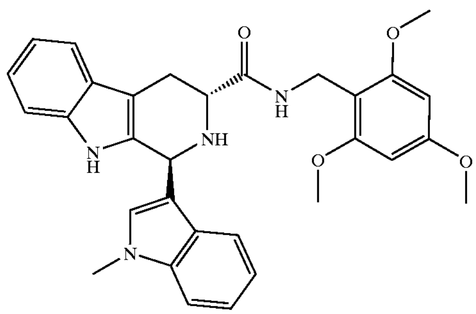 | 2,4,6-Trimethoxybenzyl(1S, 3R)-1-(1-methylindol-3-yl)-1,2,3,4-tetrahydro-beta-carboline-3-carboxamide |
| 83 | 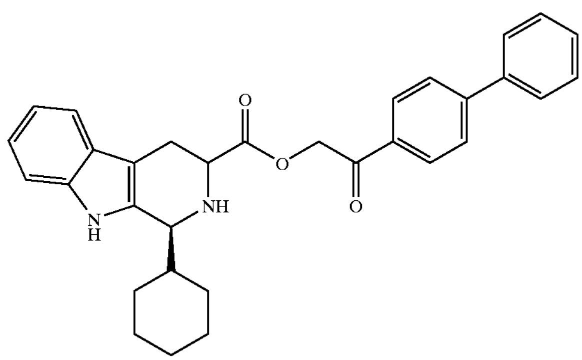 | 1,1'-Biphenyl-4-oylmethyl(1S)-1-Cyclohexyl-1,2,3,4-tetrahydro-beta-carboline-3-carboxylate |
| 84 | 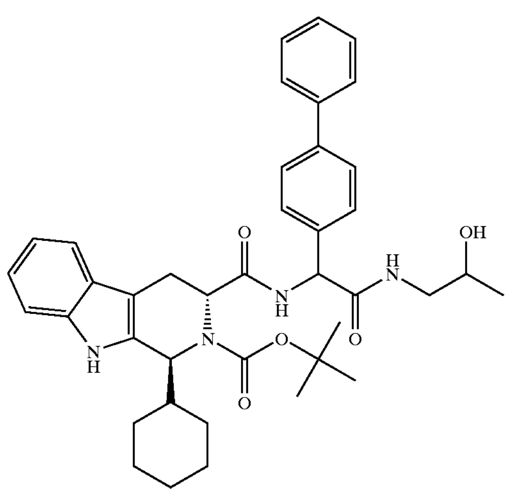 | 1-(2-Hydroxy-1-propylcarbamoyl-1-(1,1'-Biphenyl-4-yl)methyl(1S, 3R)-1-Cyclohexyl-2-tert-butoxycarbonyl-1,2,3,4-tetrahydro-beta-carboline-3-carboxamide |

TABLE 1-continued

| Example | Structure | Name |
|---|---|---|
| 85 | 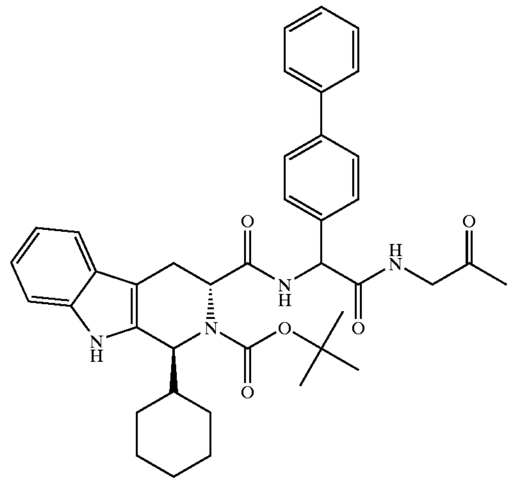 | 1-(2-Oxo-1-propylcarbamoyl-1-(1,1'-Biphenyl-4-yl)methyl(1S, 3R)-1-Cyclohexyl-2-tert-butoxycarbonyl-1,2,3,4-tetrahydro-beta-carboline-3-carboxamide |

In the compounds of Formula (I), the various functional groups represented should be understood to have a point of attachment at the functional group having the hyphen. In other words, in the case of -alkylene-aryl, it should be understood that the point of attachment is the alkylene group; an example would be benzyl. In the case of a group such as —C(O)—NH— alkylene-aryl, the point of attachment is the carbonyl carbon.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

In another aspect, the present invention comprises a pharmaceutical composition comprising the compound of Formula (I) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkyl" as used herein include, but are not limited to, methyl, n-butyl, n-pentyl, isobutyl, and isopropyl, and the like. As used herein, the term "lower" refers to a group having between one and six carbons.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkylene" as used herein include, but are not limited to, methylene, ethylene, and the like.

As used herein, the term "alkyline" refers to a straight or branched chain trivalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkyline" as used herein include, but are not limited to, methine, 1,1,2-ethyline, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkenyline" refers to a straight or branched chain trivalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkenyline" as used herein include, but are not limited to, ethene-1,1,2-triyl, propene-1,2,3-triyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group optionally with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkyline" refers to an non-aromatic alicyclic trivalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkyline" as used herein include, but are not limited to, cyclopropyl-1,1,2-triyl, cyclohexyl-1,3,4-triyl, and the like.

As used herein, the term "heterocyclic" or the term "heterocyclyl" refers to a three to twelve-membered heterocyclic ring optionally having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "heterocyclyline" refers to a three to twelve-membered heterocyclic ring triradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclyline" include, but are not limited to, tetrahydrofuran-2,4,5-triyl, morpholine-2,3,4-triyl, pyran-2,4,5-triyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower hydroxyalkyl, lower carboxyalkyl, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "aryline" refers to a benzene ring triradical or to a benzene ring system triradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "aryline" include, but are not limited to, benzene-1,2,4-triyl, naphthalene-1,4,8-triyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, lower hydroxyalkyl, lower carboxyalkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "heteroaryline" refers to a five- to seven-membered aromatic ring triradical, or to a polycyclic heterocyclic aromatic ring triradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroaryline" used herein are furan-2,4,5-triyl, thiophene-2,3,4-triyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

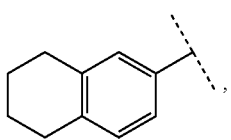

and the like.

As used herein, the term "fused cycloalkylarylene" refers to a fused cycloalkylaryl, wherein the aryl group is divalent. Examples include

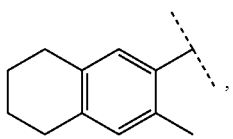

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

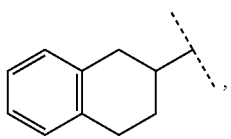

and the like.

As used herein, the term "fused arylcycloalkylene" refers to a fused arylcycloalkyl, wherein the cycloalkyl group is divalent. Examples include

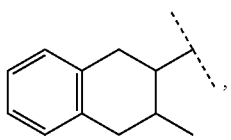

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

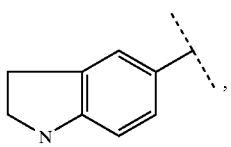

and the like.

As used herein, the term "fused heterocyclylarylene" refers to a fused heterocyclylaryl, wherein the aryl group is divalent. Examples include

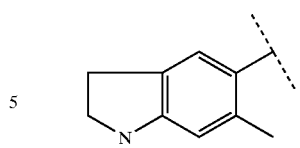

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

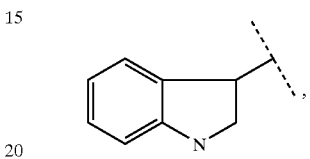

and the like.

As used herein, the term "fused arylheterocyclylene" refers to a fused arylheterocyclyl, wherein the heterocyclyl group is divalent. Examples include

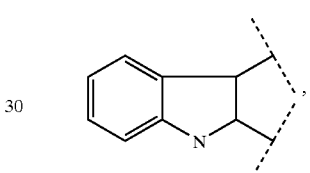

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

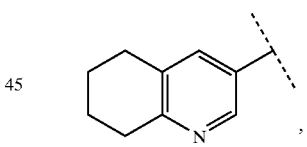

and the like.

As used herein, the term "fused cycloalkylheteroarylene" refers to a fused cycloalkylheteroaryl, wherein the heteroaryl group is divalent. Examples include

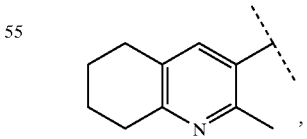

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

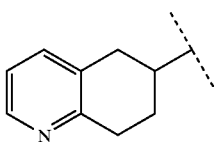

and the like.

As used herein, the term "fused heteroarylcycloalkylene" refers to a fused heteroarylcycloalkyl, wherein the cycloalkyl group is divalent. Examples include

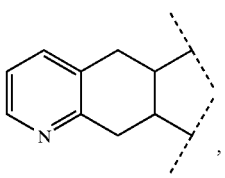

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

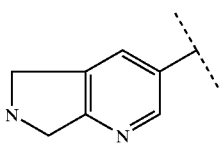

and the like.

As used herein, the term "fused heterocyclylheteroarylene" refers to a fused heterocyclylheteroaryl, wherein the heteroaryl group is divalent. Examples include

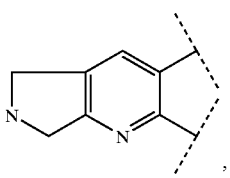

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include-5-aza-2,3-dihydrobenzofuran-2-yl,

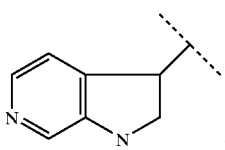

and the like.

As used herein, the term "fused heteroarylheterocyclylene" refers to a fused heteroarylheterocyclyl, wherein the heterocyclyl group is divalent. Examples include

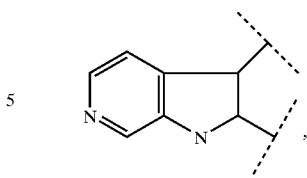

and the like.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO—$, where $R_a$ is alkyl.

As used herein, the term "alkenyloxy" refers to the group $R_bO—$, where $R_b$ is alkenyl.

As used herein, the term "alkynyloxy" refers to the group $R_cO—$, where $R_c$ is alkynyl.

As used herein, the term "alkylsulfanyl" refers to the group $R_aS—$, where $R_a$ is alkyl.

As used herein, the term "alkenylsulfanyl" refers to the group $R_bS—$, where $R_b$ is alkenyl.

As used herein, the term "alkynylsulfanyl" refers to the group $R_cS—$, where $R_c$ is alkynyl.

As used herein, the term "alkylsulfenyl" refers to the group $R_aS(O)—$, where $R_a$ is alkyl.

As used herein, the term "alkenylsulfenyl" refers to the group $R_bS(O)—$, where $R_b$ is alkenyl.

As used herein, the term "alkynylsulfenyl" refers to the group $R_cS(O)—$, where $R_c$ is alkynyl.

As used herein, the term "alkylsulfonyl" refers to the group $R_aSO_2—$, where $R_a$ is alkyl.

As used herein, the term "alkenylsulfonyl" refers to the group $R_bSO_2—$, where $R_b$ is alkenyl.

As used herein, the term "alkynylsulfonyl" refers to the group $R_cSO_2—$, where $R_c$ is alkynyl.

As used herein, the term "acyl" refers to the group $R_aC(O)—$, where $R_a$ is alkyl, alkenyl, alkynyl, cycloalkyl, cycloalkenyl, or heterocyclyl.

As used herein, the term "aroyl" refers to the group $R_aC(O)—$, where $R_a$ is aryl.

As used herein, the term "heteroaroyl" refers to the group $R_aC(O)—$, where $R_a$ is heteroaryl.

As used herein, the term "alkoxycarbonyl" refers to the group $R_aOC(O)—$, where $R_a$ is alkyl.

As used herein, the term "acyloxy" refers to the group $R_aC(O)O—$, where $R_a$ is alkyl, alkenyl, alkynyl, cycloalkyl, cycloalkenyl, or heterocyclyl.

As used herein, the term "aroyloxy" refers to the group $R_aC(O)O—$, where $R_a$ is aryl.

As used herein, the term "heteroaroyloxy" refers to the group $R_aC(O)O—$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $—CH_2—O—CH_2—$, $—CH_2—SO_2—CH_2—$, $—CH_2—NH—CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —SO$_2$NH$_2$.

As used herein, the term "carbamoyl" shall refer to the substituent —C(O)NH$_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —S(O)$_2$—.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., $C_1$–$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of Formula (I): for example, the lactam formed by a carboxylic group in $R_2$ and an amine in $R_4$, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" or "treating" as used herein, refers to the full spectrum of treatments for a given disorder from which the patient is suffering, including alleviation of one, most of all symptoms resulting from that disorder, to an outright cure for the particular disorder or prevention of the onset of the disorder.

The present invention also provides a method for the synthesis of compounds useful as intermediates in the preparation of compounds of Formula (I) along with methods for the preparation of compounds of Formula (I). The compounds can be prepared readily according to the following reaction Schemes (in which all variables are as defined before) using readily available starting materials, reagents and conventional synthesis procedures. In these reactions, it is also possible to make use of variants which are themselves known to those of ordinary skill in this art, but are not mentioned in greater detail.

Abbreviations used in the Examples are as follows:

| | | |
|---|---|---|
| APCI | = | atmospheric pressure chemical ionization |
| BOC | = | tert-butoxycarbonyl |
| BOP | = | (1-benzotriazolyloxy)tris(dimethylamino)phosphonium hexafluorophosphate |
| d | = | day |
| DIAD | = | diisopropyl azodicarboxylate |
| DCC | = | dicyclohexylcarbodiimide |
| DCM | = | dichloromethane |
| DIC | = | diisopropylcarbodiimide |
| DIEA | = | diisopropylethylamine |
| DMA | = | N,N-dimethylacetamide |
| DMAP | = | dimethylaminopyridine |
| DME | = | 1,2 dimethoxyethane |
| DMF | = | N,N-dimethylformamide |
| DMPU | = | 1,3-dimethypropylene urea |

-continued

| | | |
|---|---|---|
| DMSO | = | dimethylsulfoxide |
| EDC | = | 1-ethyl-3-(3-dimethylaminopropyl)-carbodiimide hydrochloride |
| EDTA | = | ethylenediamine tetraacetic acid |
| ELISA | = | enzyme - linked immunosorbent assay |
| ESI | = | electrospray ionization |
| ether | = | diethyl ether |
| EtOAc | = | ethyl acetate |
| FBS | = | fetal bovine serum |
| g | = | gram |
| h | = | hour |
| HBTU | = | O-benzotriazol-1-yl-N,N,N',N'-tetramethyluronium hexafluorophosphate |
| HMPA | = | hexamethylphosphoric triamide |
| HOBt | = | 1-hydroxybenzotriazole |
| Hz | = | hertz |
| i.v. | = | intravenous |
| kD | = | kiloDalton |
| L | = | liter |
| LAH | = | lithium aluminum hydride |
| LDA | = | lithium diisopropylamide |
| LPS | = | lipopolysaccharide |
| M | = | molar |
| m/z | = | mass to charge ratio |
| mbar | = | millibar |
| MeOH | = | methanol |
| mg | = | milligram |
| min | = | minute |
| mL | = | milliliter |
| mM | = | millimolar |
| mmol | = | millimole |
| mol | = | mole |
| mp | = | melting point |
| MS | = | mass spectrometry |
| N | = | normal |
| NMM | = | N-methylmorpholine, 4-methylmorpholine |
| NMR | = | nuclear magnetic resonance spectroscopy |
| p.o. | = | per oral |
| PBS | = | phosphate buffered saline solution |
| PMA | = | phorbol myristate acetate |
| ppm | = | parts per million |
| psi | = | pounds per square inch |
| $R_f$ | = | relative TLC mobility |
| rt | = | room temperature |
| s.c. | = | subcutaneous |
| SPA | = | scintillation proximity assay |
| TEA | = | triethylamine |
| TFA | = | trifluoroacetic acid |
| THF | = | tetrahydrofuran |
| THP | = | tetrahydropyranyl |
| TLC | = | thin layer chromatography |
| TMSBr | = | bromotrimethylsilane, trimethylsilylbromide |
| $T_r$ | = | retention time |

Unless otherwise specified, the variables in the Schemes are as defined for Formula (I).

Intermediate (4) in Scheme I may be prepared by employing a cyclization/condensation procedure as described in Chemical Reviews, (1995), 95, 6. Treatment of (1) with an aldehyde $R_1$—CHO in dichloromethane in the presence of TFA at a temperature ranging from −78° C. to 50° C. affords the fused heterocyclic system (2). $PG_2$ may be hydrogen or a lower alkyl group or other suitable ester protecting group. (2) may be protected at N-2 giving (2) by methods known in the art. For example, treatment of (2) with di-tert-butyl dicarbonate and a weak base such as sodium bicarbonate in an aqueous organic solvent such as THF affords the N-2-tert-butyl carbamate (3), where $PG_1$ is —C(O)—O-t-Bu. $PG_2$ may be removed by suitable methods known in the art. For example, where $PG_2$ is a simple alkyl group such as methyl, ethyl, etc, treatment of (3) with aqueous alkali followed by neutralization with weak acid affords (4).

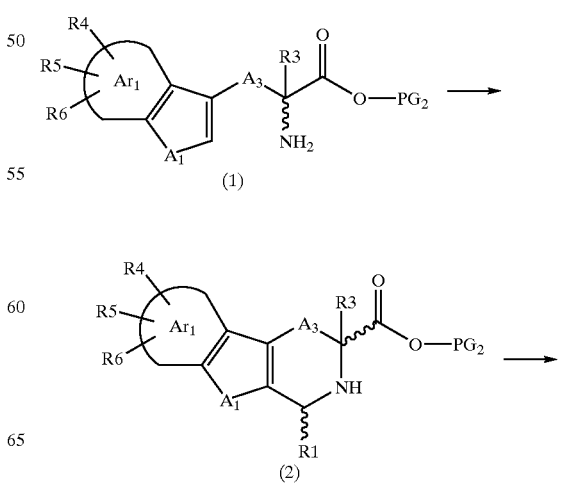

Scheme 1

Scheme 2

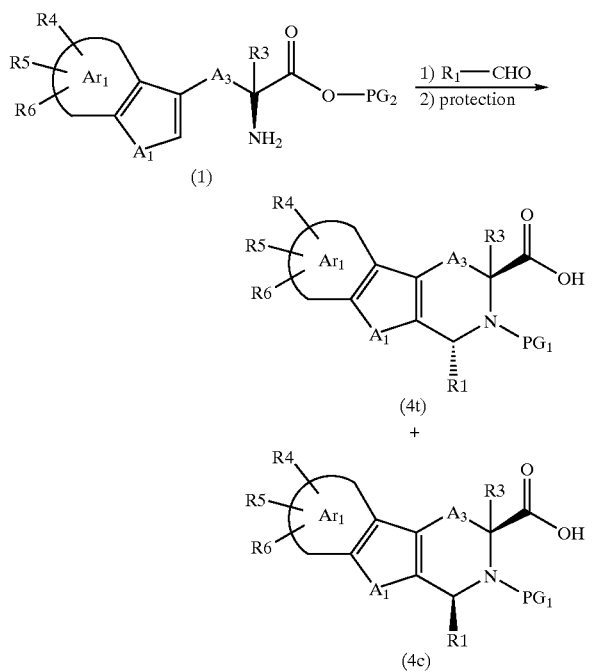

Where higher reaction temperatures are employed, such as temperatures of from 25° C. to 100° C., the trans isomer (4t) may be formed in preference to the cis (4c) (Scheme 2).

Where lower reaction temperatures are employed, such as temperatures of from −78° C. to 0° C., the cis isomer (4c) may be formed in preference to the trans (4t) (Scheme 3).

Scheme 3

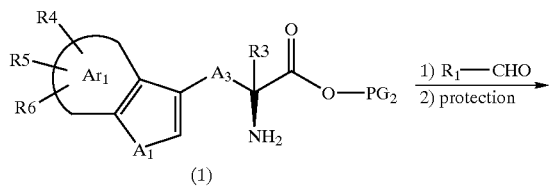

A N-2-protected fused heterocyclic carboxylic acid (4) (Scheme 4) can be treated with a peptide coupling agent such as EDC in the presence or absence of HOBt or HBTU, in a solvent such as DMF, and an amine reagent such as $HNR_{10}R_{11}$ to afford (5). The N-2 protecting group of (5) may be removed according to conditions known in the art, for example, where $PG_1$ is a tert-butoxycarbonyl group, treatment of (5) with a strong acid such as TFA in DCM affords the TFA salt of (6).

Scheme 4

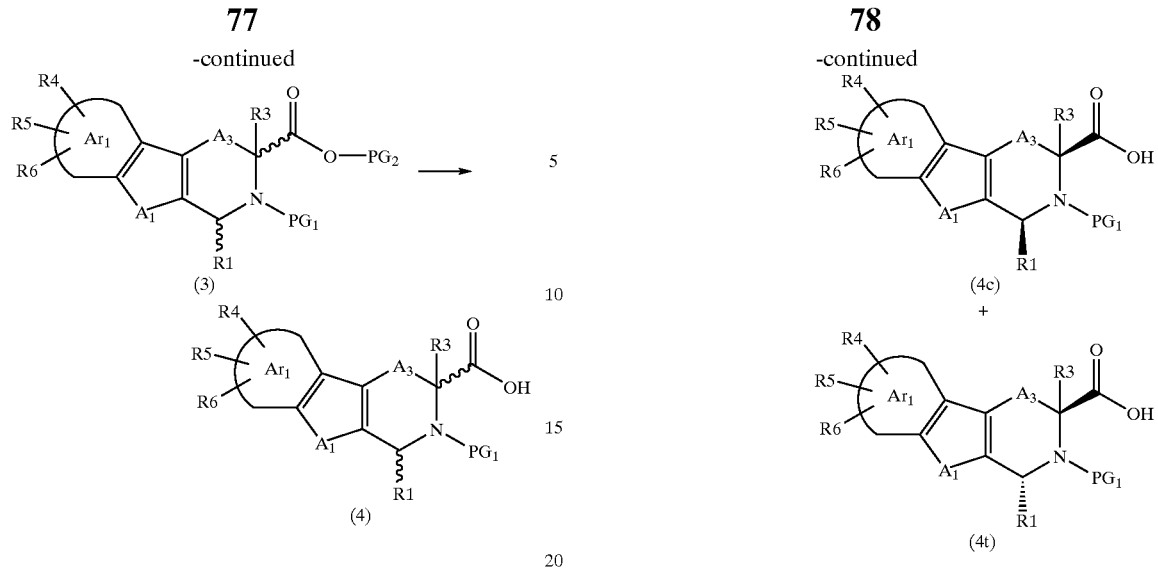

In an embodiment, the carboxy group in compound (4) (Scheme 5) can be utilized in the formation of amides, such as aromatic and aliphatic carboxamides. This transformation can be accomplished using standard methods. These methods include converting the desired acid into activated acid and reacting with amine. Methods to activate the carboxylic acid include reacting the acid with one or more equivalents of DCC/DIEA with or without one or more molar equivalents of HOBt in a suitable solvent such as DCM or DMF at temperartures ranging from 0° C. to room temperature, affording compound (7). In this instance, b and d may be integers such as but not limited to 1, 2, or 3.

Scheme 5

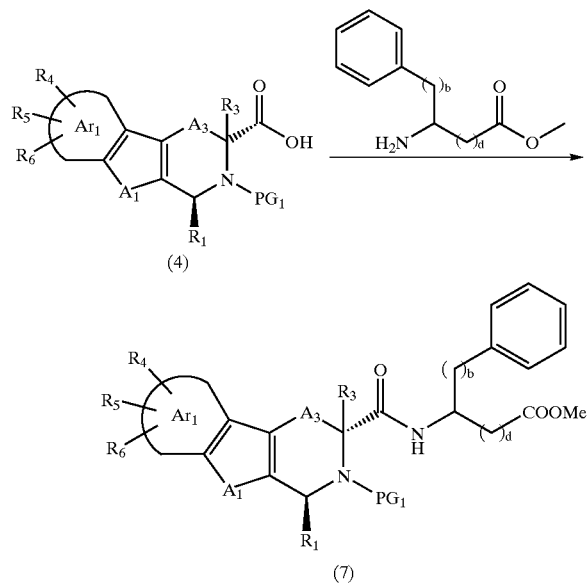

(4)

(7)

In another embodiment, the ester group in compound (7) (Scheme 6) can be hydrolyzed using a base such as, but not limited to, LiOH or NaOH in a mixture of aqueous and organic solvents such as THF, methanol, at temperature ranging from room temperature to 60° C. to provide the free carboxylic acid (8). In this instance, b may be an integer such as, but not limited to, 1, 2, or 3.

Scheme 6

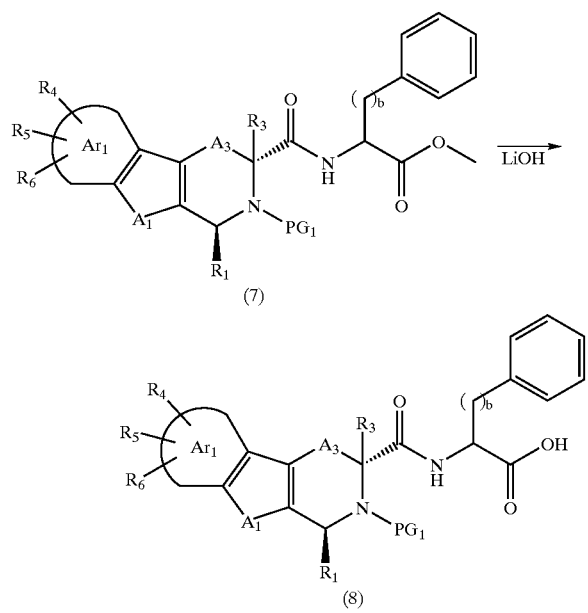

(7)

(8)

In another embodiment, the aryl esters (7) (Scheme 7) may be reduced to alcohols with hydrides such as, but not limited to, diisobutylaluminum hydride or LiAlH$_4$ using THF as the solvent at temperatures ranging from −25° C. to room temperature to afford aryl alcohols (9). Alcohols (9) can be alkylated with an alkyl halide such as, but not limited to, $R_{41}$—X in the presence of base such as, but not limited to, sodium hydride, potassium tert-butoxide, potassium carbonate using DMF, THF, acetonitrile as the solvent at temperatures ranging from 50° C. to 100° C. to afford ethers (10). $R_{41}$ in this instance is a group such as, but not limited to, -alkyl or -alkylene-aryl, and 6 is an integer from 1 to 6.

Scheme 7

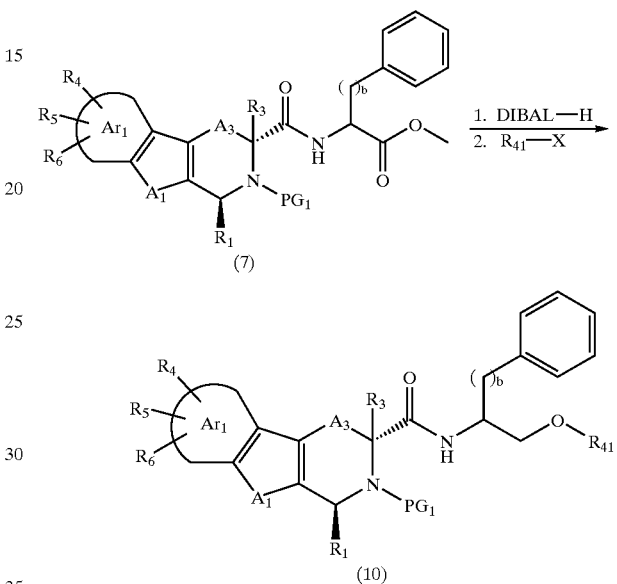

(7)

(10)

In another embodiment, the free acid group in compound (8) (Scheme 8) can be employed in the formation of amides, such as aromatic and aliphatic carboxy amides. This transformation can be accomplished using standard methods. These methods include converting the desired acid into activated acid and reacting with amine. Methods to activate the carboxylic acid include reacting the acid with one or more equivalents of DCC/DIEA with or without one or more molar equivalents of HOBt in a suitable solvent such as dichloromethane or dimethylformamide at temperatures ranging from 0° C. to room temperature, to afford compound (11). $R_{42}$ in this instance is a group such as but not limited to -alkyl or -alkylene-aryl. b and f are integers ranging from 1 to 6.

Scheme 8

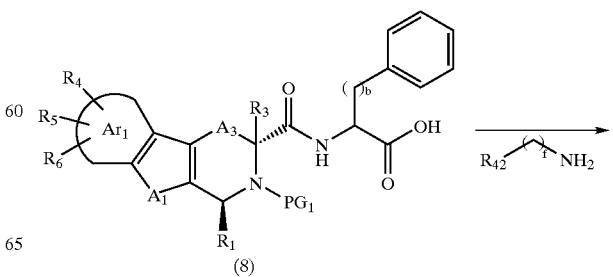

(8)

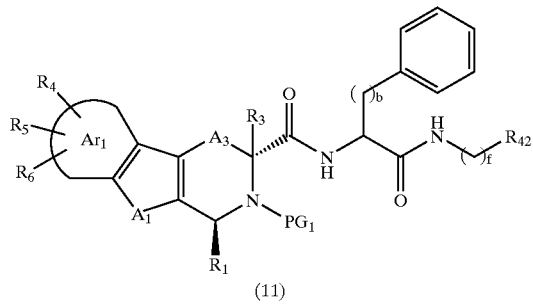

(11)

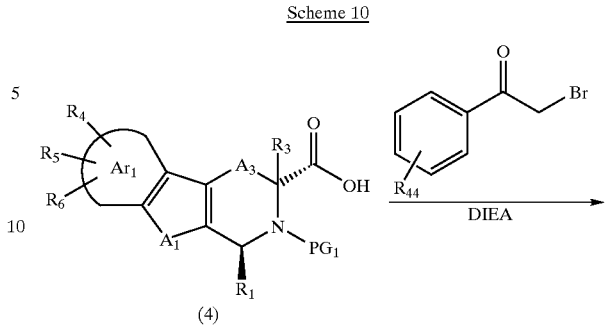

(4)

In another embodiment, the free acid group in compound (8) (Scheme 9) can be employed in formation of esters, such as aromatic and aliphatic carboxy esters. This transformation can be accomplished using standard methods. These methods include converting the desired acid into activated acid and reacting with an alcohol. Methods to activate the carboxylic acid include reacting the acid with one or more equivalents of DCC/DIEA in the presence or absence of DMAP, with or without one or more molar equivalents of hydroxy benzotriazole in a suitable solvent such as dichloromethane or dimethylformamide at temperartures ranging from 0° C. to room temperature, to afford compound (12). $R_{43}$ in this instance is a group such as, but not limited to, -alkyl or -alkylene-aryl. b and g are integers ranging from 1 to 6.

Scheme 9

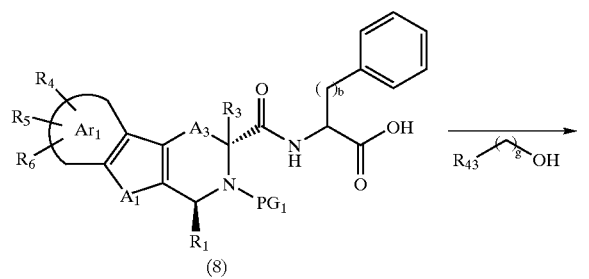

(8)

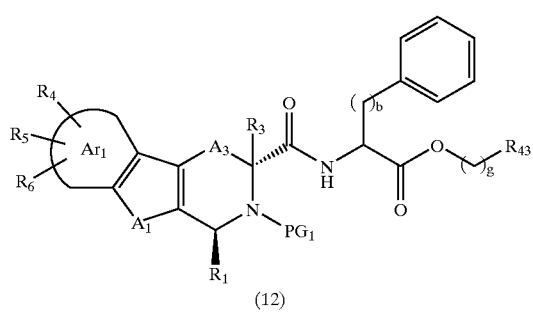

(12)

In another embodiment protected amino acid (4) (Scheme 10) can be treated with aryl acyl bromides (R=H, Me, Ph, Cl, F, Br, and O—R) in the presence of base such as DIEA, TEA or DBU in an polar solvents such as THF or DMF to afford keto-ester (13). $R_{44}$ in this instance may be a group such as, but not limited to, those defined for $R_4$.

(13)

In another embodiment, the nitrile group in compound (14) (Scheme 11) can be hydrolyzed in the presence of acidic conditions such 6N HCl or 0.8 $H_2SO_4$ in aqueous media at temperatures ranging from 80–120° C. to afford compound (15). $R_{45}$ in this instance is a group such as, but not limited to, those defined for $R_6$. h is an integer from 1 to 6.

Scheme 11

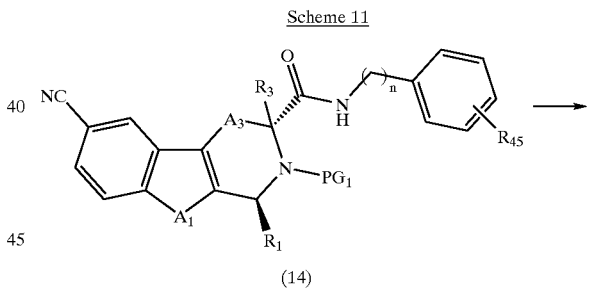

(14)

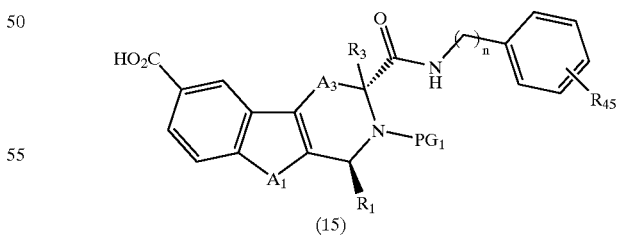

(15)

In another embodiment acid group in compound (15) (Scheme 12) can be esterified in the presence of acid such as HCl or 1,4 dioxane/HCl in solvent such as, but not limited to, methanol to afford compound (16). $R_{45}$ in this instance is a group such as but not limited to those defined for $R_6$. h is an integer ranging from 1 to 6.

Scheme 12

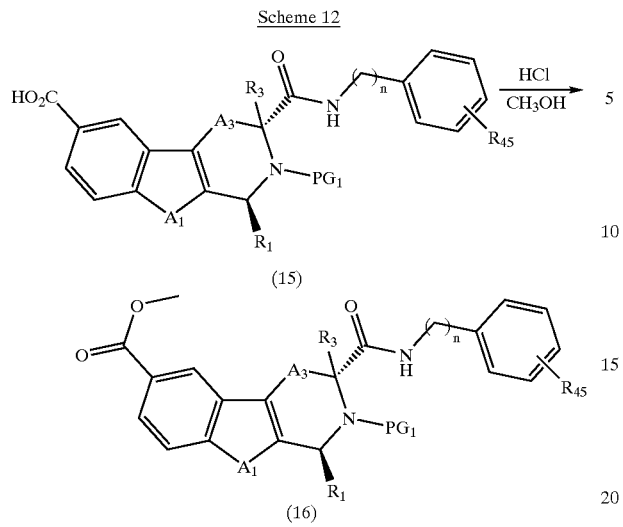

(15)

(16)

In another embodiment, the free acid group in compound (15) (Scheme 13) was used in the formation of amides, such as aromatic and aliphatic carboxy amides. This transformation can be accomplished using standard methods. These methods include converting the desired acid into activated acid and reacting with amine. Methods to activate the carboxylic acid include reacting the acid with one or more equivalents of DCC/DIEA with or without one or more molar equivalents of HOBt in a suitable solvent such as dichloromethane or dimethylformamide at temperatures ranging from 0° C. to room temperature, to afford compound (17). $R_{46}$ in this instance is a group such as, but not limited to, -alkyl or -alkylene-aryl. j and k are integers ranging from 1 to 6. $R_{47}$ in this instance is a group such as but not limited to those defined for $R_6$.

Scheme 13

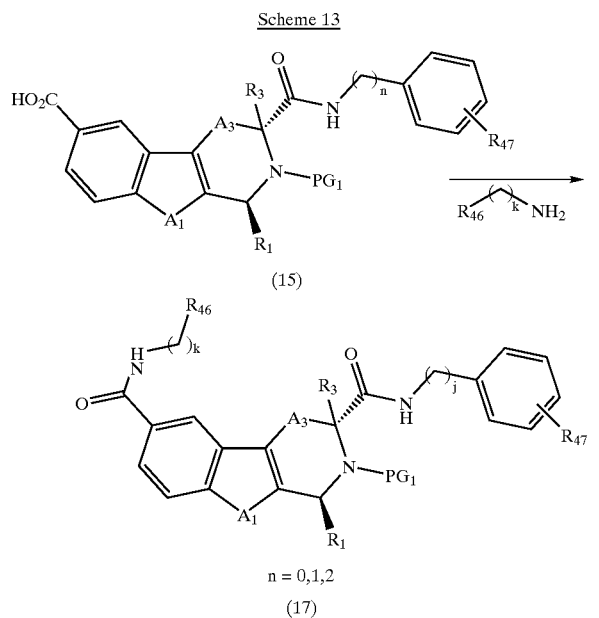

(15)

n = 0,1,2

(17)

In another embodiment alcohol group in compound (18) (Scheme 14) was oxidized to a ketone in the presence of chromium reagents such as pyridinium chlorochromate or pyridinium dichromate in a solvent such as dichloromethane to afford ketone (19). j and k, in this instance, are integers ranging from 1 to 6.

Scheme 14

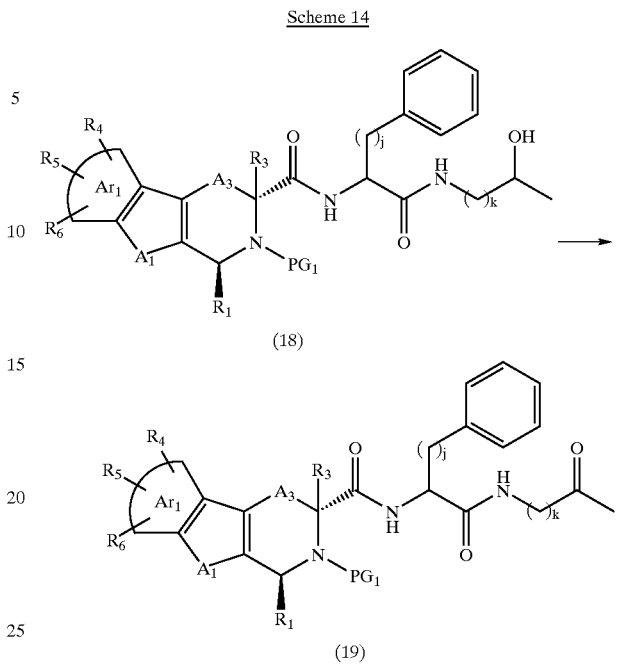

(18)

(19)

In the above schemes, "$PG_1$" represents an amino protecting group. The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups ($PG_1$ as used herein) such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In the above schemes, "$PG_2$" represents carboxyl protecting group. The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the methyl group, the ethyl group, the allyl group, the trimethylsilylethoxymethyl group, the 2,2,2-trichloroethyl group, the benzyl group, and the trialkylsilyl group, examples of such being trimethylsilyl, tert-butyidimethylsilyl, phenyidimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The compounds of the present invention are inhibitors of protein tyrosine phosphatases (PTPases). The invention described herein is additionally directed to pharmaceutical compositions and methods of inhibiting PTPase activity in a mammal, which methods comprise administering, to a mammal in need of inhibition of PTPase activity, a therapeutically defined amount of a compound of formula (I), defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

Thus, the present invention provides a method of inhibiting a PTPase, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit a PTPase. A PTPase-inhibiting amount can be an amount that reduces or inhibits a PTPase activity in the subject.

Additionally provided is a pharmaceutical composition comprising a pharmaceutically acceptable carrier and a pharmacologically effective amount of a compound of the present invention sufficient to treat type I diabetes.

Further, the present invention provides a pharmaceutical composition comprising a pharmaceutically acceptable carrier and a pharmacologically effective amount of a compound of the present invention sufficient to treat type II diabetes.

Further, the present invention provides a pharmaceutical composition comprising a pharmaceutically acceptable carrier and a pharmacologically effective amount of a compound of the present invention sufficient to treat immune dysfunction.

Further, the present invention provides a pharmaceutical composition comprising a pharmaceutically acceptable carrier and a pharmacologically effective amount of a compound of the present invention sufficient to treat AIDS.

Further, the present invention provides a pharmaceutical composition comprising a pharmaceutically acceptable carrier and a pharmacologically effective amount of a compound of the present invention sufficient to treat autoimmune diseases Further, the present invention provides a pharmaceutical composition comprising a pharmaceutically acceptable carrier and a pharmacologically effective amount of a compound of the present invention sufficient to treat glucose intolerance.

Further, the present invention provides a pharmaceutical composition comprising a pharmaceutically acceptable carrier and a pharmacologically effective amount of a compound of the present invention sufficient to treat obesity.

Further, the present invention provides a pharmaceutical composition comprising a pharmaceutically acceptable carrier and a pharmacologically effective amount of a compound of the present invention sufficient to treat cancer.

Further, the present invention provides a pharmaceutical composition comprising a pharmaceutically acceptable carrier and a pharmacologically effective amount of a compound of the present invention sufficient to treat psoriasis.

Further, the present invention provides a pharmaceutical composition comprising a pharmaceutically acceptable carrier and a pharmacologically effective amount of a compound of the present invention sufficient to treat allergic diseases Further, the present invention provides a pharmaceutical composition comprising a pharmaceutically acceptable carrier and a pharmacologically effective amount of a compound of the present invention sufficient to treat infectious diseases.

Further, the present invention provides a pharmaceutical composition comprising a pharmaceutically acceptable carrier and a pharmacologically effective amount of a compound of the present invention sufficient to treat inflammatory diseases.

Further, the present invention provides a pharmaceutical composition comprising a pharmaceutically acceptable carrier and a pharmacologically effective amount of a compound of the present invention sufficient to treat diseases involving the modulated synthesis of growth hormone.

Further, the present invention provides a pharmaceutical composition comprising a pharmaceutically acceptable carrier and a pharmacologically effective amount of a compound of the present invention sufficient to treat diseases involving the modulated synthesis of growth factors or cytokines which affect the production of growth hormone.

Further, the present invention provides a pharmaceutical composition comprising a pharmaceutically acceptable carrier and a pharmacologically effective amount of a compound of the present invention sufficient to treat Alzheimer's disease.

The compounds of the present invention can be administered to subjects in need of inhibition of PTPase activity. Such subjects can include, for example, horses, cows, sheep, pigs, mice, dogs, cats, primates such as chimpanzees, gorillas, rhesus monkeys, and, most preferably humans.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention. Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as—COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1–19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug therof, and one or more pharmaceutically acceptable carriers, excipients, or diluents.

The compounds of the present invention selectively act as inhibitors of one PTPase in preference to one or more other PTPases, and therefore may posess advantage in the treatment of one or more PTPase-mediated disease in preference to others.

Thus, in a further aspect, the present invention provides a method for the inhibition of PTPases. In a preferred embodiment of this aspect, the present invention provides a method for treating a disease states including diabetes, cancer, inflammation, Alzheimer's disease, psoriasis, or graft versus host disease, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of PTPase-mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (I).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

The following is a non-exhaustive listing of adjuvants and additional therapeutic agents which may be utilized in combination with the PTPase inhibitors of the present invention:

Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins Pharmacologic Classifications of Treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic Classifications of Treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone, Rosiglitazone, Pioglitazone
4. Insulin Pharmacologic classifications of treatment for Alzheimer's Disease

| | |
|---|---|
| 1. Cholinesterase Inhibitor: | Tacrine, Donepezil |
| 2. Antipsychotics: | Haloperidol, Thioridazine |
| 3. Antidepressants: | Desipramine, Fluoxetine, Trazodone, Paroxetine |
| 4. Anticonvulsants: | Carbamazepine, Valproic acid |

In a further preferred embodiment, the present invention provides a method of treating PTPase mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted.

Procedure A 1 equivalent of amine methyl ester and 1.1 equivalent of aromatic or aliphatic aldehyde is suspended in anhydrous toluene (0.1–0.5M). The reaction mixture is refluxed for 6–8 hours over activated molecular sieves (4 Angstrom) with an access of TFA (~2.5 equivalents). When the cyclization is complete, the reaction mixture is poured into ice water and neutralized to basic with an excess of aqueous NaOH. The aqueous layer is further extracted with EtOAc, the organic layers combined, washed with brine, and the organic layer dried over sodium sulfate. The solvent is removed in vacuo and the crude product purified by flash chromatography on silica gel to give the final product, which is typically a mixture of cis and trans (50:50).

Procedure B 1 equivalent of amine methyl ester and 1.1 equivalent of aromatic or aliphatic aldehyde is suspended in anhydrous benzene or toluene or dichloromethane (0.1–0.5M). The reaction mixture is refluxed over activated molecular sieves (4 Angstrom) with a trace of TFA (<5 mole %). After one hour an access of TFA (~2.5 equivalents) is added and reflux is continued for further 3–6 hours. When the cyclization is complete, the reaction mixture is poured into ice water and neutralized to basic with an excess of aqueous NaOH. The aqueous layer is further extracted with EtOAc, the organic layers combined, washed with brine, and the organic layer dried over sodium sulfate. The solvent is removed in vacuo, and the crude product purified by flash chromatography on silica gel to give the final product, which is typically a mixture of cis and trans. Further two isomers were separated through silica column chromatography, elution with ethyl acetate-hexane.

Procedure C 1 equivalent of amine methyl ester and 1.1 equivalent of aromatic or aliphatic aldehyde is suspended in anhydrous dichloromethane (0.1–0.5M). The reaction mixture is stirred for 6 hours at 0° C. to −70° C., with a trace of TFA (<5 mole %) over activated molecular sieves (4 Angstrom). After complete formation of imine, an excess of TFA (~2.5 equivalents) is added and reaction is continued for further 9–12 hours at 0 to −70° C. When the cyclisation is complete, the reaction mixture is poured into ice water and made basic with an excess of aqueous NaOH. The aqueous layer is further extracted with dichloromethane, the organic layers combined, washed with brine, and the organic layer dried over sodium sulfate. The solvent is removed in vacuo and the crude product purified by flash chromatography on silica gel to give the final product, which is typically a mixture of cis and trans. The two isomers may be separated through silica column chromatography, elution with hexane: ethyl acetate.

Procedure D: Protection of Amino Ester 1 equivalent of amino ester is suspended in anhydrous THF or dioxane (0.1–0.5 M), to which was added 1.4 equivalents of DIEA or $Na_2CO_3$ and 1.5 equivalents of di-tert-butyl-dicarbonate. The mixture is stirred for 6 hours and diluted with water and the layers were separated. The aqueous layer is further extracted with EtOAc, the organic layers combined, washed with brine, and the organic layer dried over sodium sulfate. The solvent is removed in vacuo, and the crude product purified by to flash chromatography on silica gel to give the final product.

General Procedure E: Hydrolysis of Protected Ester

The ester (1 equivalent) is suspended in a mixture of $MeOH:THF:H_2O$ (1:1:1; 0.1–0.2 M). LiOH (10–15 eq) is added and the mixture stirred at 40° C. for 3–6 hours. The solution is acidified with 10% citric acid, and extracted with ethyl acetate. The organic extracts are combined, washed with brine, dried over $Na_2SO_4$, and the solvent removed in vacuo. The residue is purified by silica gel chromatography to yield the final compound.

Procedure F: Coupling of Carboxylic Acid and Amine

To a solution of carboxylic acid (1.25 equivalents) in DMF (0.1–0.5 M), HBTU (1.25 equivalents) is added followed by DIEA (1.25 equivalents) and the appropriate amine (1 equivalent). The reaction mixture is then stirred at room temperature for 2–4 hours, and is diluted with water/EtOAc and the layers separated. The aqueous layer is re-extracted with EtOAc and the organic layers combined, washed with saturated $Na_2CO_3$ and brine. The organic phase is then dried over $Na_2SO_4$, filtered, and the filtrate is concentrated and purified by silica gel chromatography to afford the amide derivative.

Procedure G: Removal of the Boc-Protecting Group

The protected compound is stirred in 4N HCl/dioxane for 1 hour. The solvent removed, and the product triturated several times with ether to afford the desired compound.

Procedure H: Hydrolysis of Nitrile

The nitrile(1equivalent) is suspended in a mixture of 6 N HCl in aqueous media and the mixture is refluxed for 6–12 hours. The solution is neutralized and extracted with ethyl acetate. The organic extracts are combined, washed with brine, dried over $Na_2SO_4$, and the solvent removed in vacuo. The residue is purified by silica gel chromatography to yield the final compound.

Procedure I: Synthesis of Methyl Ester

The carboxylic acid is stirred in 4N HCl/dioxane and methanol under reflux temperature for 4–6 hours. The solvent is removed, and the product triturated several times with ether to afford the desired compound.

Procedure J: O-alkylation of Aryl Alcohol

To a solution of hydroxy compound (1 equivalent) in anhydrous DMF (0.8–.1.5 M) is added freshly ground $K_2CO_3$ (1.5 equivalents), followed by an alkyl or aryl halide (1.1 equivalents). The reaction mixture is stirred at 80° C. for 2–6 hours, it was diluted with water/EtOAc and the layers separated. The aqueous layer is further extracted with EtOAc and the organic layers combined and dried over $Na_2SO_4$. The solvent is removed in vacuo and the residue is purified by silica gel chromatography to yield the final product.

Procedure K: Reduction of Methyl Ester

A solution of methyl ester compound (1 equivalent) in anhydrous THF (0.8–.1.5 M) is cooled to 0° C., and is treated with DIBAL-H in THF solution (2.0 equivalents). The reaction mixture is stirred at 0° C. for 2–4 hours, quenched, and treated with saturated $Na_2SO_4$ solution and diluted with water/EtOAc and the layers separated. The aqueous layer is further extracted with EtOAc and the organic layers combined and dried over $Na_2SO_4$. The solvent is removed in vacuo and the residue is purified by silica gel chromatography to yield the final product.

Procedure L: Formation of Keto Ester 1 equivalent of a protected amino acid is dissolved in anhydrous DMF (0.2–0.3 M), to which is added DIEA (1 equivalent) and either 1 equivalent of a bromo- or chloroketone. The mixture is stirred at room temperature for 30 minutes, diluted with water/ethyl acetate and the layers separated. The aqueous layer is further extracted with EtOAc. The organic layers are combined, washed with saturated citric acid, brine, and the organic layer dried over $Na_2SO_4$, and the solvent is removed in vacuo to give the crude product, which is used without further purification.

Procedure M: Oxidation of Alcohol

To a solution of alcohol (1 equivalent) in anhydrous dichloromethane (0.8–.1.5 M) is cooled to 0° C. and is added pyridinum dichromate (2.0 equivalents). The reaction mixture is stirred at room temperature for 6–8 hours. The reaction mixture is diluted with water/EtOAc and the layers separated. The aqueous layer is further extracted with EtOAc and the organic layers combined and dried over $Na_2SO_4$. The solvent is removed in vacuo and the residue purified by silica gel chromatography to yield the final product.

EXAMPLES

Example 1

The compound Benzyl 1-(1,1'-biphenyl-4-yl)-1,2,3,4-tetrahydro-beta-carboline-3-carboxamide was prepared following procedure A, starting from DL-tryptophan methyl ester and 4-biphenyl carboxaldehyde. The resulting tetrahydro-β-carboline amino ester was protected according to procedure D and was hydrolyzed following procedure E. Thus obtained acid was treated with benzyl amine as described in procedure F to afford the amide derivative and was de-protected according to procedure G to yield Benzyl 1-(1,1'-biphenyl-4-yl)-1,2,3,4-tetrahydro-beta-carboline-3-carboxamide. LC: $T_r$ 2.24 min, MS: 458 (M+H)$^+$

Example 2

The compound 3-Fluorophenyl 1-(1,1'-biphenyl-4-yl)-2-tert-butoxycarbonyl-1,2,3,4-tetrahydro-beta-carboline-3-carboxamide was prepared following procedure A, starting from DL-tryptophan methyl ester and 4-biphenyl carboxaldehyde. The resulting tetrahydro-β-carboline amino ester was protected according to procedure D and was hydrolyzed following procedure E. Thus obtained acid was treated with 3-fluoro aniline as described in procedure F to afford the 3-Fluorophenyl 1-(1,1'-biphenyl-4-yl)-2-tert-butoxycarbonyl-1,2,3,4-tetrahydro-beta-carboline-3-carboxamide. LC: $T_r$ 2.61 min, MS: 562 (M+H)$^+$

Example 3

The compound 2-(3-Fluorophenyl)-1-ethyl 1-(1,1'-Biphenyl-4-yl)-1,2,3,4-tetrahydro-beta-carboline-3-carboxamide was prepared following procedure C, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 2 (3-fluorophenyl)ethylamine as described in procedure F to afford the amide derivative and was deprotected according to procedure G to yield 2-(3-Fluorophenyl)-1-ethyl 1-(1,1'-Biphenyl-4-yl)-1,2,3,4-tetrahydro-beta-carboline-3-carboxamide. LC: $T_r$ 2.07 min, MS: 490 (M+H)$^+$

Example 4

The compound 1,1'-Biphenyl-4-yl (1S,3S)-1-(1,1'-Biphenyl-4-yl)-1,2,3,4-tetrahydro-beta-carboline-3-carboxamide was prepared following procedure C, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-amino biphenyl as described in procedure F to afford the amide derivative and was de-protected according to procedure G to yield 1,1'-Biphenyl-4-yl (1S,3S)-1-(1,1'-Biphenyl-4-yl)-1,2,3,4-tetrahydro-beta-carboline-3-carboxamide. LC: $T_r$ 2.19 min, MS: 520 (M+H)$^+$

Example 5

The compound 1-Benzylcarbamoyl-1-(1,1'-Biphenyl-4-yl)methyl (1S,3S)-1-(1,1'-Biphenyl-4-yl)-1,2,3,4-tetrahydro-beta-carboline-3-carboxamide was prepared following procedure C, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with methyl ester of amino biphenyl acetic acid as described in procedure F to afford the amide derivative and was hydrolyzed following procedure E and acid was coupled with benzyl amine as described in procedure F and was de-protected according to procedure G to yield 1-Benzylcarbamoyl-1-(1,1'-Biphenyl-4-yl)methyl (1S,3S)-1-(1,1'-Biphenyl-4-yl)-1,2,3,4-tetrahydro-beta-carboline-3-carboxamide. LC: $T_r$ 2.30 min, MS: 667 (M+H)$^+$

Example 6

The compound 2,4,6-Trimethoxybenzyl (1S,3R)-1-Cyclohexyl-1,2,3,4-tetrahydro-beta-carboline-3-carboxamide was prepared following procedure B, starting from L-tryptophan methyl ester and cyclohexane carboxaldehyde. The resulting tetrahydro-β-carboline amino ester was protected according to procedure D and was hydrolyzed following procedure E. Thus obtained acid was treated with 2,4,6-trimethoxy bezylamine hydrochloride as described in procedure F to afford the amide derivative and was de-protected according to procedure G to yield 2,4,6-Trimethoxybenzyl (1S,3R)-1-Cyclohexyl-1,2,3,4-tetrahydro-beta-carboline-3-carboxamide. LC: $T_r$ 2.12 min, MS: 478 (M+H)$^+$ Example 7

The compound 4-tert-Butylbenzyl (1S,3R)-1-(1,1'-Biphenyl-4-yl)-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-tert-butyl benzyl amine as described in procedure F to afford the amide derivative and was de-protected according to procedure G to yield 4-tert-Butylbenzyl (1S,3R)-1-(1,1'-Biphenyl-4-yl)-1,2,3,4-tetrahydro-beta-carboline-3-carboxamide. LC: $T_r$ 2.31 min, MS: 514 (M+H)$^+$ Example 8

The compound 2,4,6-Trimethoxybenzyl (1S,3R)-1-(4-bromophenyl)-1,2,3,4-tetrahydro-beta-carboline-3-carboxamide was prepared following procedure B, starting from L-tryptophan methyl ester and 4-bromo benzaldehyde. The resulting tetrahydro-β-carboline amino ester was protected according to procedure D and was hydrolyzed following procedure E. Thus obtained acid was treated with 2,4,6-trimethoxy bezylamine hydrochloride as described in procedure F to afford the amide derivative and was de-protected according to procedure G to yield 2,4,6-Trimethoxybenzyl (1S,3R)-1-(4-bromophenyl)-1,2,3,4-tetrahydro-beta-carboline-3-carboxamide. LC: $T_r$ 2.12 min, MS: 551 (M+H)$^+$ Example 9

The compound (5-methyl-2-furan)methyl (1S,3R)-1-(1,1'-Biphenyl-4-yl)-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 2-amino methyl 5-methyl furan as described in procedure F to afford the amide derivative and was de-protected according to procedure G to yield (5-methyl-2-furan)methyl (1S,3R)-1-(1,1'-Biphenyl-4-yl)-1,2,3,4-tetrahydro-beta-carboline-3-carboxamide. MS: 462 (M+H)$^+$ Example 10

The compound 4-Chlorobenzyl (1S,3R)-1-(2,4-dichlorophenyl)-1,2,3,4-tetrahydro-beta-carboline-3-carboxamide was prepared following procedure B, starting from L-tryptophan methyl ester and 2,4-dichloro benzaldehyde. The resulting tetrahydro-β-carboline amino ester was protected according to procedure D and was hydrolyzed following procedure E. Thus obtained acid was treated with 4-chloro benzyl amine as described in procedure F to afford the amide derivative and was de-protected according to procedure G to yield 4-Chlorobenzyl (1S,3R)-1-(2,4-dichlorophenyl)-1,2,3,4-tetrahydro-beta-carboline-3-carboxamide. MS: 484 (M+H)$^+$ Example 11

The compound 2,4,6-Trimethoxybenzyl (1S,3R)-1-(4-benzyloxyphenyl)-1,2,3,4-tetrahydro-beta-carboline-3-carboxamide was prepared following procedure B, starting from L-tryptophan methyl ester and 4-benzyloxy benzaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G to yield 2,4,6-Trimethoxybenzyl (1S,3R)-1-(4-benzyloxyphenyl)-1,2,3,4-tetrahydro-beta-carboline-3-carboxamide. LC: $T_r$ 2.37 min, MS: 578 (M+H)$^+$ Example 12

The compound 4-Carboxybenzyl (1S,3R)-1-(1,1'-Biphenyl-4-yl)-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-carboxy benzylamine as described in procedure F to afford the amide derivative and was de-protected according to procedure G to yield 4-Carboxybenzyl (1S,3R)-1-(1,1'-Biphenyl-4-yl)-1,2,3,4-tetrahydro-beta-carboline-3-carboxamide. LC: $T_r$ 2.59 min, MS: 502 (M+H)$^+$ Example 13

The compound 2,4,6-Trimethoxybenzyl (1S,3R)-1-(4-(4-carboxy)benzyloxyphenyl)-2-tert-butoxycarbonyl-1,2,3,4-tetrahydro-beta-carboline-3-carboxamide was prepared following procedure B, starting from L-tryptophan methyl ester and 4 (4-carboxy)benzyloxy benzaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the 2,4,6-Trimethoxybenzyl (1S,3R)-1-(4-(4-carboxy)benzyloxyphenyl)-2-tert-butoxycarbonyl-1,2,3,4-tetrahydro-beta-carboline-3-carboxamide. LC: $T_r$ 2.35 min, MS: 722 (M+H)$^+$ Example 14

The compound 4-(methoxycarbonylmethyl)-1-phenyl (1S,3R)-1-(1,1'-Biphenyl-4-yl)-2-tert-butoxycarbonyl-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-amino phenyl acetate as described in procedure F to afford the 4-(methoxycarbonylmethyl)-1-phenyl (1S,3R)-1-(1,1'-Biphenyl-4-yl)-2-tert-butoxycarbonyl-1,2,3,4-tetrahydro-beta-carboline-3-carboxamide. MS: 616 (M+H)$^+$ Example 15

The compound 2,4,6-Trimethoxybenzyl 1-(1,1'-Biphenyl-4-yl)-6-methylcarboximidatoyl-1,2,3,4-tetrahydro-beta-carboline-3-carboxamide was prepared following procedure A, starting from D L-5 cyano tryptophan methyl ester and 4-biphenyl carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G and cyano group was hydrolyzed following procedure H to yield 2,4,6-Trimethoxybenzyl 1-(1,1'-Biphenyl-4-yl)-6-methylcarboximidatoyl-1,2,3,4-tetrahydro-beta-carboline-3-carboxamide. LC: $T_r$ 1.97 min, MS: 605 (M+H)$^+$ Example 16

The compound 2,4,6-Trimethoxybenzyl 1-(1,1'-Biphenyl-4-yl)-6-methoxycarbonyl-1,2,3,4-tetrahydro-beta-carboline-3-carboxamide was prepared following procedure A, starting from D L-5 cyano tryptophan methyl ester and 4-biphenyl carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G and cyano group was hydrolyzed following procedure H and acid was converted in to ester following the procedure I to yield 2,4,6-Trimethoxybenzyl 1-(1,1'-Biphenyl-4-yl)-6-methoxycarbonyl-1,2,3,4-tetrahydro-beta-carboline-3-carboxamide. LC: $T_r$ 2.23 min, MS: 606 (M+H)$^+$ Example 17

The compound 4-(Carboxymethyl)-1-phenyl (1S,3R)-1-(1,1'-Biphenyl-4-yl)-2-tert-butoxycarbonyl-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-amino phenyl acetate as described in procedure F to afford amide derivative and obtained ester was hydrolyzed following procedure E to yield 4-(Carboxymethyl)-1-phenyl (1S,3R)-1-(1,1'-Biphenyl-4-yl)-2-tert-butoxycarbonyl-1,2,3,4-tetrahydro-beta-carboline-3-carboxamide. LC: $T_r$ 2.62, MS: 602 (M+H)$^+$ Example 18

4-(Carboxymethyl)-1-phenyl (1S,3R)-1-(1,1'-Biphenyl-4-yl)-1,2,3,4-tetrahydro-beta-carboline-3-carboxamide was prepared starting from the compound described in example 17 following procedure G. LC: $T_r$ 2.15, MS: 502 (M+H)$^+$ Example 19

The compound 4-Methoxycarbonyl-1-cyclohexyl (1S,3R)-1-(1,1'-Biphenyl-4-yl)-2-tert-butoxycarbonyl-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 4-amino cyclohexane carboxylate as described in procedure F to yield 4-Methoxycarbonyl-1-cyclohexyl (1S,3R)-1-(1,1'-Biphenyl-4-yl)-2-tert-butoxycarbonyl-1,2,3,4-tetrahydro-beta-carboline-3-carboxamide. LC: $T_r$ 2.83, MS: 608 (M+H)$^+$ Example 20

The compound 2(4-(methoxycarbonylmethoxy)-phenyl-1-ethyl (1S,3R)-1-(1,1'-Biphenyl-4-yl)-2-tert-butoxycarbonyl-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with tyramine as described in procedure F and resulting alcohol was treated with bromo methyl acetate following the procedure J to yield 2(4-(methoxycarbonylmethoxy)-phenyl-1-ethyl (1S,3R)-1-(1,1'-Biphenyl-4-yl)-2-tert-butoxycarbonyl-1,2,3,4-tetrahydro-beta-carboline-3-carboxamide. LC: $T_r$ 2.70, MS: 670 (M+H)$^+$ Example 21

The compound (5-Methyl-2-furan)methyl (1R,3S)-1-(1,1'-Biphenyl-4-yl)-1,2,3,4-tetrahydro-beta-carboline-3-carboxamide was prepared following procedure C, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with 2-amino methyl 5-methyl furan as described in procedure F to afford the amide derivative and was de-protected according to procedure G to yield example yield (5-Methyl-2-furan)methyl (1R,3S)-1-(1,1'-Biphenyl-4-yl)-1,2,3,4-tetrahydro-beta-carboline-3-carboxamide. MS: 462 (M+H)$^+$ Example 22

The compound 2,4,6-Trimethoxybenzyl 1-Cyclopentyl-1,2,3,4-tetrahydro-beta-carboline-3-carboxamide was prepared following procedure B, starting from L-tryptophan methyl ester and cyclopentane carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G to yield example yield 2,4,6-Trimethoxybenzyl 1-Cyclopentyl-1,2,3,4-tetrahydro-beta-carboline-3-carboxamide. MS: 464 (M+H)$^+$ Example 23

The compound 2,4,6-Trimethoxybenzyl 1-(1,1'-Biphenyl-4-yl)-6-carboxy-1,2,3,4-tetrahydro-beta-carboline-3-carboxamide was prepared following procedure A, starting from D L-5 cyano tryptophan methyl ester and 4-biphenyl carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G and cyano group was hydrolyzed following procedure H to yield 2,4,6-Trimethoxybenzyl 1-(1,1'-Biphenyl-4-yl)-6-carboxy-1,2,3,4-tetrahydro-beta-carboline-3-carboxamide. MS: 592 (M+H)$^+$ Example 24

The compound 1-Methoxycarbonyl-1-(1,1'-Biphenyl-4-yl)methyl (3R)-1-(1,1'-Biphenyl-4-yl)-1,2,3,4-tetrahydro-beta-carboline-3-carboxamide was prepared following procedure B, starting from L-tryptophan methyl ester and 4-biphenyl carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G to yield 1-Methoxycarbonyl-1-(1,1'-Biphenyl-4-yl)methyl (3R)-1-

(1,1'-Biphenyl-4-yl)-1,2,3,4-tetrahydro-beta-carboline-3-carboxamide. LC: $T_r$ 2.23 min, MS: 592 (M+H)$^+$ Example 25

The compound 2,4,6-Trimethoxybenzyl (1R,3R)-1-{4-[(E)-2-phenylvinyl]phenyl}-1,2,3,4-tetrahydro-beta-carboline-3-carboxamide was prepared following procedure C, starting from L-tryptophan methyl ester and trans 4-stilbene carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G to yield 2,4,6-Trimethoxybenzyl (1R,3R)-1-{4-[(E)-2-phenylvinyl]phenyl}-1,2,3,4-tetrahydro-beta-carboline-3-carboxamide. MS: 574 (M+H)$^+$ Example 26

The compound 2,4,6-Trimethoxybenzyl (1S,3R)-1-{4-[(E)-2-phenylvinyl]phenyl}-1,2,3,4-tetrahydro-beta-carboline-3-carboxamide was prepared following procedure B, starting from L-trytophan methyl ester and trans 4-stilbene carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to afford the amide derivative and was de-protected according to procedure G to yield 2,4,6-Trimethoxybenzyl (1S,3R)-1-{4-[(E)-2-phenylvinyl]phenyl}-1,2,3,4-tetrahydro-beta-carboline-3-carboxamide. MS: 574 (M+H)$^+$ Example 27

The compound described in Example 23 was treated with butyl amine as described in procedure F to afford the amide derivative 2,4,6-Trimethoxybenzyl 1-(1,1'-Biphenyl-4-yl)-6-butylcarbamoyl-1,2,3,4-tetrahydro-beta-carboline-3-carboxamide. LC: $T_r$ 2.26 min, MS: 647 (M+H)$^+$ Example 28

The compound 2,4,6-Trimethoxybenzyl (1S,3R)-1-(Indol-3-yl)-2-tert-butoxycarbonyl-1,2,3,4-tetrahydro-beta-carboline-3-carboxamide was prepared following procedure B, starting from D-tryptophan methyl ester and indole 3-carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to yield 2,4,6-Trimethoxybenzyl (1S,3R)-1-(Indol-3-yl)-2-tert-butoxycarbonyl-1,2,3,4-tetrahydro-beta-carboline-3-carboxamide. LC: $T_r$ 2.52 min, MS: 611 (M+H)$^+$ Example 29

The compound 2,4,6-Trimethoxybenzyl (1R,3R)-1-(Indol-3-yl)-2-tert-butoxycarbonyl-1,2,3,4-tetrahydro-beta-carboline-3-carboxamide was prepared following procedure C, starting from D-tryptophan methyl ester and indole 3-carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to yield 2,4,6-Trimethoxybenzyl (1R,3R)-1-(Indol-3-yl)-2-tert-butoxycarbonyl-1,2,3,4-tetrahydro-beta-carboline-3-carboxamide. LC: $T_r$ 2.40 min, MS: 611 (M+H)$^+$ Example 30

The compound 2,4,6-Trimethoxybenzyl (1S,3R)-1-(Indol-3-yl)-1,2,3,4-tetrahydro-beta-carboline-3-carboxamide was prepared following procedure B, starting from L-tryptophan methyl ester and indole 3-carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to yield 2,4,6-Trimethoxybenzyl (1S,3R)-1-(Indol-3-yl)-1,2,3,4-tetrahydro-beta-carboline-3-carboxamide. LC: $T_r$ 2.31 min, MS: 611 (M+H)$^+$ Example 31

The compound 2,4,6-Trimethoxybenzyl (1R,3R)-1-(Indol-3-yl)-1,2,3,4-tetrahydro-beta-carboline-3-carboxamide was prepared following procedure C, starting from L-tryptophan methyl ester and indole 3-carboxaldehyde. The resulting tetrahydro-β-carboline amino ester was protected according to procedure D and was hydrolyzed following procedure E. Thus obtained acid was treated with 2,4,6-trimethoxy benzylamine hydrochloride as described in procedure F to yield 2,4,6-Trimethoxybenzyl (1R,3R)-1-(Indol-3-yl)-1,2,3,4-tetrahydro-beta-carboline-3-carboxamide. LC: $T_r$ 2.22 min, MS: 611 (M+H)$^+$ Example 32

The compound (R)-1-Methoxycarbonyl-1-(4-hydroxyphenyl)methyl (1S)-1-(1,1'-Biphenyl-4-yl)-1,2,3,4-tetrahydro-beta-carboline-3-carboxamide was prepared following procedure B, starting from L-trytophan methyl ester and 4-biphenyl carboxaldehyde. The resulting tetrahydro-β-carboline amino ester was protected according to procedure D and was hydrolyzed following procedure E. Thus obtained acid was treated with D-4-hydroxy phenyl glycine methyl ester as described in procedure F to afford the amide derivative and was de-protected according to procedure G to yield (R)-1-Methoxycarbonyl-1-(4-hydroxyphenyl)methyl (1S)-1-(1,1'-Biphenyl-4-yl)-1,2,3,4-tetrahydro-beta-carboline-3-carboxamide. LC: $T_r$ 2.00, MS: 532 (M+H)$^+$ Example 33

The compound (R)-1-Methoxycarbonyl-1-(4-hydroxyphenyl)methyl (1R)-1-( 1,1'-Biphenyl-4-yl)-2-tert-butoxycarbonyl-1,2,3,4-tetrahydro-beta-carboline-3-carboxamide was prepared following procedure C, starting from L-trytophan methyl ester and 4-biphenyl carboxaldehyde. The resulting tetrahydro-β-carboline amino ester was protected according to procedure D and was hydrolyzed following procedure E. Thus obtained acid was treated with D-4-hydroxy phenyl glycine methyl ester as described in procedure F to afford the amide derivative and was de-protected according to procedure G to yield (R)-1-Methoxycarbonyl-1-(4-hydroxyphenyl)methyl (1R)-1-(1,1'-Biphenyl-4-yl)-2-tert-butoxycarbonyl-1,2,3,4-tetrahydro-beta-carboline-3-carboxamide. LC: $T_r$ 2.46, MS: 532 (M+H)$^+$ Example 34

The compound 1-(1,1'-Biphenyl-4-yl)1-carboxymethyl (1S,3R)-1 Cyclohexyl-1,2,3,4-tetrahydro-beta-carboline-3-carboxamide was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G and was hydrolyzed following procedure E to yield 1-(1,1'-Biphenyl-4-yl)1-carboxymethyl (1S,3R)-1 Cyclohexyl-1,2,3,4-tetrahydro-beta-carboline-3-carboxamide. LC: $T_r$ 2.06 min, MS: 508 (M+H)$^+$ Example 35

The compound 1-(1,1'-Biphenyl-4-yl)1-carboxymethyl (1R,3R)-1 Cyclohexyl-1,2,3,4-tetrahydro-beta-carboline-3-carboxamide was prepared following procedure C, starting from L-trytophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G and was hydrolyzed following procedure E to yield 1-(1,1'-Biphenyl-4-yl)1-carboxymethyl (1R,3R)-1 Cyclohexyl-1,2,3,4-tetrahydro-beta-carboline-3-carboxamide. LC: $T_r$ 1.99 min, MS: 508 (M+H)$^+$ Example 36

The compound (R)-1-Methoxycarbonyl-1-(4-hydroxybenzyl)methyl (1S)-1-(1,1'-Biphenyl-4-yl)-1,2,3,4-tetrahydro-beta-carboline-3-carboxamide was prepared following procedure B, starting from L-trytophan methyl ester and 4-biphenyl carboxaldehyde. The resulting tetrahydro-β-carboline amino ester was protected according to procedure D and was hydrolyzed following procedure E. Thus obtained acid was treated with D-4-tyrosine methyl ester as described in procedure F to afford the amide derivative and was de-protected according to procedure G to yield (R)-1-Methoxycarbonyl-1-(4-hydroxybenzyl)methyl (1S)-1-(1,1'-Biphenyl-4-yl)-1,2,3,4-tetrahydro-beta-carboline-3-carboxamide. LC: $T_r$ 2.04, MS: 546 (M+H)$^+$ Example 37

The compound 1-Methoxycarbonyl-1-(1,1'-Biphenyl-4-yl)methyl (1S,3R)-1-Cyclohexyl-1,2,3,4-tetrahydro-beta-carboline-3-carboxamide was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G to yield 1-Methoxycarbonyl-1-(1,1'-Biphenyl-4-yl)methyl (1S,3R)-1-Cyclohexyl-1,2,3,4-tetrahydro-beta-carboline-3-carboxamide. LC: $T_r$ 2.19 min, MS: 522 (M+H)$^+$ Example 38

The compound 1-Methoxycarbonyl-1-(1,1'-Biphenyl-4-yl)methyl (1R,3R)-1-Cyclohexyl-1,2,3,4-tetrahydro-beta-carboline-3-carboxamide was prepared following procedure C, starting from L-trytophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G to yield 1-Methoxycarbonyl-1-(1,1'-Biphenyl-4-yl)methyl (1R,3R)-1-Cyclohexyl-1,2,3,4-tetrahydro-beta-carboline-3-carboxamide. LC: $T_r$ 2.13 min, MS: 522 (M+H)$^+$ Example 39

The compound 1-Carboxy-1-(1,1'-Biphenyl-4-yl)methyl (1S,3R)-1-(4-Bromophenyl)-1,2,3,4-tetrahydro-beta-carboline-3-carboxamide was prepared starting with the compound described in example 41 following procedure E. LC: $T_r$ 2.09 min, MS: 581 (M+H)$^+$ Example 40

The compound 1-Carboxy-1-(1,1'-Biphenyl-4-yl)methyl (1R,3R)-1-(4-Bromophenyl)-1,2,3,4-tetrahydro-beta-carboline-3-carboxamide was prepared starting with the compound described in example 42 following procedure E. LC: $T_r$ 2.03 min, MS: 581 (M+H)$^+$ Example 41

The compound 1-Methoxycarbonyl-1-(1,1'-Biphenyl-4-yl)methyl (1S,3R)-1-(4-Bromophenyl)-1,2,3,4-tetrahydro-beta-carboline-3-carboxamide was prepared following procedure B, starting from L-trytophan methyl ester and 4-bromo benzaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G to yield 1-Methoxycarbonyl-1-(1,1'-Biphenyl-4-yl)methyl (1S,3R)-1-(4-Bromophenyl)-1,2,3,4-tetrahydro-beta-carboline-3-carboxamide. LC: $T_r$ 2.22 min, MS: 595 (M+H)$^+$ Example 42

The compound 1-Methoxycarbonyl-1-(1,1'-Biphenyl-4-yl)methyl (1R,3R)-1-(4-Bromophenyl)-1,2,3,4-tetrahydro-beta-carboline-3-carboxamide was prepared following procedure C, starting from L-trytophan methyl ester and 4-bromo benzaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G to yield 1-Methoxycarbonyl-1-(1,1'-Biphenyl-4-yl)methyl (1R,3R)-1-(4-Bromophenyl)-1,2,3,4-tetrahydro-beta-carboline-3-carboxamide. LC: $T_r$ 2.13 min, MS: 595 (M+H)$^+$ Example 43

The compound described in Example 34 was treated with methylamine as described in procedure F to afford the amide derivative 1-Methylcarbamoyl-1-(1,1'-Biphenyl-4-yl)methyl (1S,3R)-1-Cyclohexyl-1,2,3,4-tetrahydro-beta-carboline-3-carboxamide. LC: $T_r$ 2.17 min, MS: 521 (M+H)$^+$ Example 44

The compound described in Example 35 was treated with methylamine as described in procedure F to afford the amide derivative 1-Methylcarbamoyl-1-(1,1'-Biphenyl-4-yl)methyl (1R,3R)-1-Cyclohexyl-1,2,3,4-tetrahydro-beta-carboline-3-carboxamide. LC: $T_r$ 2.12 min, MS: 521 (M+H)$^+$

Example 45

The compound 2-[4-(benzyloxy)phenyl]-1-carboxy-1-ethyl (1S,3R)-1-Cyclohexyl-1,2,3,4-tetrahydro-beta-carboline-3-carboxamide was prepared starting with the compound described in example 47 following procedure E. LC: $T_r$ 2.04 min, MS: 552 (M+H)$^+$

Example 46

The compound 2-[4-(benzyloxy)phenyl]-1-carboxy-1-ethyl (1R,3R)-1-Cyclohexyl-1,2,3,4-tetrahydro-beta-carboline-3-carboxamide was prepared starting with the compound described in example 48 following procedure E. LC: $T_r$ 1.96 min, MS: 552 (M+H)$^+$

Example 47

The compound 2-[4-(benzyloxy)phenyl]-1-methoxycarbonyl-1-ethyl (1S,3R)-1-Cyclohexyl-1,2,3,4-tetrahydro-beta-carboline-3-carboxamide was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with 4-benzyloxy tyrosine methyl ester as described in procedure F to afford the amide derivative and was de-protected according to procedure G to yield 2-[4-(benzyloxy)phenyl]-1-methoxycarbonyl-1-ethyl (1S,3R)-1-Cyclohexyl-1,2,3,4-tetrahydro-beta-carboline-3-carboxamide. LC: $T_r$ 2.18 min, MS: 566 (M+H)$^+$

Example 48

The compound 2-[4-(benzyloxy)phenyl]-1-methoxycarbonyl-1-ethyl (1R,3R)-1-Cyclohexyl-1,2,3,4-tetrahydro-beta-carboline-3-carboxamide was prepared following procedure C, starting from L-trytophan methyl ester and cyclohexane carboxaldehyde. The resulting tetrahydro-β-carboline amino ester was protected according to procedure D and was hydrolyzed following procedure E. Thus obtained acid was treated with 4-benzyloxy tyrosine methyl ester as described in procedure F to afford the amide derivative and was de-protected according to procedure G to yield 2-[4-(benzyloxy)phenyl]-1-methoxycarbonyl-1-ethyl (1R,3R)-1-Cyclohexyl-1,2,3,4-tetrahydro-beta-carboline-3-carboxamide. LC: $T_r$ 2.11 min, MS: 566 (M+H)$^+$

Example 49

The compound described in Example 45 was treated with dimethylamine as described in procedure F to afford the amide derivative 1-Dimethylaminocarbamoyl-1-(1,1'-Biphenyl-4-yl)methyl (1S,3R)-1-Cyclohexyl-1,2,3,4-tetrahydro-beta-carboline-3-carboxamide. LC: $T_r$ 2.23 min, MS: 535 (M+H)$^+$

Example 50

The compound described in Example 46 was treated with dimethylamine as described in procedure F to afford the amide derivative 1-Dimethylaminocarbamoyl-1-(1,1'-Biphenyl-4-yl)methyl (1R,3R)-1-Cyclohexyl-1,2,3,4-tetrahydro-beta-carboline-3-carboxamide. LC: $T_r$ 2.13 min, MS: 535 (M+H)$^+$

Example 51

The compound described in Example 37 was reduced following procedure K to yield the compound 1-Hydroxymethyl-1-(1,1'-Biphenyl-4-yl)methyl (1S,3R)-1-Cyclohexyl-1,2,3,4-tetrahydro-beta-carboline-3-carboxamide. LC: $T_r$ 2.15, MS: 494 (M+H)$^+$

Example 52

The compound 2-(1,1'-Biphenyl-4-yl)1-methoxycarbonyl-1-ethyl (1S,3R)-1-Cyclohexyl-1,2,3,4-tetrahydro-beta-carboline-3-carboxamide was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with 4-4-biphenyl alanine methyl ester as described in procedure F to afford the amide derivative and was de-protected according to procedure G to yield 2-(1,1'-Biphenyl-4-yl)1-methoxycarbonyl-1-ethyl (1S,3R)-1-Cyclohexyl-1,2,3,4-tetrahydro-beta-carboline-3-carboxamide. LC: $T_r$ 2.20 min, MS: 536 (M+H)$^+$

Example 53

The compound 2-(1,1'-Biphenyl-4-yl)1-methoxycarbonyl-1-ethyl (1R,3R)-1-Cyclohexyl-1,2,3,4-tetrahydro-beta-carboline-3-carboxamide was prepared following procedure C, starting from L-trytophan methyl ester and cyclohexane carboxaldehyde. The resulting tetrahydro-β-carboline amino ester was protected according to procedure D and was hydrolyzed following procedure E. Thus obtained acid was treated with 4-4-biphenyl alanine methyl ester as described in procedure F to afford the amide derivative and was de-protected according to procedure G to yield 2-(1,1'-Biphenyl-4-yl)1-methoxycarbonyl-1-ethyl (1R,3R)-1-Cyclohexyl-1,2,3,4-tetrahydro-beta-carboline-3-carboxamide. LC: $T_r$ 2.13 min, MS: 536 (M+H)$^+$

Example 54

The compound 2-(1,1'-Biphenyl-4-yl)1-carboxy-1-ethyl (1S,3R)-1 Cyclohexyl-1,2,3,4-tetrahydro-beta-carboline-3-carboxamide was prepared staring with the compound described in example 52 following procedure E. LC: $T_r$ 2.08 min, MS: 522 (M+H)$^+$

Example 55

The compound 2-(1,1'-Biphenyl-4-yl)1-carboxy-1-ethyl (1R,3R)-1-Cyclohexyl-1,2,3,4-tetrahydro-beta-carboline-3-carboxamide was prepared starting from the compound described in example 53 following procedure E. LC: $T_r$ 2.01 min, MS: 522 (M+H)$^+$

Example 56

The compound described in example 34 was treated with benzylamine as described in procedure F to afford the amide derivative 1-Benzyloxycarbonyl-1-(1,1'-Biphenyl-4-yl)methyl (1R,3R)-1-Cyclohexyl-1,2,3,4-tetrahydro-beta-carboline-3-carboxamide. LC: $T_r$ 2.25 min, MS: 598 (M+H)$^+$

Example 57

The compound 1-Methoxycarbonyl-1-(1,1'-Biphenyl-4-yl)methyl (1R,3R)-1-Cyclohexyl-2-tert-butoxycarbonyl-1,2,3,4-tetrahydro-beta-carboline-3-carboxamide was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F to afford to 1-Methoxycarbonyl-1-(1,1'-Biphenyl-4-yl)methyl (1R,3R)-1-Cyclohexyl-2-tert-butoxycarbonyl-1,2,3,4-tetrahydro-beta-carboline-3-carboxamide. LC: $T_r$ 2.75 min, MS: 622 (M+H)$^+$ Example 58

The compound (3R)-1-(1-benzylindol-3-yl)-2-tert-butoxycarbonyl-1,2,3,4-tetrahydro-beta-carboline-3-carboxylic Acid was prepared following procedure A, starting from L-trytophan methyl ester and N-benzyl indole 3-carboxaldehyde. The resulting tetrahydro-β-carboline amino ester was protected according to procedure D and was hydrolyzed following procedure E to yield (3R)-1-(1-benzylindol-3-yl)-2-tert-butoxycarbonyl-1,2,3,4-tetrahydro-beta-carboline-3-carboxylic Acid. LC: $T_r$ 2.26, MS: 522 (M+H)$^+$ Example 59

The compound (3R)-1-(1-butylindol-3-yl)-2-tert-butoxycarbonyl-1,2,3,4-tetrahydro-beta-carboline-3-carboxylic Acid was prepared following procedure A, starting from L-trytophan methyl ester and N-butyl indole 3-carboxaldehyde. The resulting tetrahydro-β-carboline amino ester was protected according to procedure D and was hydrolyzed following procedure E to yield (3R)-1-(1-butylindol-3-yl)-2-tert-butoxycarbonyl-1,2,3,4-tetrahydro-beta-carboline-3-carboxylic Acid. LC: $T_r$ 2.24, MS: 488 (M+H)$^+$ Example 60

The compound 1-Methoxycarbonyl-1-(1,1'-Biphenyl-4-yl)methyl (3R)-1-(1-butylindol-3-yl)-1,2,3,4-tetrahydro-beta-carboline-3-carboxamide was prepared starting with the compound described in example 59, reacting it with amino biphenyl acetate as described in procedure F to afford to 1-Methoxycarbonyl-1-(1,1'-Biphenyl-4-yl)methyl (3R)-1-(1-butylindol-3-yl)-1,2,3,4-tetrahydro-beta-carboline-3-carboxamide. LC: $T_r$ 2.62, MS: 711 (M+H)$^+$ Example 61

The compound 1-Methoxycarbonyl-1-(1,1'-Biphenyl-4-yl)methyl (3R)-1-(1-butylindol-3-yl)-1,2,3,4-tetrahydro-beta-carboline-3-carboxamide was prepared starting with the compound described in example 60 following procedure G. LC: $T_r$ 2.24, MS: 611 (M+H)$^+$ Example 62

The compound 1-Dimethylcarbamoyl-1-(1,1'-biphenyl-4-yl)methyl (1S,3R)-1-(1,1'-Biphenyl-4-yl)-1,2,3,4-tetrahydro-beta-carboline-3-carboxamide was prepared following procedure B, starting from L-trytophan methyl ester and 4-biphenyl carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative and was de-protected according to procedure G and was hydrolyzed following the procedure E and acid was coupled with dimethyl amine as described in procedure F to yield 1-Dimethylcarbamoyl-1-(1,1'-biphenyl-4-yl)methyl (1S,3R)-1-(1,1'-Biphenyl-4-yl)-1,2,3,4-tetrahydro-beta-carboline-3-carboxamide. LC: $T_r$ 2.27 min, MS: 605 (M+H)$^+$ Example 63

The compound (1S,3R)-1-(Indol-3-yl)-2-tert-butoxycarbonyl-1,2,3,4-tetrahydro-beta-carboline-3-carboxylic Acid was prepared following procedure B, starting from L-tryptophan methyl ester and indole 3-carboxaldehyde. The resulting tetrahydro-β-carboline amino ester was protected according to procedure D and was hydrolyzed following procedure E to yield (1S,3R)-1-(Indol-3-yl)-2-tert-butoxycarbonyl-1,2,3,4-tetrahydro-beta-carboline-3-carboxylic Acid. LC: $T_r$ 2.57 min, MS: 432 (M+H)$^+$ Example 64

The compound 1-(2,4,6-trimethoxybenzylcarbamoyl)-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting with the compound described in example 57 following the procedure E and resulting acid was coupled with 2,4,6-trimethoxy benzyl amine hydrochloride as described in procedure F. LC: $T_r$ 2.78 min, MS: 787 (M+H)$^+$ Example 65

The compound 1-Benzyloxycarbonyl-1-(1,1'-Biphenyl-4-yl)methyl (1S,3R)-1-(1,1'-Biphenyl-4-yl)-2-tert-butoxycarbonyl-1,2,3,4-tetrahydro-beta-carboline-3-carboxamide was prepared following procedure B, starting from L-trytophan methyl ester and 4-biphenyl carboxaldehyde. The resulting tetrahydro-β-carboline amino ester was protected according to procedure D and was hydrolyzed following procedure E. Thus obtained acid was treated with amino biphenyl acetate as described in procedure F to afford the amide derivative was hydrolyzed following the procedure E and acid was coupled with benzyl amine as described in procedure F to yield 1-Benzyloxycarbonyl-1-(1,1'-Biphenyl-4-yl)methyl (1S,3R)-1-(1,1'-Biphenyl-4-yl)-2-tert-butoxycarbonyl-1,2,3,4-tetrahydro-beta-carboline-3-carboxamide. LC: $T_r$ 2.80 min, MS: 768 (M+H)$^+$ Example 66

The compound 1-Propoxycarbonyl-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting with the compound described in example 57 following the procedure E and resulting acid was coupled with 1-propanol as described in procedure F. LC: $T_r$ 2.78 min, MS: 650 (M+H)$^+$ Example 67

The compound 1-Butoxycarbonyl-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting with the compound described in example 57 following the procedure E and resulting acid was coupled with 1-butanol as described in procedure F. LC: $T_r$ 2.79 min, MS: 664 (M+H)$^+$ Example 68

The compound 1-(2-Methoxy-1-ethoxycarbonyl)-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting from the compound described in example 57 following the procedure E and resulting acid was coupled with 2-methoxy ethanol as described in procedure F. LC: $T_r$ 2.73 min, MS: 666 (M+H)$^+$ Example 69

The compound 1-Methoxymethyl-1-(1,1'-Biphenyl-4-yl)methyl (3R)-1-Cyclohexyl-2-tert-butoxycarbonyl-9-methyl- 1,2,3,4-tetrahydro-beta-carboline-3-carboxamide was prepared following procedure A, starting from D-tryptophan methyl ester and cyclohexane carboxaldehyde. The resulting tetrahydro-β-carboline amino ester was protected according to procedure D and was hydrolyzed following procedure E. Thus obtained acid was treated with amino biphenyl acetate as described in procedure F and ester was reduced following procedure K and resulting alcohol was treated with iodomethane according to procedure J to afford 1-Methoxymethyl-1-(1,1'-Biphenyl-4-yl)methyl (3R)-1-Cyclohexyl-2-tert-butoxycarbonyl-9-methyl-1,2,3,4-tetrahydro-beta-carboline-3-carboxamide. MS: 622 (M+H)$^+$

Example 70

The compound 1-Methoxymethyl-1-(1,1'-Biphenyl-4-yl)methyl (3R)-1-Cyclohexyl-9-methyl-1,2,3,4-tetrahydro-beta-carboline-3-carboxamide was prepared starting with the compound described in example 69 following procedure G. LC: T$_r$ 2.61, MS: 522 (M+H)$^+$

Example 71

The compound 1-(2,4,6-trimethoxybenzylcarbamoyl)-1-(1,1'-Biphenyl-4-yl)methyl (1S,3R)-1-Cyclohexyl-1,2,3,4-tetrahydro-beta-carboline-3-carboxamide was prepared following procedure B, starting from L-trytophan methyl ester and N-methyl indole 3-carboxaldehyde. The resulting tetrahydro-β-carboline amino ester was protected according to procedure D and was hydrolyzed following procedure E to yield 1-(2,4,6-trimethoxybenzylcarbamoyl)-1-(1,1'-Biphenyl-4-yl)methyl (1S,3R)-1-Cyclohexyl-1,2,3,4-tetrahydro-beta-carboline-3-carboxamide. LC: T$_r$ 2.69 min, MS: 446 (M+H)$^+$

Example 72

The compound 1-(2,4,6-trimethoxybenzylcarbamoyl)-1-(1,1'-Biphenyl-4-yl)methyl (1S,3R)-1-Cyclohexyl-1,2,3,4-tetrahydro-beta-carboline-3-carboxamide was prepared from example 57 following the procedure E and resulting acid was coupled with 2,4,6-trimethoxy benzyl amine hydrochloride as described in procedure F and amide derivative was de-protected according to procedure G to yield 1-(2,4,6-trimethoxybenzylcarbamoyl)-1-(1,1'-Biphenyl-4-yl)methyl (1S,3R)-1-Cyclohexyl-1,2,3,4-tetrahydro-beta-carboline-3-carboxamide. LC: T$_r$ 2.26 min, MS: 687 (M+H)$^+$

Example 73

The compound 1-(Benzyloxycarbonyl)-1-(1,1'-Biphenyl-4-yl)methyl (1S,3R)-1-(1,1'-Biphenyl-4-yl)-1,2,3,4-tetrahydro-beta-carboline-3-carboxamide was prepared starting with the compound described in example 65 following procedure G. LC: T$_r$ 2.30 min, MS: 668 (M+H)$^+$

Example 74

The compound 1-Propoxycarbonyl-1-(1,1'-Biphenyl-4-yl)methyl (1S,3R)-1-Cyclohexyl-1,2,3,4-tetrahydro-beta-carboline-3-carboxamide was prepared starting with the compound described in example 66 following procedure G. LC: T$_r$ 2.26 min, MS: 550 (M+H)$^+$

Example 75

The compound 1-Butoxycarbonyl-1-(1,1'-Biphenyl-4-yl) methyl (1S,3R)-1-Cyclohexyl-1,2,3,4-tetrahydro-beta-carboline-3-carboxamide was prepared starting with the compound described in example 67 following procedure G. LC: T$_r$ 2.30 min, MS: 564 (M+H)$^+$

Example 76

The compound 1-(2-Methoxy-1-ethoxycarbonyl)-1-(1,1'-Biphenyl-4-yl)methyl (1S,3R)-1-Cyclohexyl-1,2,3,4-tetrahydro-beta-carboline-3-carboxamide was prepared from example 68 following procedure G. LC: T$_r$ 2.17 min, MS: 566 (M+H)$^+$

Example 77

The compound Benzothiazol-2-yl (1S,3R)-1-Cyclohexyl-1,2,3,4-tetrahydro-beta-carboline-3-carboxamide was prepared following procedure B, starting from D-tryptophan methyl ester and cyclohexane carboxaldehyde. The resulting tetrahydro-β-carboline amino ester was protected according to procedure D and was hydrolyzed following procedure E. Thus obtained acid was treated with 2 amino benzothiazole as described in procedure F to afford Benzothiazol-2-yl (1S,3R)-1-Cyclohexyl-1,2,3,4-tetrahydro-beta-carboline-3-carboxamide. LC: T$_r$ 2.68 min, MS: 531 (M+H)$^+$

Example 78

The compound Benzothiazol-2-yl (1S,3R)-1-Cyclohexyl-1,2,3,4-tetrahydro-beta-carboline-3-carboxamide was prepared starting with the compound described in example 77 following procedure G. LC: T$_r$ 2.24 min, MS: 431 (M+H)$^+$

Example 79

The compound 1,1'-Biphenyl-4-oylmethyl (1S,3R)-1-Cyclohexyl-2-tert-butoxycarbonyl-1,2,3,4-tetrahydro-beta-carboline-3-carboxylate was prepared following procedure B, starting from L-trytophan methyl ester and cyclohexane carboxaldehyde. The resulting tetrahydro-β-carboline amino ester was protected according to procedure D and was hydrolyzed following procedure E. Thus obtained acid was treated with 2 bromo 4-phenyl acetophenone as described in procedure L to afford 1,1'-Biphenyl-4-oylmethyl (1S,3R)-1-Cyclohexyl-2-tert-butoxycarbonyl-1,2,3,4-tetrahydro-beta-carboline-3-carboxylate. LC: T$_r$ 2.62, MS: 593 (M+H)$^+$

Example 80

The compound 1,1'-Biphenyl-4-oylmethyl (1R,3R)-1-Cyclohexyl-2-tert-butoxycarbonyl-1,2,3,4-tetrahydro-beta-carboline-3-carboxylate was prepared following procedure C, starting from L-trytophan methyl ester and cyclohexane carboxaldehyde. The resulting tetrahydro-β-carboline amino ester was protected according to procedure D and was hydrolyzed following procedure E. Thus obtained acid was treated with 2 bromo 4-phenyl acetophenone as described in procedure L to afford 1,1'-Biphenyl-4-oylmethyl (1R,3R)-1-Cyclohexyl-2-tert-butoxycarbonyl-1,2,3,4-tetrahydro-beta-carboline-3-carboxylate. LC: T$_r$ 2.61, MS: 593 (M+H)$^+$

Example 81

The compound 2,4,6-Trimethoxybenzyl (1S,3R)-1-(1-methylindol-3-yl)-1,2,3,4-tetrahydro-beta-carboline-3-carboxamide was prepared starting with the compound described in example 71, reacting it with 2,4,6-trimethoxy benzyl amine hydrochloride as described in procedure F to afford 2,4,6-Trimethoxybenzyl (1S,3R)-1-(1-methylindol-3-yl)-1,2,3,4-tetrahydro-beta-carboline-3-carboxamide. LC: T$_r$ 2.88 min, MS: 625 (M+H)$^+$

Example 82

The compound 2,4,6-Trimethoxybenzyl (1S,3R)-1-(1-methylindol-3-yl)-1,2,3,4-tetrahydro-beta-carboline-3- carboxamide was prepared starting with the compound described in example 81 following the procedure G. LC: T$_r$ 2.35 min, MS: 525 (M+H)$^+$ Example 83

The compound 1,1'-Biphenyl-4-oylmethyl (1S)-1-Cyclohexyl-1,2,3,4-tetrahydro-beta-carboline-3-carboxylate was prepared starting with the compound described in example 79 following procedure G. LC: T$_r$ 2.16, MS: 493 (M+H)$^+$ Example 84

The compound 1-(2-Hydroxy-1-propylcarbamoyl-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting with the compound described in example 57 following the procedure E and resulting acid was coupled with 1-amino 2-propanol as described in procedure F. LC: T$_r$ 2.64 min, MS: 665 (M+H)$^+$ Example 85

The compound 1-(2-Oxo-1-propylcarbamoyl-1-(1,1'-Biphenyl-4-yl)methyl (1S,3R)-1-Cyclohexyl-2-tert-butoxycarbonyl-1,2,3,4-tetrahydro-beta-carboline-3-carboxamide was prepared starting with the compound described in example 84 following procedure M. LC: T$_r$ 2.89 min, MS: 663 (M+H)$^+$ Example 86

The following assay methods are utilized to identify compounds of formula 1 which are effective in inhibiting the activity of certain phosphatases, examples of which, as used herein, are PTP1B and TC-PTP.

PTP1B Assay

The assay for PTP1B inhibition is based on the detection of the complex between Malachite Green dye and free phosphate, liberated from the phosphopeptide substrate by PTPase action. To each well of a flat-bottom assay plate is added 45 μL assay buffer [–50 mM Imidazole, pH 7.2, 100 mM NaCl, 5 mM DTT, and 1 mM EDTA] and 10 μL of peptide substrate [Tyrosine Phosphopeptide –1, END($_p$Y) INASL, 80 μM FAC, Promega Cat # V256A] to a total volume of 55 μL. Test compound (10 μL in up to 50% DMSO) is then added. The mixture is incubated for 5 min, at 25° C., and 10 μL of PTP-1B [Protein Tyrosine Phosphatase 1B (PTP-1B); FAC 0.8 nM; Upstate Biotechnology, Cat # 14-109 lot # 19045 ] is then added. The mixture is incubated for 30 min at 25° C. Subsequently, 25 μL of Malachite Green reagent [10% (w/v) Ammonium Molybdate in water, Sigma Cat # A-7302, 0.2% (w/v) Malachite Green in 4 N HCl, Aldrich Cat # 21,302-0] is then added. After incubation for 15 min at 27° C., the reaction endpoint is measured at 640 nM.

The Malachite Green reagent is prepared by mixing one volume of 10% Ammonium Molybdate with 3 volumes of 0.2% Malachite Green solution, stirring at room temperature for 30 min and then filtering and collecting the filtrate. The Malachite Green reagent is treated with 10 μL of 5% Tween 20 per 990 μL of dye solution before use.

T-Cell PTPase Assay

The assay for T-Cell PTPase (TC-PTP) inhibition is based on the detection of the complex between Malachite Green dye and free phosphate, liberated from the phosphopeptide substrate by PTPase action. To each well of a flat-bottom assay plate is added 45 μL assay buffer [–50 mM Imidazole, pH 7.2, 100 mM NaCl, 5 mM DTT, and 1 mM EDTA] and 10 μL of peptide [Tyrosine Phosphopeptide –1, END ($_p$Y) INASL at k$_m$=80 μM FAC; Promega Cat # V256A] to a total volume of 55 μL. The test compound (10 μL in up to 50% DMSO) is then added. The mixture is incubated for 5 min at 25° C., and 10 μL of 1 nM T-cell PTPase (CalBiochem) is then added. The mixture is incubated for an additional 30 min at 25° C. Subsequently, 25 μL of Malachite Green reagent [10% (w/v) Ammonium Molybdate in water; Sigma Cat # A-7302; 0.2% (w/v) Malachite Green in 4 N HCl; Aldrich Cat # 21,302-0] is then added. After incubation for 15 min at 27° C., the reaction endpoint is read at 640 nM.

The Malachite Green reagent is prepared by mixing one volume of 10% Ammonium Molybdate with 3 volumes of 0.2% Malachite Green solution, stirring at room temperature for 30 min and then filtering. The Malachite Green reagent is treated with 10 μL of 5% Tween 20 per 990 μL of dye solution before use.

Test compounds are typically examined at six concentrations in the above assay. For this assay, the IC$_{50}$ (microM) of the enzyme inhibition assay represents the concentration of compound at which 50% signal has been inhibited.

The compounds of the present invention are found to inhibit protein tyrosine phosphatase activity with inhibitory potencies of about 0.01 microM to about 30 microM. In a preferred range, the compounds inhibited protein tyrosine phosphatase activity with inhibitory potencies in a range of about 1 microM to about 10 microM. In a more preferred range, the compounds inhibited protein tyrosine phosphatase activity with inhibitory potencies of about 0.01 microM to about 3 microM.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for PTPase-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

What is claimed is:

1. A compound of Formula (I):

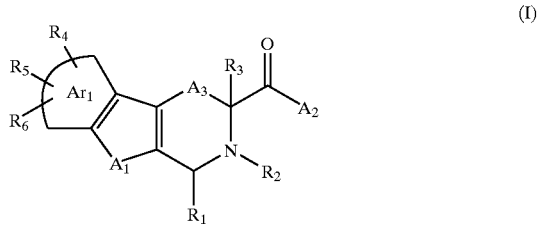

wherein

R$_1$ is
  1,1'-biphenyl-4-yl; cyclohexyl; 4-bromo, chloro, or fluorophenyl; 2,4-dichlorophenyl; 4-benzyloxyphenyl; 4-(4-carboxy)benzyloxyphenyl; cyclopentyl; (E)-2-phenylvinylphenyl; indol-3-yl; 4-hydroxyphenyl; 4-hydroxybenxyl; 1-benxylindol-3-yl; or 1-butylindol-3-yl;

R$_2$ is
  (a) hydrogen;
  (b) alkyl; alkenyl; alkynyl;
  (c) heterocyclyl; cycloalkyl;
  (d) -alkylene-aryl; -alkenylene-aryl; -alkynylene-aryl; -alkyloxy-aryl,
  (e) -alkylene-heteroaryl; -alkenylene-heteroaryl; -alkynylene-heteroaryl; -alkoxy-heteroaryl;
  (f) -alkylene-heterocyclyl; -alkenylene-heterocyclyl; -alkynylene-heterocyclyl or
  (g) —C(O)—OR$_7$; -alkylene-C(O)—OR$_7$; -alkenylene-C(O)—OR$_7$; -alkynylene-C(O)—OR$_7$, —C(O)—NR$_7$R$_8$; -alkylene-C(O)—NR$_7$R$_8$; -alkenylene-C(O)—NR$_7$R$_8$; -alkynylene-C(O)—NR$_7$R$_8$, -alkylene-O-aryl; -alkylene-O-alkylene-aryl; -alkylene-O-cycloalkyl; —(SO$_2$)—R$_7$; -alkylene-S(O$_2$)—R$_7$; -alkenylene-S(O$_2$)—R$_7$; -alkynylene-S(O$_2$)—R$_7$; -alkylene-S(O)—R$_7$; -alkenylene-S(O)—R$_7$; -alkynylene-S(O)—R$_7$; -alkylene-S(O$_2$)—R$_7$; -alkenylene-S(O$_2$)—R$_7$; -alkynylene-S(O$_2$)—R$_7$; —S(O$_2$)NR$_7$R$_8$; -alkylene-S(O$_2$)—NR$_7$R$_8$; -alkenylene-S(O$_2$)—NR$_7$R$_8$; or -alkynylene-S(O$_2$)—NR$_7$R$_8$; wherein
    R$_7$ and R$_8$ independently comprise hydrogen, aryl, alkyl, or -alkylene-aryl; or R$_7$ and R$_8$ may be taken together to form a ring having the formula —(CH$_2$)$_m$—T—(CH$_2$)$_n$— bonded to the nitrogen atom to which R$_7$ and R$_8$ are attached, wherein
      m and n are, independently, 1, 2, 3, or 4; T comprises —CH$_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N(R$_9$)—, —N(C(O)R$_9$)—, —N(C(O)NHR$_9$)—, —N(S(O$_2$)NHR$_9$)—, —N(SO$_2$R$_9$)—, or —N(C(O)OR$_9$)—; or
    R$_7$ and R$_8$ may be taken together, with the nitrogen atom to which they are attached, to form a heterocyclyl or heteroaryl ring;
R$_3$ is
  (a) hydrogen;
  (b) alkyl; alkenyl; alkynyl;
  (c) -alkylene-aryl; -alkenylene-aryl; -alkynylene-aryl;
  (d) -alkylene-heteroaryl; -alkenylene-heteroaryl or -alkynylene-heteroaryl;
A$_2$ is —NR$_{10}$R$_{11}$, or —NR$_{10}$A$_4$;
  wherein
    R$_{10}$ and R$_{11}$ are independently selected from the group consisting of:
    (a) hydrogen;
    (b) alkyl; alkenyl; alkynyl;
    (c) heterocyclyl; cycloalkyl;
    (d) aryl; heteroaryl; -arylene-aryl; -arylene-heteroaryl; -heteroarylene-aryl; -heteroarylene-heteroaryl; -alkylene-aryl; -alkenylene-aryl; -alkynylene-aryl; -alkyloxy-aryl; -alkylene-heteroaryl, -alkenylene-heteroaryl, -alkynylene-heteroaryl, -alkoxy-heteroaryl,
    (e) -alkylene-heterocyclyl; -alkenylene-heterocyclyl; -alkynylene-heterocyclyl;
    (f) -arylene-L$_2$-alkylene-aryl, -arylene-L$_2$-alkylene-heteroaryl, -arylene-alkylene-L$_2$-heteroaryl, -arylene-alkylene-L$_2$-aryl, -alkylene-arylene-L$_2$-alkylene-aryl, -alkylene-L$_2$-aryl, -alkylene-L$_2$-arylene-aryl, -alkylene-arylene-L$_2$-alkylene-C(O)O-alkyl, -alkylene-arylene-L$_2$-alkylene-C(O)OH, -alkylene-arylene-L$_2$-alkylene-C(O)NH-alkyl, -alkylene-arylene-L$_2$-alkylene-heteroaryl, -alkylene-arylene-alkylene-L$_2$-aryl, -alkylene-arylene-alkylene-L$_2$-heteroaryl;
    wherein L$_2$ comprises O, —C(O)—, S, —S(O)—, —S(O$_2$)—, a direct bond;
    (g) —C(O)—OR$_{12}$, -alkylene-C(O)—OR$_{12}$, -alkenylene-C(O)—OR$_{12}$, -alkynylene-C(O)—OR$_{12}$, —C(O)—NR$_{12}$R$_{13}$, -alkylene-C(O)—NR$_{12}$R$_{13}$, -alkenylene-C(O)—NR$_{12}$R$_{13}$, alkynylene-C(O)—NR$_{12}$R$_{13}$, -alkylene-O-aryl, -alkylene-O-alkylene-aryl, -alkylene-O-cycloalkyl, —S(O$_2$)—R$_{12}$, -alkylene-S(O$_2$)—R$_{12}$, -alkenylene-S(O$_2$)—R$_{12}$, -alkynylene-S(O$_2$)—R$_{12}$, -alkylene-S(O)—R$_{12}$, -alkenylene-S(O)—R$_{12}$, -alkynylene-S(O)—R$_{12}$, -alkylene-S(O)—R$_{12}$, -alkenylene-S(O)—R$_{12}$, -alkynylene-S(O)—R$_{12}$, —S(O$_2$)—NR$_{12}$R$_{13}$, -alkylene-S(O$_2$)—NR$_{12}$R$_{13}$, -alkenylene-S(O$_2$)—NR$_{12}$R$_{13}$, and -alkynylene-S(O$_2$)—NR$_{12}$R$_{13}$;
  wherein R$_{10}$ and R$_{11}$ may be taken together with the nitrogen atom to which they are attached, to form a heterocycyl or heteroaryl ring;
  wherein
    R$_{12}$ and R$_{13}$ are independently selected from the group consisting of hydrogen, aryl, alkyl, and alkylene-aryl; or
    R$_{12}$ and R$_{13}$ may be taken together to form a ring having the formula —(CH$_2$)$_s$—V—(CH$_2$)$_t$— bonded to the nitrogen atom to which R$_{12}$ and R$_{13}$ are attached, wherein
      s and t are, independently, 1, 2, 3, or 4; V is —CH$_2$—, —C(O)—, —O—, —N(H)—, —S—, —S(O)—, —S(O$_2$)—, —CON(H)—, —NHC(O)—, —NHC(O)N(H)—, —NHS(O$_2$), —S(O$_2$)N(H)—, —(O)CO—, —NHS(O$_2$)NH—, —OC(O)—, —N(R$_{14}$)—, —N(C(O)R$_{14}$)—, —N(C(O)NHR$_{14}$)—, —N(SO$_2$NHR$_{14}$)—, —N(S(O$_2$)R$_{14}$)—, or —N(C(O)OR$_{14}$)—; or
    R$_{12}$ and R$_{13}$ may be taken together, with the nitrogen atom to which they are attached, to form a heterocyclyl or heteroaryl ring;
A$_4$ is

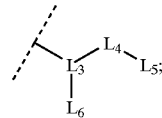

wherein
  L$_3$ is alkyline, alkenyline, heteroaryline, aryline, cycloalkyline, or heterocyclyline group;
  L$_4$ is a direct bond, —C(O)—N(R$_{15}$)—, —C(O)—O—, —C(O)—, or —N(R$_{15}$)—CO—N(R$_{16}$)—, -alkylene-C(O)—N(R$_{15}$)—, -alkylene-C(O)—O—, -alkylene-C(O)—, or -alkylene-N(R$_{15}$)—CO—N(R$_{16}$)—;
  L$_5$ is H, alkyl, alkenyl, alkynyl, heterocyclyl, heteroaryl, or -alkylene-aryl;
  L$_6$ is hydrogen, alkyl, alkenyl, alkynyl, -alkylene-aryl, -alkylene-heteroaryl, -alkylene-O-alkylene-aryl, -alkylene-arylene-O-alkylene-aryl, -alkylene-S-alkylene-aryl, -alkylene-O-alkyl, -alkylene-S-alkyl, -alkylene-NH$_2$, -alkylene-OH, -alkylene-SH, alkylene-cycloalkyl, alkylene-heterocyclyl, cycloalkyl, heterocyclyl, alkylene-arylene-aryl, arylene-aryl, -alkylene-C(O)—OR$_{17}$, -alkylene-C(O)—NR$_{17}$R$_{18}$, -alkylene-NR$_{17}$R$_{18}$, -alkylene-N(R$_{17}$)—C(O)—R$_{18}$, or -alkylene-N(R$_{17}$)—S(O$_2$)—R$_{18}$;

wherein
- $R_{17}$ and $R_{18}$ are independently selected from the group consisting of hydrogen, aryl, alkyl, and alkylene-aryl; or
- $R_{17}$ and $R_{18}$ may be taken together to form a ring having the formula $-(CH_2)_o-P-(CH_2)_w-$ bonded to the nitrogen atom to which $R_{17}$ and $R_{18}$ are attached, wherein
  - o and w are, independently, 1, 2, 3, or 4; P is $-CH_2-$, $-C(O)-$, $-O-$, $-N(H)-$, $-S-$, $-S(O)-$, $-S(O_2)-$, $-CON(H)-$, $-NHC(O)-$, $-NHC(O)N(H)-$, $-NHS(O_2)$, $-S(O_2)N(H)-$, $-(O)CO-$, $-NHS(O_2)NH-$, $-OC(O)-$, $-N(R_{19})-$, $-N(C(O)R_{19})-$, $-N(C(O)NHR_{19})-$, $-N(SO_2NHR_{19})-$, $-N(S(O_2)R_{19})-$, or $-N(C(O)OR_{19})-$; or
- $R_{17}$ and $R_{18}$ may be taken together with the nitrogen atom to which they are attached to form a heterocyclyl or heteroaryl ring;

$R_9$, $R_{14}$, $R_{15}$, $R_{16}$, and $R_{19}$ are independently selected from the group consisting of hydrogen, aryl, alkyl, and alkylene-aryl;

$A_1$ is O; S; or $NR_{20}$, where $R_{20}$ is:
(a) hydrogen;
(b) alkyl;
(c) alkenyl; alkynyl; heterocyclyl; cycloalkyl; -alkylene-aryl; -alkenylene-aryl; -alkynylene-aryl; -alkyloxy-aryl; -alkylene-heteroaryl; -alkenylene-heteroaryl; -alkynylene-heteroaryl; -alkoxy-heteroaryl; -alkylene-heterocyclyl; -alkenylene-heterocyclyl; -alkynylene-heterocyclyl;
(d) -alkylene-C(O)—$OR_{21}$; -alkenylene-C(O)—$OR_{21}$; -alkynylene-C(O)—$OR_{21}$; —C(O)—$NR_{21}R_{22}$; -alkylene-C(O)—$NR_{21}R_{22}$; -alkenylene-C(O)—$NR_{21}R_{22}$; -alkynylene-C(O)—$NR_{21}R_{22}$; —alkynylene-C(O)—$NR_{21}R_{22}$; -alkylene-O-aryl; -alkylene-O-alkylene-aryl; -alkylene-O-cycloalkyl; —$S(O_2)$—$R_{21}$; -alkylene-$S(O_2)$—$R_{21}$; -alkenylene-$S(O_2)$—$R_{21}$; -alkynylene-$S(O_2)$—$R_{21}$; -alkylene-S(O)—$R_{21}$; -alkenylene-S(O)—$R_{21}$; -alkynylene-S(O)—$R_{21}$; alkylene-S(O)—$R_{21}$; -alkenylene-S(O)—$R_{21}$; -alkynylene-S(O)—$R_{21}$; —$S(O_2)$—$NR_{21}R_{22}$; -alkylene-$S(O_2)$—$NR_{21}R_{22}$; -alkenylene-$S(O_2)$—$NR_{21}R_{22}$; or -alkynylene-$S(O_2)$—$NR_{21}R_{22}$; wherein
  - $R_{21}$ and $R_{22}$ are independently selected from the group consisting of hydrogen, aryl, alkyl, and alkylene-aryl; or
  - $R_{21}$ and $R_{22}$ may be taken together to form a ring having the formula $-(CH_2)_x-Z-(CH_2)_y-$ bonded to the nitrogen atom to which $R_{14}$ and $R_{15}$ are attached; wherein
    - x and y are, independently, 1, 2, 3, or 4; Z is $-CH_2-$, $-C(O)-$, $-O-$, $-N(H)-$, $-S-$, $-S(O)-$, $-S(O_2)-$, $-C(O)N(H)-$, $-NHC(O)-$, $-NHC(O)N(H)-$, $-NHS(O_2)-$, $-S(O_2)N(H)-$, $-(O)CO-$, $-NHS(O_2)H-$, $-OC(O)-$, $-N(R_{23})-$, $-N(C(O)R_{23})-$, $-N(C(O)NHR_{23})-$, $-N(S(O_2)NHR_{23})-$, $-N(S(O_2)R_{23})-$, or $-N(C(O)OR_{23})-$; or
  - $R_{21}$ and $R_{22}$ may be taken together, with the nitrogen atom to which they are attached, to form a heterocyclyl or heteroaryl ring;

$A_3$ is $-CH_2-$;

$Ar_1$ is, taken together with the double bond in Formula (I), aryl;

$R_4$, $R_5$, and $R_6$ are independently selected from the group consisting of
(a) hydrogen;
(b) aryl, heteroaryl;
(c) heterocyclyl; cycloalkyl;
(d) -alkylene-Y-aryl; -alkenylene-Y-aryl; -alkynlene-Y-aryl; alkylene-Y-heteroaryl, -alkenylene-Y-heteroaryl; -alkynlene-Y-heteroaryl; -alkylene-Y-cycloalkyl; -alkenylene-Y-cycloalkyl; -alkynlene-Y-cycloalkyl; -alkylene-Y-heterocyclyl; -alkenylene-Y-heterocyclyl; alkynlene-Y-heterocyclyl; —Y—H; —Y-alkyl; —Y-aryl; —Y-alkylene-aryl; —Y-alkylene-$NR_{24}R_{25}$; —Y—O—Si-(alkyl)$_3$; and —Y—O—Si-(alkylene-aryl)$_3$;

wherein
Y is $-CH_2-$, $-O-$, $-N(H)-$, $-S-$, $-S(O)-$, $S(O_2)-$, $-C(O)N(H)-$, $-NHC(O)-$, $-NHC(O)N(H)-$, $-NHS(O_2)$, $-S(O_2)N(H)-$, $-C(O)-$O$-$, $-C(NH)-$O$-$, $-NHS(O_2)H-$, or $-O-C(O)-$;

$R_{24}$ and $R_{25}$ are independently selected from the group consisting of hydrogen, aryl, alkyl, and alkylene-alyl; or $R_{24}$ and $R_{25}$ may be taken together to form a ring having the formula $-(CH_2)_q-Q-(CH_2)_r-$ bonded to the nitrogen atom to which $R_{24}$ and $R_{25}$ are attached, wherein
  q and r are, independently, 1, 2, 3, or 4; Q is $-CH_2-$, $-O-$, $-N(H)-$, $-S-$, $-S(O)-$, $-S(O_2)$, $-CON(H)-$, $-NHC(O)-$, $-NHC(O)N(H)-$, $-NHS(O_2)-$, $-S(O_2)N(H)-$, $-(O)CO-$, $-NHS(O_2)H-$, $-OC(O)-$, $-N(R_{26})-$, $-N(C(O)R_{26})-$, $-N(C(O)NHR_{26})-$, $-N(S(O_2)NHR_{26})-$, $-N(S(O_2)R_{26})-$ or $-N(C(O)OR_{26})-$; or $R_{24}$ and $R_{25}$ may be taken together, with the nitrogen atom to which they are attached, to form a heterocyclyl or heteroalyl ring;

$R_{23}$ and $R_{26}$ are independently selected from the group consisting of hydrogen, aryl, alkyl, and alkylene-aryl; or a pharmaceutically acceptable salt, or solvate thereof.

2. The compound of Formula (I) of claim 1, wherein $R_4$, $R_5$, and $R_6$ are independently selected from the group consisting of hydrogen, alkyl, carboxy, and alkylcarbamoyl.

3. The compound of Formula (I) of claim 1, wherein $A_1$ is $NR_{20}$, wherein $R_{20}$ is hydrogen, or alkyl.

4. The compound of Formula (I) of claim 1, wherein $R_2$ is a hydrogen or an alkyloxycarbonyl group.

5. The compound of Formula (I) of claim 1, wherein $A_2$ is $-NR_{10}R_{11}$, or $-NR_{10}A_4$, wherein $R_{10}$ and $R_{11}$ are independently selected from the group consisting of hydrogen, alkyl, heterocyclyl, cycloalkyl, benzyl, 3-Fluorophenyl, 2-(3-Fluorophenyl)-1-ethyl, 2,4,6-Trimethoxybenzyl, 4-tert-Butylbenzyl, 4-Chlorobenzyl, 4-Carboxybenzyl, 2(4-(methoxycarbonylmethoxy)-phenyl-1-ethyl, (R)-1-Methoxycarbonyl-1-(4-hydroxyphenyl)methyl, or 1-Hydroxymethyl-1-(1,1'-Biphenyl-4-yl)methyl and $A_4$ comprises 1,1'-Biphenyl-4-yl; 1-Benzylcarbamoyl-1-(1,1'-Biphenyl-4-yl)methyl; (5-methyl-2-furan)methyl; 4-(methoxycarbonylmethyl)-1-phenyl; 4-(Carboxymethyl)-1-phenyl; 4-Methoxycarbonyl-1-cyclohexyl; 1-Methoxycarbonyl-1-(1,1'-Biphenyl-4-yl)methyl; 1-(1,1'-Biphenyl-4-yl)1-carboxymethyl; (R)-1-Methoxycarbonyl-1-(4-hydroxybenzyl)methyl; 1-Methylcarbamoyl-1-(1,1'-Biphenyl-4-yl)methyl; 2-[4-(benzyloxy)phenyl]-1-carboxy-1-ethyl; 1-Dimethylaminocarbamoyl-1-(1,1'-Biphenyl-4-yl)

methyl; 2-(1,1'-Biphenyl-4-yl)1-methoxycarbonyl-1-ethyl; 1-Benzyloxycarbonyl-1-(1,1'-Biphenyl-4-yl)methyl; 1-Propoxycarbonyl-1-(1,1'-Biphenyl-4-yl)methyl; 1-Butoxycarbonyl-1-(1,1'-Biphenyl-4-yl)methyl; 1-(2-Methoxy-1-ethoxycarbonyl)-1-(1,1'-Biphenyl-4-yl)methyl; 1-Methoxymethyl-1-(1,1'-Biphenyl-4-yl)methyl; Benzothiazol-2-yl; 1-(2-Hydroxy-1-propylcarbamoyl-1-(1,1'-Biphenyl-4-yl)methyl; and 1-(2-Oxo-1-propylcarbamoyl-1-(1,1'-Biphenyl-4-yl)methyl.

6. The compound of Formula (I) of claim 1, wherein $R_4$, $R_5$, and $R_6$ are independently selected from the group consisting of hydrogen, alkyl, carboxy, and alkylcarbamoyl; $A_1$ is $NR_{20}$, wherein $R_{20}$ is hydrogen, or alkyl; $R_2$ is a hydrogen or an alkyloxycarbonyl group; and $A_2$ is $NR_{10}R_{11}$, or $-NR_{10}A_4$, wherein $R_{10}$ and $R_{11}$ are independently selected from the group consisting of hydrogen; alkyl; heterocyclyl, cycloalkyl, benzyl, 3-Fluorophenyl, 2-(3-Fluorophenyl)-1-ethyl, 2,4,6-Trimethoxybenzyl, 4-tert-Butylbenzyl, 4-Chlorobenzyl, 4-Carboxybenzyl, 2(4-(methoxycarbonylmethoxy)-phen-yl-1-ethyl, (R)-1-Methoxycarbonyl-1-(4-hydroxyphenyl)methyl, or 1-Hydroxymethyl-1-(1,1'-Biphenyl-4-yl)methyl and $A_4$ comprises 1,1'-Biphenyl-4-yl; 1-Benzylcarbamoyl-1-(1,1'-Biphenyl-4-yl)methyl; (5-methyl-2-furan)methyl; 4-(methoxycarbonylmethyl)-1-phenyl; 4-(Carboxymethyl)-1-phenyl; 4-Methoxycarbonyl-1-cyclohexyl; 1-Methoxycarbonyl-1-(1,1'-Biphenyl-4-yl)methyl; 1-(1,1'-Biphenyl-4-yl)1-carboxymethyl; (R)-1-Methoxycarbonyl-1-(4-hydroxybenzyl)methyl; 1-Methylcarbamoyl-1-(1,1'-Biphenyl-4-yl)methyl; 2-[4-(benzyloxy)phenyl]-1-carboxy-1-ethyl; 1-Dimethylaminocarbamoyl-1-(1,1'-Biphenyl-4-yl) methyl; 2-(1,1'-Biphenyl-4-yl)1-methoxycarbonyl-1-ethyl; 1-Benzyloxycarbonyl-1-(1,1'-Biphenyl-4-yl)methyl; 1-Propoxycarbonyl-1-(1,1'-Biphenyl-4-yl)methyl; 1-Butoxycarbonyl-1-(1,1'-Biphenyl-4-yl)methyl; 1-(2-Methoxy-1-ethoxycarbonyl)-1-(1,1'-Biphenyl-4-yl)methyl; 1-Methoxymethyl-1-(1,1'-Biphenyl-4-yl)methyl; Benzothiazol-2-yl; 1-(2-Hydroxy-1-propylcarbamoyl-1-(1,1'-Biphenyl-4-yl)methyl; and 1-(2-Oxo-1-propylcarbamoyl-1-(1,1'-Biphenyl-4-yl)methyl.

7. The compound of Formula (I) of claim 1, wherein the compound is:

Benzyl 1-(1,1'-biphenyl-4-yl)-1,2,3,4-tetrahydro-beta-carboline-3-carboxamide, 3-Fluorophenyl 1-(1,1'-biphenyl-4-yl)-2-tert-butoxycarbonyl-1,2,3,4-tetrahydro-beta-carboline-3-carboxamide, 2-(3- Fluorophenyl)-1-ethyl 1-(1,1'-Biphenyl-4-yl)-1,2,3,4-tetrahydro-beta-carboline-3-carboxamide, 1,1'-Biphenyl-4-yl (1S,3S)-1-(1,1'-Biphenyl-4-yl)-1,2,3,4-tetrahydro-beta-carboline-3-carboxamide, 1-Benzylcarbamoyl-1-(1,1'-Biphenyl-4-yl) methyl (1S,3S)-1-(1,1'-Biphenyl-4-yl)-1,2,3,4-tetrahydro-beta-carboline-3-carboxamide, 2,4,6-Trimethoxybenzyl (1S,3R)-1-Cyclohexyl-1,2,3,4-tetrahydro-beta-carboline-3-carboxamide, 4-tert-Butylbenzyl (1S,3R)-1-(1,1'-Biphenyl-4-yl)-1,2,3,4-tetrahydro-beta-carboline-3-carboxamide, 2,4,6-Trimethoxybenzyl (1S,3R)-1-(4-bromophenyl)-1,2,3,4-tetrahydro-beta-carboline-3-carboxamide, (5-methyl-2-furan)methyl (1S,3R)-1-(1,1'-Biphenyl-4-yl)-1,2,3,4-tetrahydro-beta-carboline-3-carboxamide, 4-Chlorobenzyl (1S,3R)-1-(2,4-dichlorophenyl)-1,2,3,4-tetrahydro-beta-carboline-3-carboxamide, 2,4,6-Trimethoxybenzyl (1S,3R)-1-(4-benzyloxyphenyl)-1,2,3,4-tetrahydro-beta-carboline-3-carboxamide, 4-Carboxybenzyl (1S,3R)-1-(1,1'-Biphenyl-4-yl)-1,2,3,4-tetrahydro-beta-carboline-3-carboxamide, 2,4,6-Trimethoxybenzyl (1S,3R)-1-(4-(4-carboxy) benzyloxyphenyl)-2-tert-butoxycarbonyl-1,2,3,4-tetrahydro-beta-carboline-3-carboxamide, 4-(methoxycarbonylmethyl)-1-phenyl (1S,3R)-1-(1,1'-Biphenyl-4-yl)-2-tert-butoxycarbonyl-1,2,3,4-tetrahydro-beta-carboline-3-carboxamide, 2,4,6-Trimethoxybenzyl 1-(1,1'-Biphenyl-4-yl)-6-methylcarboximidatoyl-1,2,3,4-tetrahydro-beta-carboline-3-carboxamide, 2,4,6-Trimethoxybenzyl 1-(1,1'-Biphenyl-4-yl)-6-methoxycarbonyl-1,2,3,4-tetrahydro-beta-carboline-3-carboxamide, 4-(Carboxymethyl)-1-phenyl (1S,3R)-1-(1,1'-Biphenyl-4-yl)-2-tert-butoxycarbonyl-1,2,3,4-tetrahydro-beta-carboline-3-carboxamide, 4-(Carboxymethyl)-1-phenyl (1S,3R)-1-(1,1'-Biphenyl-4-yl)-1,2,3,4-tetrahydro-beta-carboline-3-carboxamide, 4-Methoxycarbonyl-1-cyclohexyl (1S,3R)-1-(1,1'-Biphenyl-4-yl)-2-tert-butoxycarbonyl-1,2,3,4-tetrahydro-beta-carboline-3-carboxamide, 2(4-(methoxycarbonylmethoxy)-phenyl-1-ethyl (1S,3R)-1-(1,1'-Biphenyl-4-yl)-2-tert-butoxycarbonyl-1,2,3,4-tetrahydro-beta-carboline-3-carboxamide, (5-Methyl-2-furan)methyl (1R, 3S)-1-(1,1'-Biphenyl-4-yl)-1,2,3,4-tetrahydro-beta-carboline-3-carboxamide, 2,4,6-Trimethoxybenzyl 1-Cyclopentyl-1,2,3,4-tetrahydro-beta-carboline-3-carboxamide, 2,4,6-Trimethoxybenzyl 1-(1,1'-Biphenyl-4-yl)-6-carboxy-1,2,3,4-tetrahydro-beta-carboline-3-carboxamide, 1-Methoxycarbonyl-1-(1,1'-Biphenyl-4-yl)methyl (3R)-1-(1,1'-Biphenyl-4-yl)-1,2,3,4-tetrahydro-beta-carboline-3-carboxamide, 2,4,6-Trimethoxybenzyl (1R,3R)-1-{4-[(E)-2-phenylvinyl]phenyl}-1,2,3,4-tetrahydro-beta-carboline-3-carboxamide, 2,4,6-Trimethoxybenzyl 1-(1,1'-Biphenyl-4-yl)-6-butylcarbamoyl-1,2,3,4-tetrahydro-beta-carboline-3-carboxamide, 2,4,6-Trimethoxybenzyl (1S,3R)-1-(Indol-3-yl)-2-tert-butoxycarbonyl-1,2,3,4-tetrahydro-beta-carboline-3-carboxamide, 2,4,6-Trimethoxybenzyl (1R,3R)-1-(Indol-3-yl)-2-tert-butoxycarbonyl-1,2,3,4-tetrahydro-beta-carboline-3-carboxamide, 2,4,6-Trimethoxybenzyl (1S,3R)-1-(Indol-3-yl)-1,2,3,4-tetrahydro-beta-carboline-3-carboxamide, 2,4,6-Trimethoxybenzyl (1R,3R)-1-(Indol-3-yl)-1,2,3,4-tetrahydro-beta-carboline-3-carboxamide, (R)-1-Methoxycarbonyl-1-(4-hydroxyphenyl)methyl (1S)-1-(1,1'-Biphenyl-4-yl)-1,2,3,4-tetrahydro-beta-carboline-3-carboxamide, (R)-1-Methoxycarbonyl-1-(4-hydroxyphenyl)methyl (1R)-1-(1,1'-Biphenyl-4-yl)-2-tert-butoxycarbonyl-1,2,3,4-tetrahydro-beta-carboline-3-carboxamide, 1-(1,1'-Biphenyl-4-yl)1-carboxymethyl (1S,3R)-1 Cyclohexyl-1,2,3,4-tetrahydro-beta-carboline-3-carboxamide, 1-(1,1'-Biphenyl-4-yl)1-carboxymethyl (1R,3R)-1 Cyclohexyl-1,2,3,4-tetrahydro-beta-carboline-3-carboxamide, (R)-1-Methoxycarbonyl-1-(4-hydroxybenzyl)methyl (1S)-1-(1,1'-Biphenyl-4-yl)-1,2,3,4-tetrahydro-beta-carboline-3-carboxamide, 1-Methoxycarbonyl-1-(1,1'-Biphenyl-4-yl)methyl (1S,3R)-1-Cyclohexyl-1,2,3,4-tetrahydro-beta-carboline-3-carboxamide, 1-Methoxycarbonyl-1-(1,1'-Biphenyl-4-yl)methyl (1R,3R)-1-Cyclohexyl-1,2,3,4-tetrahydro-beta-carboline-3-carboxamide, 1-Carboxy-1-(1,1'-Biphenyl-4-yl)methyl (1S,3R)-1-(4-Bromophenyl)-1,2,3,4-tetrahydro-beta-carboline-3-carboxamide, 1-Carboxy-1-(1,1'-Biphenyl-4-yl)methyl (1R,3R)-1-(4-Bromophenyl)-1,2,3,4-tetrahydro-beta-carboline-3-carboxamide, 1-Methoxycarbonyl-1-(1,1'-Biphenyl-4-yl)methyl (1S,3R)-1-(4-Bromophenyl)-1,2,3,4-tetrahydro-beta-carboline-3-carboxamide, 1-Methoxycarbonyl-1-(1,1'-Biphenyl-4-yl)methyl (1R,3R)-1-(4-Bromophenyl)-1,2,3,4-tetrahydro-beta-carboline-3-carboxamide, 1-Methylcarbamoyl-1-(1,1'-Biphenyl-4-yl)methyl (1S, 3R)-1-Cyclohexyl-1,2,3,4-tetrahydro-beta-carboline-3-carboxamide, 1-Methylcarbamoyl-1-(1,1'-Biphenyl-4-yl)methyl (1R,3R)-1-Cyclohexyl-1,2,3,4-tetrahydro-beta-carboline-3-carboxamide, 2-[4-(benzyloxy)phenyl]-1-carboxy-1-ethyl (1S,3R)-1-Cyclohexyl-1,2,3,4-tetrahydro-beta-carboline-3-carboxamide, 2-[4-(benzyloxy)phenyl]-1-carboxy-1-ethyl (1R,3R)-1-Cyclohexyl-1,2,3,4-tetrahydro-beta-carboline-3-carboxamide, 2-[4-(benzyloxy)phenyl]-1-methoxycarbonyl-1-ethyl (1S,3R)-1-Cyclohexyl-1,2,3,4-tetrahydro-beta-carboline-3-carboxamide, 2-[4-(benzyloxy)phenyl]-1-methoxycarbonyl-1-ethyl (1R,3R)-1-Cyclohexyl-1,2,3,4-tetrahydro-beta-carboline-3-carboxamide, 1-Dimethylaminocarbamoyl-1-(1,1'-Biphenyl-4-yl)methyl (1S,3R)-1-Cyclohexyl-1,2,3,4-tetrahydro-beta-carboline-3-carboxamide, 1-Dimethylaminocarbamoyl-1-(1,1'-Biphenyl-4-yl)methyl (1R,3R)-1-Cyclohexyl-1,2,3,4-tetrahydro-beta-carboline-3-carboxamide, 1-Hydroxymethyl-1-(1,1'-Biphenyl-4-yl)methyl (1S,3R)-1-Cyclohexyl-1,2,3,4-tetrahydro-beta-carboline-3-carboxamide, 2-(1,1'-Biphenyl-4-yl)1-methoxycarbonyl-1-ethyl (1S,3R)-1-Cyclohexyl-1,2,3,4-tetrahydro-beta-carboline-3-carboxamide, 2-(1,1'-Biphenyl-4-yl)1-methoxycarbonyl-1-ethyl (1R,3R)-1-Cyclohexyl-1,2,3,4-tetrahydro-beta-carboline-3-carboxamide, 2-(1,1'-Biphenyl-4-yl) 1-carboxy-1-ethyl (1S,3R)-1 Cyclohexyl-1,2,3,4-tetrahydro-beta-carboline-3-carboxamide, 2-(1,1'-Biphenyl-4-yl)1-carboxy-1-ethyl (1R,3R)-1-Cyclohexyl-1,2,3,4-tetrahydro-beta-carboline-3-carboxamide, 1-Benzyloxycarbonyl-1-(1,1'-Biphenyl-4-yl)methyl (1R,3R)-1-Cyclohexyl-1,2,3,4-tetrahydro-beta-carboline-3-carboxamide, 1-Methoxycarbonyl-1-(1,1'-Biphenyl-4-yl)methyl (1R,3R)-1-Cyclohexyl-2-tert-butoxycarbonyl-1,2,3,4-tetrahydro-beta-carboline-3-carboxamide, (3R)-1-(1-benzylindol-3-yl)-2-tert-butoxycarbonyl-1,2,3,4-tetrahydro-beta-carboline-3-carboxylic Acid, (3R)-1-(1-butylindol-3-yl)-2-tert-butoxycarbonyl-1,2,3,4-tetrahydro-beta-carboline-3-carboxylic Acid, 1-Methoxycarbonyl-1-(1,1'-Biphenyl-4-yl)methyl (3R)-1-(1-butylindol-3-yl)-1,2,3,4-tetrahydro-beta-carboline-3-carboxamide, 1-Methoxycarbonyl-1-(1,1'-Biphenyl-4-yl)methyl (3R)-1-(1-butylindol-3-yl)-1,2,3,4-tetrahydro-beta-carboline-3-carboxamide, 1-Dimethylcarbamoyl-1-(1,1'-biphenyl-4-yl)methyl (1S,3R)-1-(1,1'-Biphenyl-4-yl)-1,2,3,4-tetrahydro-beta-carboline-3-carboxamide, (1S,3R)-1-(Indol-3-yl)-2-tert-butoxycarbonyl-1,2,3,4-tetrahydro-beta-carboline-3-carboxylic Acid, 1-(2,4,6-trimethoxybenzylcarbamoyl)-1-(1,1'-Biphenyl-4-yl)methyl (1S,3R)-1-Cyclohexyl-2-tert-butoxycarbonyl-1,2,3,4-tetrahydro-beta-carboline-3-carboxamide, 1-Benzyloxycarbonyl-1-(1,1'-Biphenyl-4-yl)methyl (1S,3R)-1-(1,1'-Biphenyl-4-yl)-2-tert-butoxycarbonyl-1,2,3,4-tetrahydro-beta-carboline-3-carboxamide, 1-Propoxycarbonyl-1-(1,1'-Biphenyl-4-yl)methyl (1S,3R)-1-Cyclohexyl-2-tert-butoxycarbonyl-1,2,3,4-tetrahydro-beta-carboline-3-carboxamide, 1-Butoxycarbonyl-1-(1,1'-Biphenyl-4-yl)methyl (1S,3R)-1-Cyclohexyl-2-tert-butoxycarbonyl-1,2,3,4-tetrahydro-beta-carboline-3-carboxamide, 1-(2-Methoxy-1-ethoxycarbonyl)-1-(1,1'-Biphenyl-4-yl)methyl (1S,3R)-1-Cyclohexyl-2-tert-butoxycarbonyl-1,2,3,4-tetrahydro-beta-carboline-3-carboxamide, 1-Methoxymethyl-1-(1,1'-Biphenyl-4-yl)methyl (3R)-1-Cyclohexyl-2-tert-butoxycarbonyl-9-methyl-1,2,3,4-tetrahydro-beta-carboline-3-carboxamide, 1-Methoxymethyl-1-(1,1'-Biphenyl-4-yl)methyl (3R)-1-Cyclohexyl-9-methyl-1,2,3,4-tetrahydro-beta-carboline-3-carboxamide, (1S,3R)-1-(1-methylindol-3-yl)-2-tert-butoxycarbonyl-1,2,3,4-tetrahydro-beta-carboline-3-carboxylic acid, 1-(2,4,6-trimethoxybenzylcarbamoyl)-1-(1,1'-Biphenyl-4-yl)methyl (1S,3R)-1-Cyclohexyl-1,2,3,4-tetrahydro-beta-carboline-3-carboxamide, 1-(Benzyloxycarbonyl)-1-(1,1'-Biphenyl-4-yl)methyl (1S,3R)-1-(1,1'-Biphenyl-4-yl)-1,2,3,4-tetrahydro-beta-carboline-3-carboxamide, 1-Propoxycarbonyl-1-(1,1'-Biphenyl-4-yl)methyl (1S,3R)-1-Cyclohexyl-1,2,3,4-tetrahydro-beta-carboline-3-carboxamide, 1-Butoxycarbonyl-1-(1,1'-Biphenyl-4-yl)methyl (1S,3R)-1-Cyclohexyl-1,2,3,4-tetrahydro-beta-carboline-3-carboxamide, 1-(2-Methoxy-1-ethoxycarbonyl)-1-(1,1'-Biphenyl-4-yl)methyl (1S,3R)-1-Cyclohexyl-1,2,3,4-tetrahydro-beta-carboline-3-carboxamide, Benzothiazol-2-yl (1S,3R)-1-Cyclohexyl-2-tert-butoxycarbonyl-1,2,3,4-tetrahydro-beta-carboline-3-carboxamide, Benzothiazol-2-yl (1S,3R)-1-Cyclohexyl-1,2,3,4-tetrahydro-beta-carboline-3-carboxamide, 1,1'-Biphenyl-4-oylmethyl (1S,3R)-1-Cyclohexyl-2-tert-butoxycarbonyl-1,2,3,4-tetrahydro-beta-carboline-3-carboxylate, 1,1'-Biphenyl-4-oylmethyl (1R,3R)-1-Cyclohexyl-2-tert-butoxycarbonyl-1,2,3,4-tetrahydro-beta-carboline-3-carboxylate, 2,4,6-Trimethoxybenzyl (1S,3R)-1-(1-methylindol-3-yl)-1,2,3,4-tetrahydro-beta-carboline-3-carboxamide, 2,4,6-Trimethoxybenzyl (1S,3R)-1-(1-methylindol-3-yl)-1,2,3,4-tetrahydro-beta-carboline-3-carboxamide, 1,1'-Biphenyl-4-oylmethyl (1S)-1-Cyclohexyl-1,2,3,4-tetrahydro-beta-carboline-3-carboxylate, 1-(2-Hydroxy-1-propylcarbamoyl-1-(1,1'-Biphenyl-4-yl)methyl (1S,3R)-1-Cyclohexyl-2-tert-butoxycarbonyl-1,2,3,4-tetrahydro-beta-carboline-3-carboxamide or 1-(2-Oxo-1-propylcarbamoyl-1-(1,1'-Biphenyl-4-yl)methyl (1S,3R)-1-Cyclohexyl-2-tert-butoxycarbonyl-1,2,3,4-tetrahydro-beta-carboline-3-carboxamide.

8. A pharmaceutical composition comprising a pharmaceutically acceptable carrier and a pharmacologically effective amount of the compound of Formula (I) as claimed in claim 1.

9. The pharmaceutical composition of claim 8, in the form of an oral dosage or parenteral dosage unit.

10. The pharmaceutical composition of claim 8, wherein said compound is administered as a dose in a range from about 0.01 to 500 mg/kg of body weight per day.

11. The pharmaceutical composition of claim 8, wherein said compound is administered as a dose in a range from about 0.1 to 200 mg/kg of body weight per day.

12. The pharmaceutical composition of claim 8, wherein said compound is administered as a dose in a range from about 0.1 to 100 mg/kg of body weight per day.

13. The pharmaceutical composition of claim 8, further comprising one or more therapeutic agents selected from the group consisting of alkylating agents, antimetabolites, plant alkaloids, antibiotics, hormones, biologic response modifiers, analgesics, NSAIDS, DMARDS, glucocorticoids, sulfonylureas, biguanides, insulin, choliflesterase inhibitors, antipsychotics, antidepressants, and anticonvulsants.

* * * * *